United States Patent
Sharma

(10) Patent No.: US 6,331,285 B1
(45) Date of Patent: *Dec. 18, 2001

(54) STRUCTURALLY DETERMINED CYCLIC METALLO-CONSTRUCTS AND APPLICATIONS

(75) Inventor: Shubh D. Sharma, Plainsboro, NJ (US)

(73) Assignee: Palatin Technologies, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/464,358

(22) Filed: Dec. 15, 1999

Related U.S. Application Data

(62) Division of application No. 08/660,697, filed on Jun. 5, 1996, now Pat. No. 6,027,711.

(51) Int. Cl.[7] ............................ A61K 51/00; A61M 36/14
(52) U.S. Cl. .................. 424/1.69; 424/1.11; 424/1.65; 530/300; 530/317; 530/326; 530/333; 530/334
(58) Field of Search ................................ 424/1.11, 1.65, 424/1.69, 9.1, 9.341, 9.34, 9.3; 534/7, 10–16; 530/300, 324–330, 317, 311, 312, 333, 334, 338

(56) References Cited

U.S. PATENT DOCUMENTS

| | | | |
|---|---|---|---|
| 4,390,528 | 6/1983 | Najjar | 424/177 |
| 4,427,646 | 1/1984 | Olexa et al. | 424/1.1 |
| 4,479,930 | 10/1984 | Hnatowich | 424/1.1 |
| 4,578,079 | 3/1986 | Ruoslahti et al. | 623/11 |
| 4,650,787 | 3/1987 | Schally et al. | 514/11 |
| 4,668,503 | 5/1987 | Hnatowich | 424/1.1 |
| 4,680,276 | 7/1987 | Bach et al. | 436/542 |
| 4,732,864 | 3/1988 | Tolman | 436/547 |
| 4,849,505 | 7/1989 | Stavrianopoulos | 530/300 |
| 4,859,765 | 8/1989 | Nestor, Jr. et al. | 530/333 |
| 4,863,898 | 9/1989 | Ashmead et al. | 514/6 |
| 4,883,861 | 11/1989 | Grill et al. | 530/326 |
| 4,986,979 | 1/1991 | Morgan, Jr. et al. | 424/1.1 |
| 5,023,237 | 6/1991 | Pickart | 514/18 |
| 5,028,593 | 7/1991 | Nishioka | 514/18 |
| 5,059,588 | 10/1991 | Pickart | 514/12 |
| 5,091,176 | 2/1992 | Braatz et al. | 424/78.17 |
| 5,118,665 | 6/1992 | Pickart | 514/6 |
| 5,157,023 | 10/1992 | Lipton | 514/18 |
| 5,196,510 | 3/1993 | Rodwell et al. | 530/324 |
| 5,200,504 | 4/1993 | Ghadiri | 530/304 |
| 5,214,131 | 5/1993 | Sano et al. | 530/345 |
| 5,225,180 | 7/1993 | Dean et al. | 424/1.1 |
| 5,328,840 | 7/1994 | Coller | 435/240.2 |
| 5,371,184 | 12/1994 | Rajagopalan et al. | 530/324 |
| 5,382,513 | 1/1995 | Lam et al. | 435/7.1 |
| 5,382,654 | 1/1995 | Lyle et al. | 530/311 |
| 5,395,609 | 3/1995 | Stuttle | 424/1.69 |
| 5,408,036 | 4/1995 | Ghadiri | 530/304 |
| 5,410,020 | 4/1995 | Ghadiri | 530/333 |
| 5,438,119 | 8/1995 | Rutter et al. | 530/333 |
| 5,440,013 | 8/1995 | Kahn | 530/317 |
| 5,443,815 | 8/1995 | Dean et al. | 424/1.41 |
| 5,443,816 | 8/1995 | Zamora et al. | 424/1.69 |
| 5,464,934 | 11/1995 | Dunn et al. | 530/326 |
| 5,470,753 | 11/1995 | Sepetov et al. | 436/89 |
| 5,475,085 | 12/1995 | Kahn | 530/317 |
| 5,498,538 | 3/1996 | Key et al. | |
| 5,556,609 | 9/1996 | Zamora et al. | 424/1.69 |
| 5,565,325 | 10/1996 | Blake | |
| 5,569,745 | 10/1996 | Goodbody et al. | 530/328 |
| 5,891,418 | * 4/1999 | Sharma | 424/1.69 |
| 6,027,711 | * 2/2000 | Sharma | 424/1.69 |

FOREIGN PATENT DOCUMENTS

| | | |
|---|---|---|
| 2016235 | 9/1990 | (CA) . |
| 94810008.6 | 1/1994 | (EP) . |
| PCT/US92/00757 | 2/1992 | (WO) . |

(List continued on next page.)

OTHER PUBLICATIONS

"Conformational Restrictions on Biologically Active Peptides Via Amino Acid Side Chain Groups" by V. J. Hruby. Life Sciences, vol. 31, pp. 189–199. (1981).

"Complexes of Technetium–99m with Tetrapeptides, a New Class of Tc–labelled Agents" by H.P. Vanbilloen et al. Nuc. Med. Bio., 22: 325–337. (1995).

"Secondary Structure Nucleation in Peptides. Transition Metal Ion Stabilized a–Helices" by M.R. Ghadiri et al. J. Am. Chem. Soc. 1990. vol. 112, No. 4, p. 1630–1632.

(List continued on next page.)

Primary Examiner—Dameron L. Jones
(74) Attorney, Agent, or Firm—Stephen A. Slusher; Peacock, Myers & Adams

(57) ABSTRACT

A metallo-construct, which may be a peptide, is provided for use as a biological, therapeutic, diagnostic imaging, or radiotherapeutic agent, and for use in library or combinatorial chemistry methods. The construct has a conformationally constrained global secondary structure obtained upon complexing with a metal ion. The peptide constructs are of the general formula:

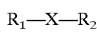

$$R_1—X—R_2$$

where X is a plurality of amino acids and includes a complexing backbone for complexing metal ions, so that substantially all of the valences of the metal ion are satisfied upon complexation of the metal ion with X, resulting in a specific regional secondary structure forming a part of the global secondary structure; and where $R_1$ and $R_2$ each include from 0 to about 20 amino acids, the amino acids being selected so that upon complexing the metal ion with X at least a portion of either $R_1$ or $R_2$ or both have a structure forming the balance of the conformationally constrained global secondary structure. All or a portion of the global secondary structure, which may be sychnologic or rhegnylogic, may form a ligand or mimic a known biological-function domain. The construct has substantially higher affinity for its target upon labeling with a metal ion.

16 Claims, 14 Drawing Sheets

FOREIGN PATENT DOCUMENTS

| | | |
|---|---|---|
| PCT/US92/10716 | 11/1992 | (WO). |
| PCT/US93/02320 | 3/1993 | (WO). |
| PCT/US93/03687 | 4/1993 | (WO). |
| PCT/US93/04794 | 5/1993 | (WO). |
| PCT/US93/05372 | 6/1993 | (WO). |
| PCT/US93/06029 | 6/1993 | (WO). |
| PCT/US94/06274 | 6/1994 | (WO). |
| PCT/US94/08335 | 7/1994 | (WO). |
| WO 97/33626 | 9/1997 | (WO). |
| WO 99/10016 | 3/1999 | (WO). |

OTHER PUBLICATIONS

"Peptide Architecture. Design of Stable a Helical Metallopeptides via a Novel Exchange–Inert Ru iii Complex" by M.R. Ghadiri et al. J. Am Chem. Soc. 1990, vol. 112, No. 26. pp. 9633–9635.

"A Convergent Approach to Protein Design. Metal Ion–Assisted Spontaneous Self–Assembly of a Polypeptide into Triple–Helix Bundle Protein" by M.R. Ghadiri et al. J. Am. Chem. Soc. 1992, vol. 114, No. 3, pp. 825–831.

"Synthesis and Radiochemical Studies of Model Chelators For Tc–99m" by P.R. Singh et al. Proceedings of the 43rd Annual Meeting, Journal of Nuclear Medicine. Jun. 4, 1996. p. 28p.

"A Review of the Utility of Soluble Peptide Combinatorial Libraries" by C. Pinilla et al. Biopolymers (Peptide Science), vol. 37, 1995. pp. 221–240.

"Design of Metal ion Binding Peptides" by R. Fattorusso et al. Biopolymers (Peptide Science), vol. 37, 1995. pp. 401–410.

"Novel Biopolymers for Drug Discovery" by E.J. Moran et al. Biopolymers (Peptide Science) vol. 37, 1995. pp. 213–219.

"One–Bead–One–Structure Combinatorial Libraries" by M. Lebl et al. Biopolymers (Peptide Science) vol. 37, 1995. pp.177–198.

"Discovery of Sequence–Selective Peptide Binding by Synthetic Receptors Using Encoded Combinatorial Libraries" By W.C. Still. Acc. Chem. Res. 1996, vol. 29, No. 3, pp. 155–163.

"Strategy and Tactics in Combinatorial Organic Synthesis. Applications to Drug Discovery" By E.M. Gordon et al. Acc. Chem. Res. 1996, vol. 29, No. 3. pp. 144–154.

"Design, Synthesis, and Evaluation of Small–Molecule Libraries" By J.A. Ellman. Acc. Chem Res. 1996, vol. 29, No. 3. pp. 132–143.

"Multiple–Component Condensation Strategies for Combinatorial Library Synthesis" By R.W. Armstrong et al. Acc. Chem. Res. 1996, vol. 29, No. 3, pp. 123–131.

Guest Editorial by A.W. Czarnik. Accounts of Chemical Research, vol. 29, No. 3, Mar. 1996, pp. 112–113.

"Synthesis and Applications of Small Molecule Libraries" by L.A. Thompson et al. Chem Rev. 1996, vol. 96, No. 1. pp. 555–600.

"Combinatorial Organic Synthesis Using Parke–Davis's Diversomer Method" by S.H. DeWitt et al. Acc. Chem. Res. 1996, vol. 29, No. 3, pp. 114–122.

"The Use of Light–Directed Combinatorial Peptide Synthesis in Epitope Mapping" by C.P. Holmes et al. Biopolymers (Peptide Science) vol. 37, 1995. pp. 199–211.

"The Galvanization of Biology: A Growing Appreciation for the Roles of Zinc" By J.M. Berg et al. Science, vol. 271. Feb. 23, 1996, pp. 1081–1085.

"Imaging Focal Sites of Bacterial Infection in Rats wit Indium–111–Labelled Chemotactic Peptide Analogs" By A.J. Fischman et al. The Journal of Nuclear Medicine, vol. 32, No. 3, Mar. 1991. pp. 483–491.

"Autoradiographic analysis of formylpeptide chemoattractant binding, uptake and intracellular processing by neutrophils" By A.H. Janeczek et al. Journal of Cell Science 94, 1989. pp. 155–168.

"Technetium–99–m–Labeled Chemotactic Peptides: Comparison with Indium–111–Labeled White Blood Cells for Localizing Acute Bacterial Infection in the Rabbit" By J.W. Babich et al. Jour. Nuc. Med., vol. 34 No. 12, 1993. pp. 2176–2181.

"Antithrombotic Properties of L–Cysteine, N–(mercaptoacetyl)–D–Tyr–Arg–Gly–Asp–Sulfoxide (G4120) in a Hamster Platelet–Rich Femoral Vein Thrombosis Model" by Y. Imura et al. Blood, vol. 80 No. 5, 1992. pp. 1247–1263.

"Thrombus Imaging with Technetium–99m Synthetic Peptides Based upon the Binding Domain of a Monoclonal Antibody to Activated Platelets" By L.C. Knight et al. Jour. Nuc. Med., vol. 35 No. 2. 1994. pp. 282–288.

"In–111 Laminin Peptide Fragments for Malignant Tumor Detection" By D. Swanson et al. Jour. Nuc. Med. vol. 34 Np. 5, 1993. p. 231P.

"The use of a chelating derivative of alpha melanocyte stimulating hormone for the clinical imaging of malignant melanoma" By E.P. Wraight et al. British Journal of Radiology, 1992, vol. 65. pp. 112–118.

"BisMSH–DTPA A Potential Imaging Agent for Malignant Melanoma" By D.R. Bard et al. Annals of New York Academy of Sciences, vol. 680, 1993. pp. 451–453.

"Prediction of The Secondary Structure of Proteins from Their Amino Acid Sequence" By P.Y. Chou et al. Graduate Department of Biochemistry, Brandeis University, Pub. No. 1195. pp. 45–148.

"Protein and Amino Acid Chemistry" by V.J. Hruby et al. Synthetic Peptides, A User's Guide, 1992. pp. 11–24.

"Bis(Aminothiol) Oxorhenium Complexes Whose Structure Mimic Steroids" By R. K. Hom et al. J. Nuc. Med., Jun. 14, 1995. p. 68P.

"Conformational Design and Constraint" By V.J. Hruby et al. Synthetic Peptides, A User's Guide, 1992. pp. 58–67.

"Applications of Synthetic Peptides" By V.J. Hruby et al. Synthetic Peptides, A User's Guide, 1992. Chapter 5. pp. 259–345.

"Zinc Coordination, Function, and Structure of Zinc Enzymes and Other Proteins" By B.L. Vallee et al. Biochemistry, vol. 29 No. 24, 1990. pp. 5647–5659.

"Zinc Fingers" By D. Rhodes et al. Scientific American, Feb. 1993. pp. 56–65.

"A Consensus Zinc Finger peptide: Design, High–Affinity Metal Binding, a pH–Dependent Structure, and a His to Cys Sequence Variant" By B.A. Krizek. H. Am. Chem. Soc., vol. 113 No. 12, 1991. pp. 4518–4523.

"Calcium–Induced Peptide Association to Form an Intact Protein Domain: 1H NMR Structural Evidence" By G.S. Shaw et al. Science, Jul., 1990. pp. 280–283.

"Calcium–induced Protein Folding: Structure–Affinity Relationships in Synthetic Analogs of the Helix–Loop–Helix Calcium Binding Unit" By R.E. Reid et al. J. Bio. Chem. vol. 256, No. 6, 1981. pp. 2742–2751.

"Iron (II) Organizes a Synthetic Peptide into Three–Helix Bundles" By M. Lieberman et al. J. Am. Chem. Soc., 1991, vol. 113 No. 4. pp. 1470–1471.

"Conformationally restricted peptides through short–range cyclizations" By C. Toniolo. Int. J. Peptide Protein. Res. 35, 1990. pp. 287–300.

"Peptide–Membrane Interactions and a New Principle in Quantitative Structure–Activity Relationships" By R. Schwyzer, Biopolymers, vol. 31, 1991. pp. 785–792.

"Conformation and complexation with metal ions of cyclic hexapeptides: cyclo (L–Leu–L–Phe–L–Pro)2 and cyclo [L–Cys(Acm)–L–Phe–L–Pro]2" By E. Ozeki et al. Int. J. Peptide Protein Res. 34, 1989. pp. 111–117.

"Design, Synthesis, and Complexing Properties of (1Cys–1'Cys, 4Cys–4'–Cys)–dithiobis(Ac–L1Cys–L–Pro–D–Val–L–4Cys–NH2). The First Example of New Family of Ion–Binding Peptides" J. Am. Chem. Soc. vol. 115–25, pp. 11664–11670. (1993).

"Homodimeric and Heterodimeric Bis(amino thiol) Oxometal Complexes with Rhenium(V) and Technetium(V). Control of Heterodimeric Complex Formation and an Approach to Metal Complexes that Mimic Steroid Hormones" By D.Y. Chi et al. J. Med. Chem., 1994, vol. 37 No. 7, pp. 928–937.

"Protein Structure" By V.J. Hruby et al. Synthetic Peptides, A User's Guide, 1992. pp. 24–33.

"Secondary Structure Prediction" By V.J. Hruby et al. Synthetic Peptides, A User's Guide, 1992. pp. 39–41.

Severin, Kay, et al., "Bioorganiometallic Chemistry–Transition Metal complexes with a–Amino Acids and Peptides," *Agnew. Chemie, International Edition*, vol. 37, No. 12, Jun. 1998, pp. 1635–1654.

Francis, Matthew B., et al., "Combinatorial Libraries of Transition–metal Complexes, Catalysts and Materials," *Cur. Opin. in Chem. Biol.*, vol. 2, Jun. 1998, pp. 422–428.

Francis, Matthew B., et al., "Combinatorial Approach to the Discovery of Novel Coordination Complexes," *J. Amer. Chem. Soc.*, vol. 118, No. 37, Sep. 18, 1996, pp. 8983–8984.

* cited by examiner

STRUCTURALLY DETERMINED CYCLIC METALLO-CONSTRUCTS AND APPLICATIONS

CROSS-REFERENCE TO RELATED APPLICATION

This application is a Divisional application of U.S. Ser. No. 08/660,697, now U.S. Pat. No. 6,027,711 filed Jun. 5, 1996, entitled Structurally Determined Metallo-Constructs and Applications, the teachings of which are incorporated herein by reference as if set forth in full.

BACKGROUND OF THE INVENTION

1. Field of the Invention (Technical Field)

The present invention relates to peptide, peptidomimetic, peptide-like and metallo-constructs, particularly for use in receptor-specific compositions for biological, pharmaceutical and radiopharmaceutical applications, in which the construct is conformationally fixed, with the biological-function domain generally having increased affinity for its target, upon labeling of the metal ion-binding backbone with a metal ion.

2. Background Art

Peptide Drugs. In recent years, a significant number of peptides with various biological effects have been discovered. These peptides are being explored for use as drugs, in treatment or prevention of a variety of diseases. There are significant limitations with use of peptide drugs, including extremely rapid clearance from the circulatory system, low target affinity with some peptides, immunogenicity of larger peptide constructs, and lack of stability against proteolytic enzymes. However, there are peptides in use or under investigation as therapeutic agents for a number of conditions, including somatostatin analogues, arginine vasopressin, oxytocin, luteinizing hormone releasing hormone, angiotensin-converting enzyme, renin and elastase inhibitors, as well as a variety of antagonists, including fibrinogen receptor antagonists, and the like. In addition, peptidomimetic antibiotics and peptide-based vaccines are also in use or development as human drugs.

The problems of immunogenicity and short circulatory half-life are well known, and various modifications to peptide-based drugs have been proposed in attempts to solve these problems. These include the modification of peptides or proteins with a variety of polymers, such as polyethylene glycol (PEG) and polypropylene glycol (PPG). Thus, in U.S. Pat. No. 5,091,176, Polymer-Modified Peptide Drugs Having Enhanced Biological and Pharmacological Activities, to Braatz J A and Heifetz A H, a method is set forth for making polymer-modified drugs, with reduced immunogenicity, increased circulation half-life, and enhanced potency. A different method is disclosed in U.S. Pat. No. 5,214,131, Polyethylene Glycol Derivatives, Modified Peptides and Production Thereof, to Sano A, Maeda H, Kai Y and One K.

Peptide-Based Radiopharmaceutical Drugs. Biologically active peptides, which are peptides which bind to specific cell surface receptors, have received some consideration for use as radiopharmaceuticals. Canadian Patent Application 2,016,235, Labeled Chemotactic Peptides to Image Focal Sites of Infection or Inflammation, teaches a method of detecting a site of infection or inflammation, and a method for treating such infection or inflammation, by administration of a labeled or therapeutically-conjugated chemotactic peptide. In this application, the chemotactic peptides are chemically conjugated to DTPA and subsequently labeled with $^{111}$In. The utility of DTPA chelates covalently coupled to polypeptides and similar substances is well known in the art. See, for example, U.S. Pat. Nos. 4,479,930 and 4,668,503 to Hnatowich D J. Other bifunctional chelates for radiolabeling peptides, polypeptides and proteins are well known in the art. Biologically active peptides are described in U.S. Pat. No. 4,427,646, Use of Radiolabeled Peptide Derived From Crosslinked Fibrin to Locate Thrombi In Vivo, to Olexa S A, Knight L C and Budzynski A Z, in which iodination is discussed as a means of radiolabeling. In U.S. Pat. No. 5,371,184, Radiolabelled Peptide Compounds, to Rajagopalan R, Lyle L R and Dunn T J, hirudin receptor-specific peptides, radiolabeled via a chelate ligand, are disclosed. In U.S. Pat. No. 4,986,979, Imaging Tissue Sites of Inflammation, to Morgan C A Jr and Anderson D C, use of chelates and direct iodination is disclosed. In U.S. Pat. No. 4,732,864, Trace-Labeled Conjugates of Metallothionein and Target-Seeking Biologically Active Molecules, to Tolman G L, the use of metallothionein or metallothionein fragments conjugated to a biologically active molecule, including peptides, is disclosed. In Dean R T and Lister-James J, International Application No. PCT/US93/05372, Technetium-99m Labeled Peptides for Imaging; Dean R T and Lister-James J, International Application No. PCT/US93/04794, Technetium-99m Labeled Peptides for Thrombus Imaging; Dean R T, Buttram S, McBride W, Lister-James J, and Civitello E R, International Application No. PCT/US93/03687, Technetium-99m Labeled Peptides for Imaging; Dean R T, Lees R S, Buttram S and Lister-James J, International Application No. PCT/US93/02320, Technetium-99m Labeled Peptides for Imaging Inflammation; and Dean R T, McBride W and Buttram S, International Application No. PCT/US92/10716, Technetium-99m Labeled Peptides for Imaging a variety of peptide constructs are disclosed, all involving a Tc-99m binding moiety covalently or otherwise linked to the peptide, or to a polyvalent linker moiety, which is itself linked to one or more peptides. These previous methods all employ some conjugation means with a chelator in order to effectuate labeling with a radionuclide or other medically useful metal ion, such as a paramagnetic contrast agent. The only exception involves direct radioiodination; the iodine labeling of proteins or peptides containing tyrosine or histidine residues is well known, for example, by the chloramine-T, iodine monochloride, Iodogen or lactoperoxidase methods.

In U.S. Pat. No. 5,225,180, Technetium-99m Labeled Somatostatin-Derived Peptides for Imaging, to Dean R T, Lister-James J and Buttram S, technetium-99m labeling of peptides containing at least two cysteine residues capable of forming a disulfide bond through reduction of the disulfide is disclosed. Other somatostatin-based radiopharmaceuticals are disclosed in U.S. Pat. No. 5,382,654, Radiolabelled Peptide Compounds, to Lyle L R, Rajagopalan R, and Deutsch K; Albert R and Macke H, European Patent Application No. EP948 10008.6, Somatostatin Analogs Containing Chelating Groups and Their Radiolabeled Compositions; Dean R T, McBride W and Lister-James J, International Application No. PCT/US94/06274, Radiolabeled Somatostatin-Derived Peptides for Imaging and Therapeutic Uses; and McBride W and Dean R T, International Application No. PCT/US94/08335, Somatostatin Derivatives and Their Radiolabelled Products. Use of peptide radiopharmaceuticals in general, not limited to somatostatin analogues, and various examples thereof, are given in Fischman A J, Babich J W, Strauss H W: A Ticket to Ride: Peptide Radiopharmaceuticals. *J Nucl Med* 34:2253–2263, 1993. A method of metal chelation, using amino acid sequences that are capable of forming metal complexes and which are directly incorporated into peptides at nonbiologically active locations has been disclosed. U.S. Pat. No. 5,464,934, Metal Chelates as Spacer Compounds in Biologically Active Peptides, to Dunn T J, Srivivasan A, Lyle L R, Rajagpalan R.

Other biologically active peptides include analogues of formyl peptide chemoattractants which bind to neutrophils. These peptides are based on the sequence N-formyl-Met-Leu-Phe. The clinical and diagnostic imaging potential of formylated chemotactic peptides has been demonstrated by Fischman et al. (Fischman A J, Pike M C, Kroon D, Fucello A J, Rexinger D, tenKate C, Wilkinson R, Rubin R H and Strauss H W: Imaging focal sites of bacterial infection in rats with indium-111-labeled chemotactic peptide analogs. *J Nucl Med* 32:483–491, 1991) using chemotactic peptides chemically conjugated to DTPA and subsequently labeled with $^{111}$In. Chemotactic peptides have also been radioiodinated by synthesizing formylated peptides containing tyrosine amino acids. These peptides have been used in vitro and have the same biological function as unlabeled formylated peptides (Janeczek A H, Marasco W A, Van Alten P J and Walter R B: Autoradiographic analysis of formylpeptide chemoattractant binding, uptake and intracellular processing by neutrophils. *J Cell Sci* 94:155–168, 1989). Finally, chemotactic peptides have also been labeled with $^{99m}$Tc using a nicotinyl hydrazine bifunctional chelate approach (Babich J W, Graham W, Barrow S A, Dragotakes S C, Tompkins R G, Rubin R H and Fischman A J: Technetium-99m-labeled chemotactic peptides: comparison with Indium-111-labeled white blood cells for localizing acute bacterial infection in the rabbit. *J Nucl Med* 34:2176–2181, 1993).

Peptides containing the adhesive sequence RGD are under active investigation as anti-thrombotic agents (Imura Y, Stassen J-M, Dunting S, Stockmans F, and Collen D: Anti-thrombotic properties of L-cysteine, N-(mercaptoacetyl)-D-Tyr-Arg-Gly-Asp-sulfoxide (G4120) in hamster platelet-rich femoral vein thrombosis model, *Blood* 80:1247–1253, 1992). Knight et al. (Knight L C, Radcliffe R, Maurer A H, Rodwell J D and Alvarez V L: Thrombus imaging with Tc-99m synthetic peptides based upon the binding domain of a monoclonal antibody to activated platelets. *J Nucl Med* 35:282–288, 1994) have reported on the use of $^{99m}$Tc-synthetic peptide-metallothionein complexes, containing the radiometal binding sequence Lys-Cys-Thr-Cys-Cys-Ala, which bind to the platelet glycoprotein IIb/IIIa complex to image fresh thrombi in jugular and femoral veins. Other RGD-containing sequences are disclosed in U.S. Pat. No. 5,395,609, Synthetic Peptides for Use in Tumor Detection, to Stuttle A W J.

Radiolabeled peptide constructs, with two binding sequences coupled to DTPA, have been reported. A dimer $^{111}$In-DTPA-labeled laminin sequence was prepared for tumor imaging, in which the dimer was formed by reacting a peptide sequence containing a single YIGSR with DTPA dianhydride, yielding a dimer represented by the formula DTPA-(GYIGSR-NH$_2$)$_2$. In preliminary studies the dimer was more potent than a peptide with a single YIGSR sequence. Swanson D, Epperly M, Brown M L et al: In-111 laminin peptide fragments for malignant tumor detection. *J Nucl Med* 34:23 1P, 1993 (Abstract). A dimer of a melanotropin analogue linked to $^{111}$In-DTPA in a similar fashion has also been reported as an imaging agent for metastatic melanoma. Wraight E P, Bard D R, Maughan T S et al, *Br J Radiology* 65:112–118, 1992; and Bard D R, Wraight E P, Knight C G: BisMSH-DTPA: a potential imaging agent for malignant melanoma. *Ann NY Acad Sci* 680:451–453, 1993.

Structure of Peptides. The folding of linear chain amino acids in peptides and proteins in a very distinctive manner is responsible for their unique three dimensional structure. It is now clear that the side chains of individual amino acids have a preferential propensity to nucleate a particular secondary structure (Chou P Y and Fasman G D: Prediction of the secondary structure of proteins from their amino acid sequence. In *Advances in Enzymology*, Vol. 47 (1978) pp. 45–145, John Wiley & Sons, New York). The properties of these side chains, such as steric bulk and inherent hydropathicity, cause the peptide chain to fold as a helix, sheet, or a reversed turn. In addition to these local effects, both covalent as well as noncovalent interactions between distant as well as adjacent amino acids in the chain also play a very important role in determining, stabilizing and biasing a particular three dimensional structure. Examples of non-covalent interactions include hydrophobic interactions, van der Waals' forces, and hydrogen bonds. Electrostatic interactions in the form of a salt bridge between a positively charged side chain and a negatively charged side chain are common, and stabilize a peptide or protein in a particular configuration. The most important type of covalent interaction between two amino acids in a chain is the formation of a disulfide linkage between two Cys residues that nucleates a particular conformational preference in the molecules. These interactions can be short range (local or regional) or long range (global).

Most of the elements for inducing and stabilizing a conformational preference in naturally occurring proteins and peptides have been used to design and synthesize a wide variety of peptide analogues with preferred or biased conformational characteristics. Examples of structural changes in peptides to cause conformational bias and restriction have been discussed in the literature (Hruby V J: Conformational restrictions of biologically active peptides via amino acid side chain groups. *Life Sciences* 31:189–199, 1981). The incorporation of modified amino acids, such as $N^\alpha$-Methyl or $C^\alpha$-Methyl amino acids or other designer amino acids with conformationally restricted side chains, causes a strong local conformational effect. In synthetic peptides long range or global conformational restriction can routinely be achieved by cyclizing a peptide through appropriate amino acid end groups or side chains. The types of cyclic bridges commonly employed are disulfide bridges between two Cys residues in the peptide chain, and related thioester and thioether bridges, and formation of a lactam or lactone bridge between appropriate chemical groups in the amino acid side chains. Numerous highly potent analogues of many biologically active peptides have been designed using these approaches. Examples include peptide hormones such as somatostatin, opioid peptide, melanotropin, neurokinins, glucagon, and ACTH analogues. Hruby V J, Sharma S D, Collins N, Matsunaga T O and Russel K C: Applications of synthetic peptides, in *Synthetic Peptides, A User's Guide*, Grant G A, editor, W. H Freedman and Company, 1992, pp. 259–345.

Peptide-Metal Ion Interaction. Metal ion complexation within a given amino acid sequence, such as encountered in certain proteins, also appears to effect conformational restriction. Specific structures, called Zinc fingers, in various DNA transcription factors result from complexation of Zn ions to a specific amino acid sequence in the protein. In Vallee B L and Auld D S: Zinc coordination, function, and structure of zinc enzymes and other proteins, *Biochemistry* 29:5648–5659, 1990, the general characteristics of non-metallothionein proteins which contain zinc binding sites are described. Similarly, a family of calcium binding proteins, including calmodulin and related proteins, have highly conserved domains for complexation of Ca ions. These metal binding proteins have unique functional roles in the body that are displayed after the metal ion has complexed to them. The complexation process is known to cause a switch in conformational characteristics which in turn triggers the functional response exerted by the protein.

The area of peptide-metal ion complexation receiving the most interest involves zinc fingers, natural sequences with specific Zn binding domains in transcription proteins that mediate gene regulation (Rhodes D and Klug A: Zinc fingers. *Scientific American* 268(2):56–65, 1993). The reported zinc fingers which have been synthesized and studied for metal binding characteristics in respect to confornational restriction and peptide folding are not of biological relevance, since they are not capable of establishing site-specific interactions with DNA in a manner similar to the transcription proteins that incorporate these zinc fingers. Krizek B A, Amann B T, Kilfoil V J, Merkle D L, and Berg J M: A consensus zinc finger peptide: Design, high affinity metal binding, a pH-dependent structure, and a His to Cys sequence variant. *J Amer Chem Soc* 113:4518–4523, 1991.

Metal ion induced switches in the tertiary structure of synthetic peptides have been shown in some model studies. Reid, Hodges and co-workers (Shaw G S, Hodges R S, Sykes B D: Calcium-induced peptide association to form an intact protein domain: 1H NMR structural evidence. *Science* 249:280, 1990; and Reid R E, Gariepy J, Saund A K, Hodges R S: *J Biol Chem.* 256:2742, 1981) showed that a peptide fragment related to a natural calcium binding protein exhibits enhanced α-helical structure upon binding to calcium. This is due to dimerization of two helical peptide segments located at each end, which is induced by complexation of a calcium ion in the middle peptide segment. Sasaki and co-workers (Lieberman M, Sasaki T: *J Am Chem Soc* 113:1470, 1991) have attached a metal binding chelator to one end of a peptide with a low propensity to form an α-helical structure. Upon complexation with an iron ion three peptide-chelator molecules complex with one metal ion to form a helix bundle. Formation of three-dimensional arrays of the existing secondary structure in these examples, although caused by the complexing metal ion, is not entirely stabilized by it. The helical segments involved in forming a bundle of two or three helices are amphiphilic. The main role of the complexing metal ions in these cases has been to bring these amphiphilic helices close enough so that they interact with each other through amphiphilic interactions, thereby stabilizing the helical bundle.

Stabilization of the alpha helix in short peptides has been reported by making an exchange-inert ruthenium$^{III}$ complex (Ghadiri M R and Femholz A K: Peptide architecture. Design of stable α-helical metallopeptides via a novel exchange-inert Ru$^{III}$ complex. *J Am Chem Soc* 112:9633–9635, 1990) or exchange-labile Cu, Zn, or Cd complex (Ghadiri M R and Choi C: Secondary structure nucleation in peptides. Transition metal ion stabilized α-helices. *J Am Chem Soc* 112:1630–1632, 1990) with peptides that have a propensity to form helical structures. In these 17 amino acid-long peptides two His residues or a Cys and a His residue were placed at i and i+4 positions which would reside on the same side of two consecutive turns in an α-helix and formed an exchange-inert complex with cis[Ru(III)(NH$_3$)$_4$(H$_2$O)$_2$]$^{2+}$ or exchange-labile complex with Zn, Cu, or Cd. The resulting complexes were shown by circular dichroism studies to be of higher helical content. In this art, incorporated generally into U.S. Pat. No. 5,200,504, Metallopeptides Having Stabilized Secondary Structures, to Ghadiri M R; U.S. Pat. No. 5,408,036, Isolated Metallopeptide: Compositions and Synthetic Methods, to Ghadiri M R; U.S. Pat. No. 5,410,020, Methods for Preparing Metallopeptides Having Stabilized Secondary Structures, to Ghadiri M R, the peptide molecule provides only two of the metal chelation sites. The other valences of the metal coordination sphere are satisfied by other unidentate ligands such as NH$_3$. H$_2$O, solvents or halide atoms. Another distinguishing feature of this art is that the two metal complexation sites in the peptide are provided by distant (non-contiguous) amino acids separated by at least two or more amino acids. This method has also been used to induce metal ion-assisted spontaneous self-assembly of polypeptides into three helix (Ghadiri M R, Soares C, Choi C: A convergent approach to protein design. Metal ion-assisted spontaneous self-assembly of a polypeptide into a triple-helix bundle protein. *J Am Chem Soc* 114:825–831, 1992) and four-helix bundles (Ghadiri M R, Soares C, Choi C: Design of an artificial four-helix bundle metalloprotein via novel Ruthenium(II)-assisted self-assembly process. *J Am Chem Soc* 114:4000–4002, 1992). In both cases, an amphiphilic polypeptide designed with the propensity to form an α-helix, with a metal chelator attached at its N-terminus, was complexed to a metal ion which caused it to trimerize or tetramerize with very high helical content. It is evident that the resulting helical bundle was composed of homomeric chains. Formation of metal ion assisted helical bundles with heteromeric polypeptide chains has not yet been demonstrated.

Peptide Libraries and Combinatorial Chemistry. Combinatorial chemistry techniques are now well recognized tools for rapid drug discovery. A library of peptides and other small molecules, with its enormous pool of structurally diverse molecules, is well suited for both lead generation as well as lead optimization. Libraries of a variety of molecular species have been described in literature and screened for drug discovery. These molecular species include peptides, peptoids, peptidomimetics, oligonucleotides, benzodiazepines, and other libraries of small organic molecules.

Various approaches used to construct a library of structurally diverse chemical compounds include chemical synthesis and genetic engineering methods. Chemically synthesized libraries can be either soluble (a mixture of various compounds in a solution) or solid (compounds synthesized on a solid surface). Libraries produced by genetic engineering tools are largely composed of peptide molecules, and are similar to solid-phase libraries in the sense that the peptide molecules are displayed or attached on the surface of vectors or bacteriophages used for their production.

The prior art on designing, synthesizing, screening, and evaluation of peptide-based libraries has been reviewed in the following articles, incorporated herein by reference: Pinilla C et al: A review of the utility of soluble peptide combinatorial libraries. *Biopolymers (Peptide Sci)* 37:221–240, 1995; Lebl M et al: One-bead-one-structure combinatorial libraries. *Biopolymers(Peptide Sci)* 37:177–198, 1995; Holmes C P et al: The use of light-directed combinatorial peptide synthesis in epitope mapping. *Biopolymers(Peptide Sci)* 37:199–211, 1995; and, Moran E J et al: Novel biopolymers for drug discovery. *Biopolymers(Peptide Sci)* 37:213–219, 1995.

The prior art in construction and screening of small molecule libraries, including non-peptide libraries, has recently been reviewed extensively in a "Special Issue on Combinatorial Libraries" appearing in *Accounts of Chemical Sciences,* 29:111–170, 1996. Articles therein applicable hereto include: Czarnik A W: Guest Editorial, at 112–113;

DeWitt S H et al: Combinatorial organic synthesis using Parke-Davis's DIVERSOMER method, at 114–122; Armstrong R W et al: Multiple-component condensation strategies for combinatorial library synthesis, at 123–131; Ellman J A: Design, synthesis, and evaluation of small molecule libraries, at 132–143; Gordon E M et al: Strategy and tactics in combinatorial organic synthesis. Applications to drug discovery, at 144–154; Still WC: Discovery of sequence selective peptide binding by synthetic receptors using encoded combinatorial libraries, at 155–163; and, Hsieh-Wilson L C et al: Lessons from the immune system: From catalysis to material sciences, at 164–170. Also of note is Thompson L A and Ellman J A: Synthesis and applications of small molecule libraries. *Chem Rev* 96:555–600, 1996. The teachings of all the foregoing articles are incorporated by reference.

Phage Display Libraries. Phage display methods of preparing large libraries of peptides (up to $10^6$–$10^8$ chemically different peptides) are now well established (Scott and Smith: *Science* 249:386–390, 1990; Devlin et al: *Science* 249:404–406, 1990; Cwirala et al: *Proc Natl Acad Sci USA* 87:6378–6382, 1990; and U.S. Pat. Nos. 5,432,018; 5,338,665; and 5,270,170). In these libraries, the individual peptides are displayed on the surface of bacteriophages or other suitable vectors and are used in screening assays against the target receptor. Because of inherent properties of biological systems, these methods in general are limited to construction of simple straight-chain peptide libraries with only natural amino acids. These methods also do not allow for further chemical modification in the peptides after the construction of a phage display library.

Spatially Addressable Parallel Synthesis of Solid Phase Bound Libraries. Various strategies for chemical construction of a library of peptides or other small molecules are also well established. One strategy involves spatially separate synthesis of compounds in parallel on solid phase or on a solid surface in a predetermined fashion so that the location of one compound or a subset of compounds on the solid surface is known. The first such method was developed by Geysen for peptide epitope mapping (Geysen H M, Meloen R H, Barteling S J: *Proc Natl Acad Sci USA* 81:3998–4002, 1984). This method involves synthesis of various sets and subsets of a library of peptides on a multiple number of polypropylene pin tips in a predetermined fashion. The screening of these pin-based peptides is done by immersing one pin per well, the well containing the assay reagents and components, in multiwell titer plates. Pin loading levels range from 100 nM to 50 $\mu$M, which is sufficient for conducting multiple biological assays. The assembly of a library of greater than 10,000 molecules by this method is, however, cumbersome and time consuming. The "light-directed spatially addressable parallel chemical synthesis" technique (Fodor SPA et al: *Science* 251:767–773, 1991), based upon use of photolithographic techniques in peptide synthesis on a solid surface, such as a borosilicate glass microscope slide, is a better method of constructing libraries containing more than 100,000 spatially separated compounds in a pre-determined fashion. However, synthesis of libraries that are structurally more diverse than simple peptides requires the development of orthogonal photolabile protecting groups that can be cleaved at different wavelengths of light. In addition, the solid surface bearing these libraries also has been reported to cause a pronounced effect on binding affinities in library screening assays (Cho CY et al: *Science* 261:1303–1305, 1993; Holmes C P et al: *Biopolymers* 37:199–211, 1995).

The DIVERSOMER® apparatus designed by DeWitt and coworkers at Parke-Davis Pharmaceutical Research Division of Warner-Lambert Company, Ann Arbor, Mich., USA, offers a convenient and automated parallel synthesis of small organic molecule libraries on a solid phase (DeWitt S H et al: *Proc Natl Acad Sci USA* 90:6909–6913, 1993; U.S. Pat. No. 5,324,483; DeWitt S H et al: *Acc Chem Res* 29:114–122, 1996). Another conceptually similar apparatus for the solid phase synthesis of small organic molecule libraries has been reported by Meyers and coworkers (Meyers H V et al: *Molecular Diversity* 1:13–20, 1995). A commercial instrument is also now available (Advanced ChemTech Inc, Louisville, Ky., USA). This instrument can produce 96 different compounds in a parallel synthesis and is compatible with a wide range of reaction conditions, temperatures, mix times and other parameters.

Pooling and Split Synthesis Strategies. Large libraries of compounds are assembled by a pooling strategy that employs equimolar mixtures of reactants in each synthetic step (Geysen H M et al: *Mol Immunol* 23:709–715, 1986) or preferably by adjusting the relative concentration of various reactants in the mixture according to their reactivities in each of the coupling reactions (Ostresh J M et al: *Biopolymers* 34:1681–1689, 1994; U.S. Pat. No. 5,010,175 to Rytter W J and Santi D V). The split synthesis approach was pioneered by A. Furka (Furka A et al, (1988), 14*th International Congress of Biochemistry*, Vol. 5, Abstract No. FR:013; Furka A et al: *Int J Peptide Protein Res* 37:487–493, 1991; Sebestyen F et al: *BioMed Chem Lett* 3:413–418, 1993), in which equimolar mixtures of compounds are obtained by splitting the resin in equal portions, each of which is separately reacted with each of the various monomeric reagents. The resin is mixed, processed for the next coupling, and again split into equal portions for separate reaction with individual reagents. The process is repeated as required to obtain a library of desired oligomeric length and size. This approach is also the basis of the "one-bead one-peptide" strategy of Lam et al. (Lam K S et al: *Nature* 354:82–84, 1991; Lam K S et al: *Nature* 360:768, 1992) which employs amino acid sequencing to ascertain the primary structure of the peptide on a hit bead in a bioassay. Automated systems have been developed for carrying out split synthesis of these libraries with rather more efficiency (Zukermann R N et al: *Peptide Res* 5:169–174, 1992; Zukermann R N et al: *Int J Peptide Protein Res* 40:497–506, 1992). A common artifact occasionally seen with all these resin bound libraries is altered target-specific affinity by some solid phase bound compounds in bioassays, which can result in totally misleading results. Another highly successful strategy that overcomes this problem is construction of soluble libraries (Houghten R A et al: *Proc Natl Acad Sci USA* 82:5131–5135, 1985; Berg et al: *J Am Chem Soc* 111:8024–8026, 1989; Dooley C T et al: *Science* 266:2019–2022, 1994; Blondelle S E: *Antimicrob Agents Chemother* 38:2280–2286, 1994; Panilla C: *Biopolymers* 37:221–240, 1995). This strategy involves a deconvolution process of iterative re-synthesis and bioassaying until all the initially randomized amino acid positions are defined. Several modifications to this strategy have also been suggested. For example, co-synthesis of two libraries containing orthogonal pools, as demonstrated by Tartar and coworkers, eliminates the need of iterative re-synthesis and evaluation (Deprez B et al: *J Am Chem Soc* 117: 5405–5406, 1995). The positional scanning method devised by Houghton and coworkers eliminates iterative re-synthesis (Dooley C T et al: *Life Sci* 52:1509–1517, 1993; Pinilla C et al: *Biotechniques* 13:901–905, 1992; Pinilla C et al: *Drug Dev Res* 33:133–145, 1992). A combination of this strategy with the split synthesis methods described above has also been proposed (Erb E et al: *Proc Natl Acad Sci USA,* 91:11422–11426, 1994). A major problem with the soluble library approach involves its successful applicability to high affinity systems. The abundance of each compound in solution can be influenced by the total number of compounds in a library which can affect the biological activity. For this reason, a highly active compound in any pool may not in fact be the most potent molecule. Lack of reasonable solubilities of certain members in a library may further influence this phenomenon. In fact, for several libraries the most active peptide was not even identified in the most active library pool (Dooley C T et al: *Life Sci* 52:1509–1517, 1993; Eichler J, in *Proc. 23rd Eur. Peptide Symp.,* Berga, September 1994, Poster 198; Wyatt J R: *Proc Natl Acad Sci USA,* 91:1356–1360, 1994).

Various strategies for determination of the structure for a positive hit in a random library have been developed. For a solid-phase library, direct analytical modalities include Edman degradation for peptide libraries, DNA sequencing of oligonucleotide libraries, and various mass spectrometry techniques on matrix bound compounds. The technique of creating a series of partially end-capped compounds at each of the synthetic steps during library assembly helps their unambiguous identification by mass spectrometry (Youngquist R S et al: *J Am Chem Soc* 117:3900–3906, 1995; Youngquist R S et al: *Rapid Commun Mass Spectr* 8:77–81, 1994). This technique has been claimed to be universally applicable to a wide variety of chemically diverse libraries. Direct mass spectrometric analysis of compounds covalently bound to a solid phase matrix of particles is also now possible by the use of matrix-assisted laser desorption/ionization (MALDI) techniques (Siuzadak G et al: *Bioorg Med Chem Lett* 6:979, 1996; Brown B B et al: *Molecular Diversity* 1:4–12, 1995). In addition to these analytical techniques, various encoding strategies have been devised for structure elucidation in organic molecule-based libraries, including both non-peptide and non-nucleotide libraries. Various coding strategies include DNA encoding, peptide coding, haloaromatic tag encoding, and encoding based on radiofrequency transponders.

Most of the libraries described above are termed "random" libraries because of their enormous structural and conformational diversity. Libraries of relatively restricted and biased structures have also been reported. Examples of libraries of conformationally rigid compounds built on a structurally common template include benzodiazepine, β-lactam, β-turn mimetics, diketopiperazines, isoquinolines, dihydro- and tetrahydroisoquinolines, 1,4 dihydropyridines, hydantoins, pyrrolidines, thiazolidine4-carboxylic acids, 4-thiazolidines and related 4-metathiazanones and imidazoles.

Among the various classes of libraries of small molecules, peptide libraries remain the most versatile because of the structural diversity offered by the use of naturally occurring amino acids, incorporation of a variety of designer amino acids, and the high efficiency and ease with which peptide synthesis can be accomplished. In addition, another level of structural diversity in peptide-based libraries has been added by post-synthesis modification of the libraries. These modifications include permethylation, acylation, functionalization of the side chain functionality, and reductive amination of the N-terminus.

Many libraries specifically customized for one particular biological target have also been reported. These libraries are generally assembled by incorporating only a set of structural elements that might be essential for eliciting a target-specific response. Some of the reported libraries of this class include aspartic acid protease, zinc proteases, carbonic anhydrase inhibitors, tyrosine kinase inhibitors, estrogen receptor ligands, and antioxidants.

SUMMARY OF THE INVENTION (DISCLOSURE OF THE INVENTION)

Metallo-Constructs. In accordance with the present invention, there are provided metallo-constructs, which include a metal ion-binding backbone for complexing with a metal ion, and a biological-function domain, in which the biological-function domain conformationally constrained upon complexing the metal ion-binding backbone with the metal ion, and optionally including the metal ion. In these metallo-constructs, at least a portion of the construct may be conformationally constrained in a secondary structure upon complexing the metal ion-binding backbone with the metal ion. Optionally, the constructs may have a conformationally constrained global structure upon complexing the metal ion-binding backbone with the metal ion. In general, the biological-function domain is substantially more potent upon complexation of the metal ion-binding backbone with the metal ion. The biological-function domain may be sychnological or rhegnylogical.

The metal ion-binding backbone may be constructed of amino acids, or may be constructed such that it has available nitrogen, sulfur or oxygen atoms to complex the metal ion, and may be based on metal binding chelate structures. In these metallo-constructs, the metal ion-binding backbone may include a plurality of amino acids, with substantially all of the valences of the metal ion satisfied upon complexation of the metal ion to nitrogen, sulfur or oxygen atoms in the amino acids available for complexing with the available valences of the metal ion. The metallo-constructs may thus be characterized by the metal ion-binding backbone including a plurality of amino acids each containing at least one nitrogen, sulfur or oxygen atom available for complexing with the available valences of the metal ion. The metal ion-binding backbone may also include a derivatized amino acid or spacer sequence, wherein the derivatized amino acid or spacer sequence includes at least one nitrogen, sulfur or oxygen atom available for complexing with the available valences of the metal ion, so that all of the valences of the metal ion are satisfied upon complexation of the metal ion.

The biological-function domain of the metallo-complex may constitute a ligand capable of forming a member of a ligand and receptor pair. In such instance, the affinity of the ligand for its receptor will generally be substantially higher when the metal ion-binding backbone is complexed with the metal ion than the affinity of the ligand for its receptor when the metal ion-binding backbone is not complexed with the metal ion.

The metal ion may be an ionic form of the elements iron, cobalt, nickel, copper, zinc, manganese, arsenic, selenium, technetium, ruthenium, palladium, silver, cadmium, indium, antimony, rhenium, osmium, iridium, platinum, gold, mercury, thallium, lead, bismuth, polonium or astatine.

Metallopeptides. The invention also includes manufactured peptides and pharmaceutically acceptable salts which include a metal ion-binding backbone with two or more contiguous amino acids available for complexing with a metal ion, and a biological-function domain, which biological-function domain is conformationally constrained upon complexing the metal ion-binding backbone with a metal ion. The peptide may also include the metal ion, and thus be a metallopeptide. In general, at least a portion of the peptide is conformationally constrained in a secondary structure upon complexing the metal ion-binding backbone with the metal ion. The peptide may have a conformationally constrained global structure upon complexing the metal ion-binding backbone with the metal ion. The biological-function domain of the peptide is, in most instances, substantially more potent upon complexation of the metal ion-binding backbone with the metal ion. The peptide may also be, in many instances, characterized by being substantially resistant to enzymatic degradation upon complexing the metal ion-binding backbone with a metal ion.

For most applications, the metal ion-binding backbone is designed so that all of the valences of the metal ion are satisfied upon complexation of the metal ion. In such instances, the metal ion-binding backbone may be a plurality of amino acids each containing at least one nitrogen, sulfur or oxygen atom available for complexing the available valences of the metal ion. If less than all of the valences of the metal ion are otherwise satisfied upon complexation of the metal ion with the amino acids which are included in the metal ion-binding backbone, then the metal ion-binding backbone also may include a derivatized amino acid or spacer sequence, which derivatized amino acid or spacer sequence contains at least one nitrogen, sulfur or oxygen atom available for complexing with the available valences of the metal ion, so that all of the valences of the metal ion are satisfied upon complexation of the metal ion.

The biological-function domain of the peptide may be a ligand capable of forming a member of a ligand and receptor pair. In such cases, the affinity of the ligand for its receptor is generally substantially higher when the metal ion-binding backbone is complexed with the metal ion than is the affinity of the ligand for its receptor when the metal ion-binding backbone is not complexed with the metal ion. In any event, the biological-function domain may be sychnological or rhegnylogical.

The metal ion complexed to the peptide may be an ionic form of the elements iron, cobalt, nickel, copper, zinc, manganese, arsenic, selenium, technetium, ruthenium, palladium, silver, cadmium, indium, antimony, rhenium, osmium, iridium, platinum, gold, mercury, thallium, lead, bismuth, polonium or astatine. The metal ion may also be a medically useful metal ion. In such cases, the metal ion may be radioactive or paramagnetic.

The peptides may also be cyclic peptides, and may be cyclized through an amide, disulfide, thioether, thioester, urethane, carbamate, or ester linkage. Such cyclization may also be through a covalent linkage through the end groups of the peptide, covalent linkage through side chain functionalities of any two amino acids within the peptide, or covalent linkage through one end group of the peptide and a side chain functionality of any amino acid in the peptide.

Structure of Metallopeptides. The peptides and pharmaceutically acceptable salts thereof have a conformationally constrained secondary structure upon complexing with a metal ion. This conformationally constrained secondary structure may constitute a member of a ligand and receptor pair. These peptides are of the general formula:

wherein X is a complexing backbone for complexing a metal ion comprising a plurality of contiguous amino acids, so that substantially all of the valences of the metal ion are satisfied upon complexation of the metal ion with X;

wherein X has, upon complexing with the metal ion, a specific regional secondary structure forming at least a part of the global secondary structure;

wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained secondary structure; and wherein the conformationally constrained secondary structure comprising at least a part of X, $R_1$ or $R_2$ comprises a ligand capable of forming a member of a ligand and receptor pair.

The structure may also include a metal ion, as described in the formula given immediately above, complexed to X. Upon complexation of the metal ion, X may form a specific regional secondary structure which is a reverse turn structure.

In the formula given immediately above, X may include amino acids each containing at least one nitrogen, sulfur or oxygen atom available for complexing with the available valences of the metal ion. If less than all of the valences of the metal ion are otherwise satisfied upon complexation of the metal ion with the amino acids contained in X, then X may also include a derivatized amino acid or spacer sequence, which derivatized amino acid or spacer sequence includes at least one nitrogen, sulfur or oxygen atom available for complexing with the available valences of the metal ion, so that all of the valences of the metal ion are satisfied upon complexation of the metal ion with X.

The peptide may also be a cyclic peptide of the formula:

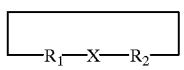

wherein $R_1$ and $R_2$ are covalently linked together. In such case, R1 and $R_2$ may be covalently linked together through an amide, disulfide, thioether, thioester, urethane, or ester linkage. The covalent linkage between $R_1$ and $R_2$ may also be a linkage through the end groups of $R_1$ and $R_2$, linkage through side chain functionalities of any amino acid within $R_1$ and $R_2$, linkage through the end group of $R_1$ and a side chain functionality of any amino acid in $R_2$, or linkage through the end group of $R_2$ and a side chain functionality of any amino acid in $R_1$.

The peptide may also be a cyclic peptide of the formula:

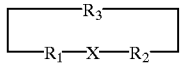

wherein $R_1$ and $R_2$ are as defined above, and $R_3$ comprises from 1 to about 20 amino acids. In this instance, $R_3$ may form a part of the conformationally constrained secondary structure.

RGD-Receptor Mimics. Peptides of this invention may be manufactured peptides and pharmaceutically acceptable salts thereof containing a metal ion-binding backbone including two or more contiguous amino acids available for complexing with a metal ion, and a biological-function domain specific for receptors to the tripeptide sequence Arg-Gly-Asp, which biological-function domain is conformationally constrained upon complexing the metal ion-binding backbone with a metal ion. In such case, the peptide may be of the formula:

$R_1$-Aaa-Bbb-Ccc-Ddd-$R_2$, $R_1$-Bbb-Aaa-Ccc-Ddd-$R_2$, $R_1$-Bbb-Ddd-Ccc-Aaa-$R_2$, or $R_1$-Ddd-Bbb-Ccc-Aaa-$R_2$ wherein
- Aaa is an L- D-isomer of an amino acid with a positively charged side chain, and containing a nitrogen which can be available for binding a metal ion;
- Bbb is an L- or D-isomer of an amino acid with one or more uncharged side chains;
- Ccc is an L- or D-isomer of an amino acid containing a sulfur and a nitrogen or containing two nitrogens which can be available for binding a metal ion;
- Ddd is an L- or D-isomer of a neutral amino acid with a free α-carboxyl group or an amino acid with a negatively charged functional group in its side chain;
- $R_1$ is H, alkyl, aryl, alkylcarbonyl, arylcarbonyl, alkyloxycarbonyl, aryloxycarbonyl, or a polymer attached directly or through a carbonyl group; and
- $R_2$ is, if Ddd is other than a neutral amino acid with a free α-carboxyl group, an amide, substituted amide or ester.

Ddd may be Gly, Ala, β-Ala, N-Me-β-Ala, or a higher homologue of β-Ala.

Representative examples of peptides of the general formulas include:

Arg-Gly-Cys-β-Ala,  <SEQ ID NO: 1>

D-Arg-Gly-Cys-β-Ala,

Arg-Gly-D-Cys-β-Ala,

D-Arg-Gly-D-Cys-β-Ala,

D-Lys-Gly-Cys-β-Ala,

D-Lys-Gly-Cys-Gly,

Gly-Arg-Cys-β-Ala,  <SEQ ID NO: 2>

Gly-D-Arg-Cys-β-Ala,

Gly-Arg-D-Cys-β-Ala,

Gly-D-Arg-D-Cys-β-Ala,

D-Arg-D-Phe-D-Cys-β-Ala, $C_6H_5$-$CH_2$-CO-D-Arg-Gly-D-Cys-β-Ala, and

Phe-Arg-D-Cys-β-Ala.

It is also possible to construct peptides with a conformationally constrained biological-function domain specific for receptors to the tripeptide sequence Arg-Gly-Asp, but not necessarily of the general formulas given above, such as:

D-Arg-Gly-D-Cys,

Arg-Gly-D-Cys,

HOOC-$(CH_2)_2$-CO-Phe-Gly-Cys-Arg,

HOOC-$(CH_2)_4$-CO-Gly-Lys-Cys, and

HOOC-$(CH_2)_5$-CO-Gly-Lys-Cys.

These peptides may have the metal ion-binding backbone complexed with a gamma-emitting metal ion, and may be used for imaging of thrombosis, cancer, sites of inflammation or atherosclerotic plaque. These peptides may also have the metal ion-binding backbone is complexed with a non-radioactive metal ion, and may be used as a therapeutic agent for myocardial infarction, thrombosis, restinosis, angiogenesis, bone resorption or metastatic cancer.

Tuftsin Mimics. Peptides of this invention may be manufactured peptides and pharmaceutically acceptable salts thereof containing a metal ion-binding backbone including two or more contiguous amino acids available for complexing with a metal ion, and a biological-function domain specific for the tuftsin receptor, which biological-function domain is conformationally constrained upon complexing the metal ion-binding backbone with a metal ion. The peptides may be of the formula:

$R_1$-Aaa-Bbb-Ccc-Ddd-Eee-$R_2$ wherein
- Aaa is a L- or D-isomer of an amino acid with a neutral or hydrophilic side chain;
- Bbb is an L- or D-isomer of an amino acid with a positively charged side chain containing a nitrogen which can be available for binding a metal ion;
- Ccc is an L- or D-isomer of an amino acid with an uncharged side chain and containing a nitrogen which can be available for binding a metal ion;
- Ddd is an L- or D-isomer of an amino acid containing a sulfur, a sulfur and a nitrogen, or two nitrogens which can be available for binding a metal ion;
- Eee is an L- or D-isomer of an amino acid with a positively charged side chain;
- $R_1$ is H, alkyl, aryl, alkylcarbonyl, arylcarbonyl, alkyloxycarbonyl, aryloxycarbonyl, or a polymer attached directly or through a carbonyl group, unless Aaa is a des-amino amino acid, in which case $R_1$ does not exist; and
- $R_2$ is an amide, substituted amide, ester, or a polymer unless Eee is a des-carboxyl amino acid, in which case $R_2$ does not exist.

Aaa may be Thr, Cys, Pen, Pro, Ser or a corresponding des-amino derivative. Representative peptides include Thr-D-Lys-Gly-D-Cys-Arg, Thr-D-Lys-Gly-D-His-Arg and Pro-D-Lys-Gly-D-Cys-Arg.

The metal ion-binding backbone may be complexed with a gamma-emitting metal ion, and the peptide used for diagnostic imaging of sites of infection or inflammation. The peptide may also be used as an immunostimulatory agent, and may in such instances be complexed with a metal ion which is not radioactive.

Cyclic Peptides. This invention also includes cyclic peptide, and pharmaceutically acceptable salts thereof, with a metal ion-binding backbone for isosteric replacement of a disulfide, thioether, lactam, or a lactone bridge, the cyclic peptide being of the general formula:

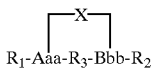

wherein X is a complexing backbone for complexing metal ion comprising a plurality of amino acids, so that substantially all of said valences of the metal ion are satisfied upon complexation of the metal ion with X, wherein $R_1$ and $R_2$ each comprise from 0 to about 20 amino acids, wherein $R_3$ comprises from 1 to about 20 amino acids, wherein Aaa and Bbb each comprise an amino acid connected to X through a disulfide, amide, thioether, thioester, urethane or ester bond. The peptide may also include a metal ion complexed to X. X may, in these cyclic peptides, include amino acids containing at least one nitrogen, sulfur or oxygen atom available for complexing with the available valences of the metal ion. If less than all of the valences of the metal ion are otherwise satisfied upon complexation of the metal ion with the amino acids comprising X, then X may also include a derivatized amino acid or spacer sequence, which derivatized amino acid or spacer sequence comprises at least one nitrogen, sulfur or oxygen atom available for complexing with the available valences of the metal ion, so that all of the valences of the metal ion are satisfied upon complexation of the metal ion with X.

X may be an amino acid sequence of the formula:

Ccc-Ddd-Eee or Eee-Ddd-Ccc, wherein each of Ccc and Ddd is an amino acid or dipeptide with uncharged side chains, and wherein Eee is a L- or D-isomer of Cys, HomoCys, Pen, or His. Aaa may be a L- or D-isomer of an amino acid with a carboxyl group or an amine group in its side chain. Bbb may be a L- or D-isomer of an amino acid with a side chain with a carboxyl group or an amino group, such that if Bbb has a side chain with a carboxyl group, Aaa has a side chain with an amino group, and if Bbb has a side chain with an amino group, Aaa has a side chain with a carboxyl group.

The cyclic peptides of the general formula given immediately above include a somatostatin analogue of the formula:

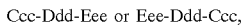

wherein X contains L- or D-isomers of Gly-Gly-Gly-Cys, Gly-Gly-Cys, Gly-Gly-Gly-His, or Gly-Gly-His.

The cyclic peptides of the general formula given immediately above also include melanotropin analogues of the formulas:

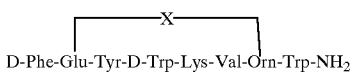

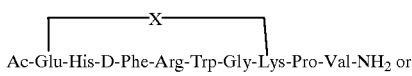

wherein X contains L- or D-isomers of Gly-Gly-Gly-Cys<SEQ ID NO: 3>, Gly-Gly-Cys, Gly-Gly-Gly-His <SEQ ID NO: 4>, or Gly-Gly-His.

Method of Making. This invention includes a method of making a peptide and pharmaceutically acceptable salts thereof with a conformationally constrained secondary structure obtained upon complexing with a metal ion, which method includes the steps of:

a) providing a peptide of the general formula:

$R_1$—X—$R_2$ wherein X is a complexing backbone for complexing metal ion comprising a plurality of contiguous amino acids, so that substantially all of said valences of the metal ion are satisfied upon complexation of the metal ion with X, wherein X has, upon complexing with the metal ion, a specific regional secondary structure forming a part of the secondary structure, and wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained secondary structure; and b) complexing a metal ion to the peptide.

This invention also includes a method of making a peptide or pharmaceutically acceptable salts thereof that includes a conformationally constrained secondary structure forming at least a part of a ligand capable of forming a member of a ligand and receptor pair, the method comprising the steps of:

a) providing a peptide of the general formula:

$R_1$—X—$R_2$ wherein X is a complexing backbone for complexing metal ion comprising a plurality of amino acids, so that substantially all of said valences of the metal ion are satisfied upon complexation of the metal ion with X, wherein X has, upon complexing with the metal ion, a specific regional secondary structure forming a part of the conformationally constrained secondary structure, wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained global secondary structure, and wherein the conformationally constrained global secondary structure comprising at least a part of X, $R_1$ or $R_2$ comprises a ligand capable of forming a member of a ligand and receptor pair; and b) complexing a metal ion to the peptide;

whereby the metal ion causes X to form a specific regional secondary structure, thereby causing the peptide to be configured as a conformationally constrained secondary structure comprising a ligand capable of forming a member of a ligand and receptor pair. The affinity of the conformationally constrained secondary structure forming at least a part of a ligand for its receptor will generally be substantially higher than the affinity of the peptide which is not conformationally constrained in a global secondary structure with a metal ion.

This invention further includes a method of making a peptide or a pharmaceutically acceptable salt thereof that includes an amino acid sequence which mimics a biological-function domain, the method including the steps of:

a) providing a complexing backbone for complexing a metal ion comprising a plurality of amino acids, said amino acids being selected so that substantially all of the valences of the metal ion are satisfied upon complexation of the metal ion with the complexing backbone, which complexing backbone is coextensive with at least a portion of the biological-function domain upon complexing of the complexing backbone with a metal ion;

b) providing from 0 to about 20 amino acids linked to either end of the complexing backbone, which amino acids comprise the remainder of the biological-function domain upon complexing of the complexing backbone with a metal ion; and c) complexing the complexing backbone with a metal ion.

In this method, at least some of the amino acids making up the complexing backbone of amino acids may include side chains modified to increase the homology of the complexing backbone with at least a portion of the biological-function domain upon complexing of the complexing backbone with a metal ion.

Upon complexing the complexing backbone with a metal ion, the complexing backbone may form a specific regional secondary structure. In such case, the specific regional secondary structures may further cause the peptide to be configured with a conformationally constrained secondary structure.

Pharmaceutical Applications. Included in this invention are peptide-based pharmaceutical compositions which include a peptide containing a metal ion-binding backbone and a determined biological-function domain, which biological-function domain is conformationally constrained upon complexing the metal ion-binding backbone with a metal ion, and a metal ion. In such pharmaceutical preparations, at least a portion of the peptide may be conformationally constrained in a secondary structure upon complexing the metal ion-binding backbone with the metal ion. The biological-function domain may further be substantially inactive until the metal ion-binding backbone is complexed with a metal ion.

Metallopeptide Libraries. This invention also includes a method of obtaining a metallopeptide having a desired target property from a library of metallopeptides, which method includes the steps of:

a) providing a mixture of candidate peptides, each peptide including a metal ion-binding backbone with two or more contiguous amino acids available for complexing with a metal ion, and which metal ion-binding backbone is conformationally constrained upon complexing the metal ion-binding backbone with a metal ion, each peptide further including distinct, unique and different amino acid sequences, wherein the presence of each peptide in the mixture is predetermined;

b) complexing the metal ion-binding backbone of the peptides with a metal ion; and c) selecting from among the mixture of candidate metallopeptides a metallopeptide having a desired target property by exposing the mixture of candidate metallopeptides to a substance to which a metallopeptide with the desired target property will preferentially bind.

Here, and in other methods relating to metallopeptide libraries, a metallopeptide having a desired property may conveniently be selected by using bioassays, biochemical assays, pharmacological assays, physiochemical assays or similar assays. Such assays may either directly or indirectly determine that a metallopeptide has a desired property, or may determine some parameter relating to the desired property.

The method further may include isolating the selected candidate metallopeptide having the desired target property. If necessary, as for example with soluble libraries, a number of methods known in the art may be employed to determine either the amino acid composition or structure of the metallopeptide having the desired property. The mixture of candidate peptides may be bound to a solid phase resin, such that only one specific peptide is bound to each resin particulate, or may be in solution.

An alternate method of obtaining a metallopeptide having a desired target property includes the steps of:

a) providing known combinations of two, three or four contiguous amino acids making up at least a part of a metal ion-binding backbone wherein each amino acid is available for complexing with a metal ion, and further wherein the metal ion-binding backbone is conformationally constrained upon complexing the metal ion-binding backbone with a metal ion;

b) adding distinct, unique and different amino acid sequences, each sequence comprising one or more amino acids, to the amino acids making up the metal ion-binding backbone, wherein the presence of each peptide in the mixture is predetermined;

c) complexing the metal ion-binding backbone of the peptides with a metal ion; and d) selecting from among the mixture of candidate metallopeptides a metallopeptide having a desired target property by exposing the mixture of candidate metallopeptides to a substance to which a metallopeptide with the desired target property will preferentially bind.

The method further may include isolating the selected candidate metallopeptide having the desired target property. The mixture of candidate peptides may be bound to a solid phase resin, such that only one specific peptide is bound to each resin particulate, or may be in solution.

The contiguous amino acids making up the metal ion-binding backbone may each contain one or more nitrogen, sulfur or oxygen atoms available for complexing with the available valences of the metal ion.

A method of obtaining a metallopeptide having a desired biological-function domain includes the steps of:

a) providing known combinations of two, three or four contiguous amino acids making up at least a part of a metal ion-binding backbone wherein each amino acid is available for complexing with a metal ion, and wherein the metal ion-binding backbone is conformationally constrained upon complexing the metal ion-binding backbone with a metal ion;

b) adding distinct, unique and different amino acid sequences, each sequence made up of one or more amino acids, to the contiguous amino acids making up a metal ion-binding backbone, wherein the presence of each peptide in the mixture is predetermined;

c) complexing the metal ion-binding backbone of the peptides with a metal ion; and d) selecting from among the mixture of candidate metallopeptides a metallopeptide having a desired biological-function domain by exposing the mixture of candidate metallopeptides to a substance to which a peptide with the desired biological-function domain will preferentially bind.

The method may further include isolating the selected candidate metallopeptide having the desired biological-function domain. The mixture of candidate peptides may be bound to a solid phase resin, such that only one specific peptide is bound to each resin particulate, or may be in solution.

The contiguous amino acids making up the metal ion-binding backbone may each contain one or more nitrogen, sulfur or oxygen atoms available for complexing with the available valences of the metal ion.

Objects of the Invention. It is one object of this invention to devise, demonstrate and illustrate making and using highly specific conformational restrictions in peptides, peptoids, related pseudopeptides, peptidomimetics and metallo-constructs by complexing sequences thereof to a desired metal ion so that the topography of the side chains in the resulting complex is a biologically active three-dimensional structure which binds to a known biological receptor.

Another object of this invention is to employ this approach to obtain radiolabeled molecules in a carrier-free state, so that only metal ion complexed molecules are biologically active, for radioimaging, radiation therapy, positron emission tomography (PET) and the like.

Another object of this invention is to provide a method for designing a series of molecular moieties, each capable of complexing a metal ion in a specific manner as a replacement for a disulfide, a lactam, or a lactone bridge in a peptide, whereby there is conformational restriction in a peptide-related segment upon complexation with the metal ion. The topography of the side chains of the biological-function domain in the metal ion complexed molecule resembles that of the corresponding disulfide-, lactam-, or lactone-containing peptide congener.

Another object of this invention is to provide peptide-metal ion complexes which have a higher level of stability and are less susceptible to proteolysis than either the peptide not complexed to a metal ion, or art-conventional peptides.

Another object of this invention is to provide for peptide analogues which lack conformational restriction if not complexed with a metal ion, so that the uncomplexed peptide analogue is either inactive or demonstrates low potency, but which have high potency and concomitant conformational restriction upon complexation with a metal ion, including a radiometal ion.

Another object of this invention is to provide conformationally constrained peptide-metal ion complexes as surrogates for reverse turn structures, such as beta turns and gamma turns commonly found in naturally occurring peptides and proteins, whereby the turns formed as a consequence of metal ion complexation are more stable than the naturally occurring turn structures, which are stabilized only by weaker interactions such as van der Waals' interactions and hydrogen bonds.

Another object of this invention is to utilize metal complexation in a peptide to cause specific regional conformational restrictions in the peptide so that the peptide conformation at the metal binding site is conformationally fixed upon metal complexation.

Another object of this invention is to utilize metal ion complexation in a peptide to effect specific global conformational restrictions in the peptide so that the regional conformational restrictions caused by complexing metal ion to a sequence including amino acid residues in turn cause conformational restriction on distal regions of the peptide.

Another object of this invention is to utilize metal ion complexation in a linear peptide to fold and conformationally restrict the peptide to obtain conformational restriction comparable to that obtainable by cyclizing the peptide through a disulfide, lactam or similar group.

Another object of this invention is to complex a peptide to a metal ion so as to alter the in vivo biodistribution profile, rate and mode of clearance from the body, bioavailability and pharmacokinetics in mammals.

Another object of this invention is to provide peptide-metal ion complexes which utilize stable and non-radioactive metal ions, with the biological-function domain having specific biological activity, such as for therapeutic treatment of disease.

Another object of this invention is to design and develop a molecule which, upon complexing with a metal ion, includes a biological-function domain which is specific for one or more of the RGD-binding integrin family of receptors for use in diagnostics and therapeutic modalities, including thrombus imaging, imaging kidney damage, imaging and therapy of tumor lesions and imaging and therapy of myocardial infarction.

Another object of this invention is to design and develop a molecule which, upon complexing with a metal ion, includes a biological-function domain which is specific for tuftsin receptors, and which stimulates polymorphonuclear granulocytes, monocytes and macrophages towards phagocytosis and may be used in diagnostic modalities for abscess and infection imaging.

Another object of this invention is to provide a peptide-metal ion complex with a region specific for the tuftsin receptor on polymorphonuclear granulocytes and macrophages, the presence of which complex increases the antigenic profile of antigens presented to such polymorphonuclear granulocytes and macrophages, thereby resulting in production of higher titer antibodies.

Another object of this invention is to design and develop a somatostatin analogue wherein the disulfide bond in somatostatin is substituted by a specific metal ion-complexing moiety, so that after complexation of a metal ion to the moiety, the topography of the receptor binding region is fixed and is similar to that in the original disulfide-containing somatostatin molecule.

Another object of this invention is to displace a lactam bridge in a potent melanotropin analogue containing a cyclic lactam bridge by a specific metal ion-binding moiety so that the molecule is potent, and binds to a designated receptor, only after complexation of the metal ion.

Another object of this invention is to develop a peptide-metal ion ligand for the estrogen receptor by de novo design so that the ligand binds the estrogen receptor only after its complexation with a metal ion.

Another object of this invention is to complex peptides with radiometal ions for use in whole body imaging and radiotherapy so that the resulting peptide-metal ion complex is of higher affinity and specificity for the tissue target than the uncomplexed peptide molecule. The resulting radiolabeled species therefore is essentially carrier-free in terms of biological target recognition.

Another object of this invention is to provide peptide-metal ion complexes which can transit the brain-blood barrier and hence may be adapted for use in treating or diagnosing conditions of the brain.

Another object of this invention is to provide peptide-metal ion complexes which can transit the gut-blood barrier, without significant enzymatic or peptidase degradation, and hence may be adapted for use by oral administration.

Another object of this invention is to provide combinatorial and peptide libraries of peptide-metal ion complexes, wherein the peptides include a metal ion-binding domain, such that a specific conformational restriction is obtained upon labeling the peptides with a metal ion.

Another object of this invention is to provide metallopeptide libraries, wherein the metallopeptides include a metal ion-binding domain, such that a specific conformational restriction is obtained upon labeling the peptides with a metal ion, and the metallopeptides further include known but distinct, unique and different amino acid sequences.

Another object of this invention is to provide metallopeptide libraries, wherein the metallopeptides include a metal ion-binding domain and known but distinct, unique and different amino acid sequences, wherein the metallopeptides may be exposed to a substance to which a metallopeptide with the desired target property will preferentially bind.

Another object of this invention is to provide metallopeptide libraries, wherein the metallopeptides include a metal ion-binding domain and known but distinct, unique and different amino acid sequences, wherein the metallopeptides may be exposed to a substance to which a metallopeptide with the biological-function domain will preferentially bind.

Another object of this invention is to provide metallopeptide libraries, wherein the metallopeptides include a metal ion-binding domain, which may be either soluble or solid phase libraries.

Another object of this invention is to provide a non-peptidic metallo-construct, which upon complexing with a metal ion has a high degree of conformational restriction, and can be utilized in the manner disclosed for peptide-metal ion complexes.

Other objects, advantages and novel features, and further scope of applicability of the present invention will be set forth in part in the detailed description to follow and in part will become apparent to those skilled in the art upon examination of the following, or may be learned by practice of this invention. The objects and advantages of this invention may be realized and attained by means of the instrumentalities and combinations particularly pointed out in the appended claims.

BRIEF DESCRIPTION OF THE DRAWINGS

FIG. 1-A depicts a naturally occurring reverse turn structure, such as a portion of a larger peptide or protein wherein the reverse turn is located between two anti-parallel β-sheets. FIG. 1-B schematically depicts a peptide of this invention with random conformation, which is not complexed with a metal ion. FIG. 1-C depicts a peptide of this invention which is complexed with a metal ion. This complexation forms a reverse turn structure, yielding a highly constrained structure.

FIGS. 2-A and 2-B show the two isomers created by the isomerism in the metaloxo group. FIG. 2-C shows the figures of FIGS. 2-A and 2-B superimposed, demonstrating that there is no difference in topography of the biologically relevant amino acid side chains between the two isomers.

FIGS. 3-A and 3-B show the two isomers created by the isomerism in the metaloxo group. FIG. 3-C shows the figures of FIGS. 3-A and 3-B superimposed, demonstrating that there is no difference in topography of the biologically relevant amino acid side chains between the two isomers.

Figure 1A:
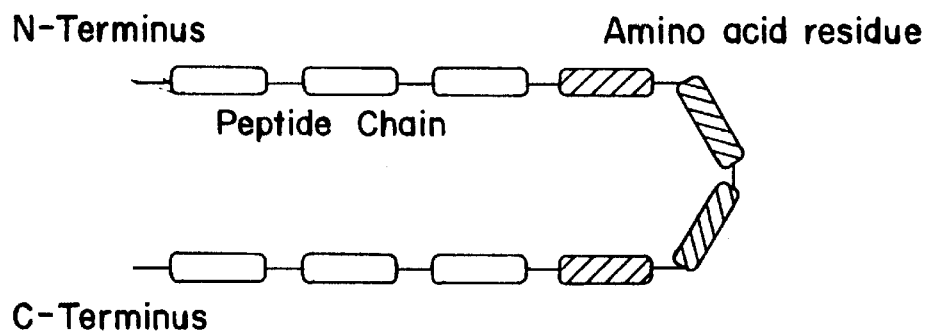
FIG. 1 schematically depicts a linear peptide made by this invention, both prior to complexing with a metal ion wherein it is not conformationally constrained, and after complexing with a metal ion wherein it is conformationally constrained.

DETAILED DESCRIPTION OF THE PREFERRED EMBODIMENTS OF THE INVENTION (BEST MODES FOR CARRYING OUT THE INVENTION)

Using the methods of this invention, peptide-metal ion complexes are designed by selecting a peptide chain which encompasses the groups that individually are necessary for providing a coordination site for complexation with a metal ion. Specific stereochemical features of this peptide-metal ion complex are due to the stereochemistry of the coordination sphere of the complexing metal ion. Thus the defined geometry of the coordination sphere of the incoming metal ion dictates and defines the nature and extent of the conformational restriction imposed on the peptide backbone.

While it is known that a complexing metal ion can nucleate a particular conformational preference in a peptide chain, and this approach has been demonstrated to cause the formation of a tertiary structure from the existing domains of the secondary structure, utilization of metal complexation to force conformational restriction so as to induce a preferential secondary structure that is relevant to a given biological receptor has heretofore remained unexplored. This approach presents significant advantages, because shorter peptides do not generally exhibit preferred solution conformation, and generally are characterized by substantial segmental flexibility. For peptides in which secondary structure is important, such as short peptides containing sequences which bind to biological receptors, some form of chemical modification is required to decrease conformational flexibility.

Definitions. Certain terms as used throughout the specification and claims are defined as follows:

The terms "bind," "binding," "label", "labeling", "complex," and "complexing," as used throughout the specification and claims, are generally intended to cover all types of physical and chemical binding, reactions, complexing, attraction, chelating and the like.

The peptides of this invention can be:

a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like.

The term "peptide" as used throughout the specification and claims is intended to include any structure comprised of two or more amino acids, including derivatives of amino acids. For the most part, the peptides of this invention comprise fewer than 100 amino acids, and preferably fewer than 60 amino acids, and most preferably ranging from about 2 to 20 amino acids. The amino acids forming all or a part of a peptide may be naturally occurring amino acids, isomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W. H. Freeman & Co., New York, 1992, the teachings of which are incorporated herein by reference, including the text and table set forth at pages 11 through 24. The term "amino acid" also includes isomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: Emerging approaches in the molecular design of receptor-selective peptide ligands; conformational, topographical and dynamic consideration. *Biochem J* 268:249–262, 1990; and Toniolo C: Conformationally restricted peptides through short-range cyclization. *Int J Peptide Protein Res* 35:287–300, 1990; the teachings of all of which are incorporated herein by reference. A single amino acid is sometimes referred to herein as a "residue."

The peptide constructs of this invention also include a metal ion, and for embodiments in which the metal ion is used diagnostically or therapeutically, a medically useful metal ion. The metal ion may, but need not, be radioactive, paramagnetic or superparamagnetic. The metal ion can be an ionic form of the elements iron, cobalt, nickel, copper, zinc, manganese, arsenic, selenium, technetium, ruthenium, palladium, silver, cadmium, indium, antimony, rhenium, osmium, iridium, platinum, gold, mercury, thallium, lead, bismuth, polonium and astatine. The metal ion can also be an ionic radionuclide of indium, gold, silver, mercury, technetium, rhenium, tin, astatine and copper.

A radioactive medically useful metal ion may generate gamma rays, beta particles, or positrons which are converted into gamma rays upon collision with electrons. The medically useful metal ion may be used in diagnostic imaging procedures including gamma scintigraphy, specific photon emission computerized tomography, or positron emission tomography. The medically useful metal ion may also be used diagnostically in magnetic resonance imaging. Medically useful metal ions may also be used therapeutically.

The type of medically useful metal ion depends on the specific medical application. Particularly useful metal ions include elements 25–30 (Mn, Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi.

The biological-function domain of the peptide is defined in the specification and claims as a sequence of one or more amino acids which constitute a biologically active peptide sequence, exhibiting binding to a biological receptor found on cells, tissues, organs and other biological materials. The biological-function domain also includes any sequence, which may be consecutive amino acids (sychnological) or may be non-consecutive amino acids (rhegnylogical), of one or more amino acids which forms a ligand, which ligand is capable of forming a specific interaction with its acceptor or receptor. The term "receptor" is intended to include both acceptors and receptors. The receptor may be a biological receptor. The peptide or the biological-function domain may transmit a signal to the cells, tissues or other materials associated with the biological receptor after binding, but such is not required. Examples include, but are not limited to, biological-function domains specific for hormone receptors, neurotransmitter receptors, cell surface receptors, enzyme receptors and antibody-antigen systems. The biological-function domain may thus be either an agonist or antagonist, or a mixed agonist-antagonist. The biological-function domain may also include any ligand for site specific RNA or DNA binding, such as sequences which may be employed as mimics of transcription and other gene regulatory proteins. The biological-function domain may also include any sequence of one or more amino acids, or other constrained molecular regions, which exhibit binding to a biological receptor found on other peptides, on enzymes, antibodies, or other compositions, including proteinaceous compositions, which may themselves exhibit binding to another biological receptor. The biological-function domain may also constitute a member of a "specific binding pair," wherein a specific binding pair comprises at least two different molecules, where one molecule has an area on the surface or in a cavity which specifically binds to a particular spatial and polar organization of the other molecule. Frequently, the members of a specific binding pair are referred to as ligand and receptor or anti-ligand. Examples of specific binding pairs include antibody-antigen pairs, hormone-receptor pairs, peptide-receptor pairs, enzyme-receptor pairs, carbohydrate-protein pairs (glycoproteins), carbohydrate-fat pairs (glycolipids), lectin-carbohydrate pairs and the like.

The biological-function domain is further defined to include the portion of a construct, wherein the construct is a peptidomimetic, peptide-like, or metallo-construct molecule, which upon binding of the construct with a metal ion, is biologically active, exhibiting binding to a biological receptor found on cells, tissues, organs and other biological materials. This biological-function domain may, in this instance, be sychnological or rhegnylogical, and generally has the attributes and functions of a biological-function domain of a peptide. The biological-function domain may be coextensive with all or a portion of the metal ion-binding domain, so that the same amino acids which constitute the metal ion-binding domain also constitute all or a part of the the biological-function domain. In many instances, one or amino acids of the metal ion-binding domain will also be part of the biological-function domain, and one or more additional amino acids, which are not part of the metal ion-binding domain, form the remainder of the biological-function domain.

Conformational constraint refers to the stability and preferred conformation of the three-dimensional shape assumed by a peptide or other construct. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. See generally *Synthetic Peptides: A User's Guide*, cited above.

The primary structure of a peptide is its amino acid sequence. The secondary structure deals with the conformation of the peptide backbone and the folding up of the segments of the peptide into regular structures such as α-helices, β-sheets, turns and the like. Thus, the three-dimensional shape assumed by a peptide is directly related to its secondary structure. See generally *Synthetic Peptides: A User's Guide*, cited above, including the text, figures and tables set forth at pages 24–33, 39–41 and 58–67. A global structure refers to a peptide structure which exhibits a preference for adopting a conformationally constrained three-dimensional shape.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Coordination of Metal Ions. The coordination sphere of various common metal ions, in general, is tetradentate to hexadentate. In one embodiment according to this invention, a peptide is designed so that, in addition to the required chemical groups that are required for receptor recognition, it also contains the desired number of groups (four to six in most cases) for forming a bond with the metal ion. The molecule is designed so that, upon labeling with a metal ion, its conformation is fixed so that affinity for the receptor is achieved. The molecules are conveniently designed de novo by the help of three-dimensional molecular modeling computer software, such as the program called ALCHEMY-III (Tripos Associates Inc., St. Louis, Mo.). One basic approach to design is to construct a peptide backbone complexed to the metal ion so that all its valences are satisfied while preserving the coordination geometry defined by that particular metal ion. This gives rise to a molecular scaffold of a metal-peptide backbone, which is then modified with functional groups that are specific for the biological target. In particular, the amino acid side chains required for receptor recognition and binding are assigned to appropriate amino acid residues on the scaffold in a manner such that the spatial relationship between these side chains matches that which has been reported or proposed previously in the scientific literature for that class of ligands, or as is found in databases, such as the protein data bank maintained by Brookhaven National Laboratory. In general, it is now possible to determine the influence and relative importance of specific amino acid residues on receptor or antigen binding, using such tools as magnetic resonance spectroscopy and molecular modeling, allowing the specific design and synthesis of peptides which bind a known antigen, antibody or receptor, or which mimic a known binding sequence or ligand.

Figure 1B:
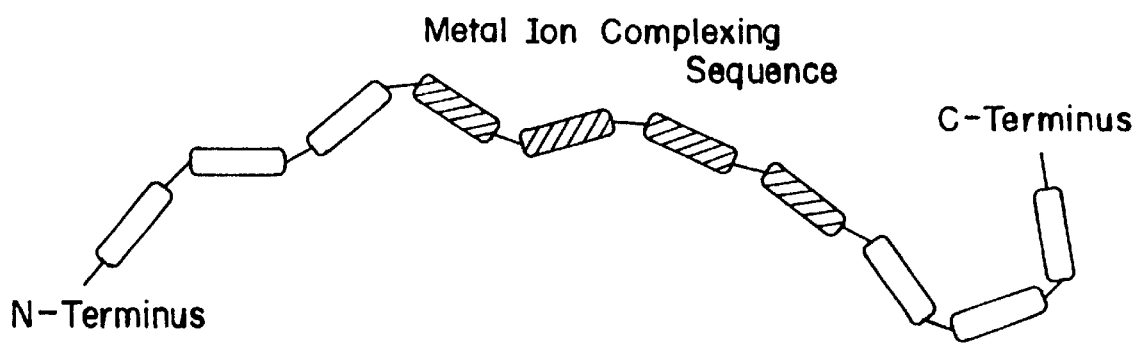
Figure 1C:
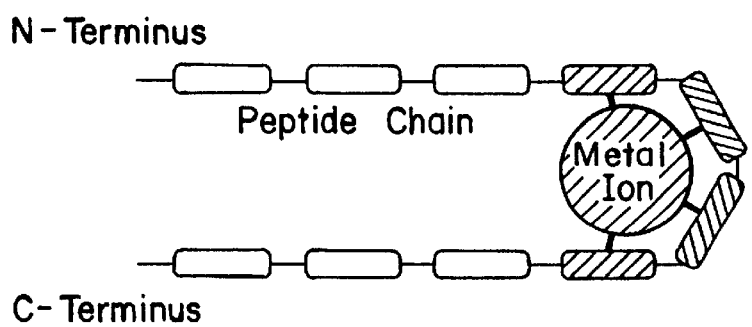

A metal ion with coordination number 4, 5 or 6, and complexing respectively with a tetra, penta, or hexadentate ligand, will fold and constrain the ligand. A highly flexible molecule like a peptide, in other words, is folded to form a kind of reverse turn upon its complexation with a metal ion. This resulting turn is a highly constrained structure in the conformational sense. FIG. 1 schematically depicts a linear peptide made by this invention, both prior to complexing with a metal ion wherein it is not conformationally constrained, and after complexing with a metal ion wherein it is conformationally constrained. FIG. 1-A depicts a naturally occurring reverse-turn structure, such as a portion of a larger peptide or protein wherein the reverse turn is a stable structure located between two anti-parallel β-sheets. Thus in FIG 1-A, additional amino acid sequences are joined to either terminus, but not included in the schematic depiction. FIG 1-B schematically depicts a peptide of this invention, which is not complexed with a metal ion. Such a peptide is not structurally constrained, and thus each amino acid of the peptide has multiple, variable three-dimensional topology with respect to any other amino acid. FIG 1-C depicts a peptide of this invention which is complexed with a metal ion. This complexation forms a reverse turn structure, yielding a highly constrained structure. The reverse turn is important to biological binding, since most biologically active peptides have been shown to display a folded structure or a reverse turn at the receptor-binding site. Most peptide hormone receptors and antibody-binding epitopes have been shown to accept a folded conformer of a peptide. This invention can thus be applied to a wide variety of ligand systems, provided that the side chains forming the receptor contact can be placed on a metal-peptide backbone scaffold, resulting, after metal ion complexation, in the highly constrained topology required by the biological receptor.

Metal-Peptide Backbone. A variety of metal ion-complexing backbones may be utilized in this invention. The selection of backbone depends, in large part, on the metal ion to be employed, the biological receptor and the size and characteristics of the biological-function domain required for the biological receptor. The preferred metal-peptide backbone is based on the requisite number of particular coordinating groups required by the coordination sphere of a given complexing metal ion. In general, most of the metal ions that may prove useful in this invention have a coordination number of four to six, and rarely as high as eight, which implies that the putative metal ion-binding peptide chain must have sufficient groups placed in the peptide chain in a stereocompatible manner so as to establish a bond with a metal ion of given geometry and coordination sphere. Coordinating groups in the peptide chain include nitrogen atoms of amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as oxime, hydrazino, sulfhydryl, phosphate, cyano, pyridino, piperidino, or morpholino groups. The peptide construct can be either linear or cyclic; however, the linear construct is generally preferred. One example of a small linear peptide is Gly-Gly-Gly-Gly, which has four nitrogens (an $N_4$ complexation system) in the backbone that can complex to a metal ion with a coordination number of four. Any similar suitable tetrapeptide could be so employed; in addition, a tripeptide in which at least one of the amino acids has a side chain with a coordinating group can be employed with a metal ion with a coordination number of four. The side chain can have a nitrogen, oxygen or sulfur-based coordination group. Thus, a tetradentate peptide construct could be $N_4$, $N_3S$, $N_2S_2$, $NS_3$, $N_2SO$ or any similar combination yielding tetradentate coordination utilizing nitrogen, sulfur and oxygen atoms. Cyclic sequences may be employed; for example, cyclo[Gly-Gly-Gly-Gly] is a simple cyclic peptide which yields an $N_4$ tetradendate ligand suitable for complexing a metal ion with a coordination number of four. Other suitable modifications to this cyclic tetrapeptide template can be structurally engineered in a manner similar to that described above for a linear peptide to convert it to any of the other tetradentate ligand systems described above.

Both linear and cyclic systems can be further modified to incorporate additional coordinating groups so that the resulting peptide is penta- or hexadentate or higher to coordinate a metal ion with higher coordination numbers. The design of such metal ion-complexing peptide sequences has been described in the scientific literature (Ozeki E, Kimura S, and Imanishi Y: *Int J Peptide Protein Research* 34:111, 1989; Garcia-Escheverria C, Albericio F, Giralt E and Pons M: *J Amer Chem Soc* 115:11663–11670, 1992; Fattoruso R, Morelli G, Lombardi A, Nastri F, Maglio O, D'Auria G, Pedone C, Pavone V: Design of metal ion binding peptides, *Biopolymers (Peptide Sci)* 37:401–410, 1995). Other examples of naturally occurring metal binding peptides include calmodulin and similar calcium binding peptides, and valinomycin, a cyclic peptide antibiotic that binds potassium.

Other complexing backbones may include at least two amino acid residues and either a derivatized amino acid or a spacer sequence, with the derivatized amino acid or spacer sequence having a nitrogen, sulfur or oxygen atom available for complexing with the valences of the metal ion. Examples of derivatized amino acids include amide, primary alkyl or aryl amide, 1,2,3,4-tetrahydroisoquinoline-2-carboxylic acid and its corresponding 7-hydroxy derivative, N-carboxymethylated amino acids, 2'-mercapto-Trp, $N^\beta$-(2 mercaptoethane)-$\alpha,\beta$-diaminopropionic acid and similar higher homologs of other homologous amino acids, $N^\beta$-(2 aminoethane)-$\alpha,\beta$-diaminopropionic acid and similar higher homologs of other homologous amino acids, $N^\beta$-(picolinoyl)-$\alpha,\beta$-diaminopropionic acid and similar higher homologs of other homologous amino acids, $\beta$-(picolylamide)-Asp and similar homologs of other homologous amino acids, $N^\beta$-(2-amino-benzoyl)-$\alpha,\beta$-diaminopropionic acid and similar higher homologs of other homologous amino acids, $\beta$-(2-amidomethylpyridine)-Asp and similar homologs of other homologous amino acids, N-benzyloxycarbonyl amino acid, N-tert butyloxycarbonyl amino acid, N-fluorenylmethyloxycarbonyl amino acid and other similar urethane-protected amino acid derivatives, and other derivatized or synthetic amino acids relating to any of the foregoing.

Examples of a spacer sequence which may be employed in this invention include 2-mercaptoethylamine, succinic acid, glutaric acid, 2-mercaptosuccinic acid, ethylenediamine, diethylenetriamine, triethylenetetraamine, tetraethylenepentaamine, glycol, polyethylene glycol, thioglycolic acid, mercaptopropionic acid, pyridine-2-carboxylate, picolylamine, 2-mercaptoaniline, 2-aminobenzoic acid, and 2-aminomethylpyridine. In general, any sequence which may be linked, directly or indirectly, to two amino acids so as to form a continuous sequence, and which has a nitrogen, sulfur or oxygen atom available for complexing with the valences of the metal ion may be employed.

For most applications, each peptide molecule will include a metal ion-complexing backbone which complexes a single metal ion. However, for certain applications, a peptide molecule may be designed with a metal ion-complexing backbone which will complex more than one metal ion. In one embodiment, the peptide sequence includes two discrete backbone segments, separated by one or more amino acid residues or other spacers, which residues or spacers may, but need not, form a part of the functional group or biological-function domain.

The metal ion-binding backbone is a peptide sequence that has a predefined stereochemistry at the chiral center, which in turn may be connected with additional residues and structural elements forming all or part of the biological-functional domain. Selection of a chiral center with predefined stereochemistry is of tremendous advantage in that it precludes the possibility of generating new chiral centers upon complexation of metal ion, that in turn may, and generally will, influence the biological activity profile of the biological-function domain. The generation of two new chiral centers, with no control on the resulting stereochemistries, is a major drawback of the heterodimeric rhenium and technetium complexes synthesized as mimetics of steroid hormone ligands by Katzenellenbogen and co-workers (Chi D Y, O'Neil J P, Anderson C J, Welch M J, and Katzenellenbogen J A: Homodimeric and heterodimeric bis(amino thiol) oxometal complexes with rhenium(V) and technetium(V): control of heterodimeric complex formation and an approach to metal complexes that mimic steroid hormones. *J Med Chem* 37:928–937, 1994).

Figure 2A:
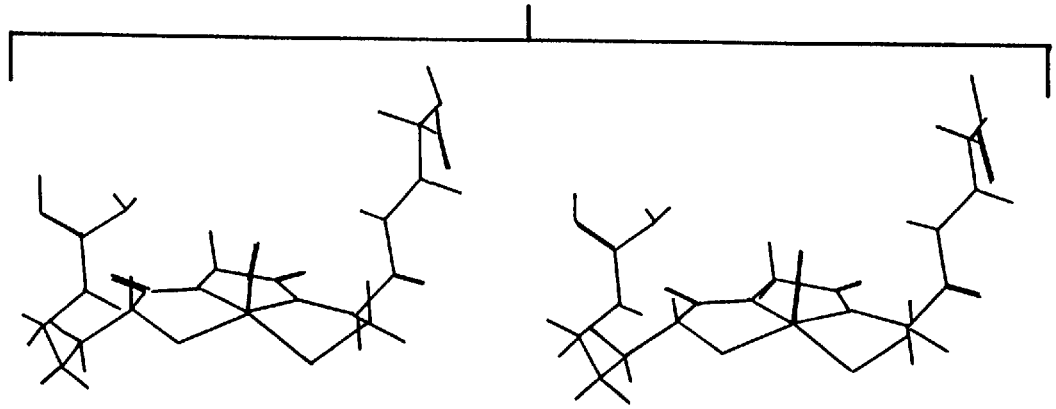
FIG. 2 shows a relaxed stereo view of a metal ion-labeled peptide of this invention with a primary unlabeled structure of D-Arg-Gly-D-Cys-β-Ala.
Figure 2B:
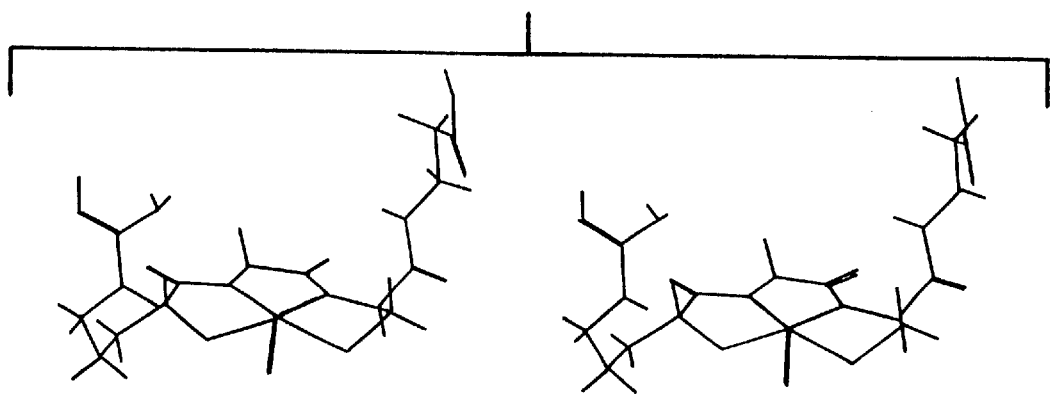
Figure 2C:
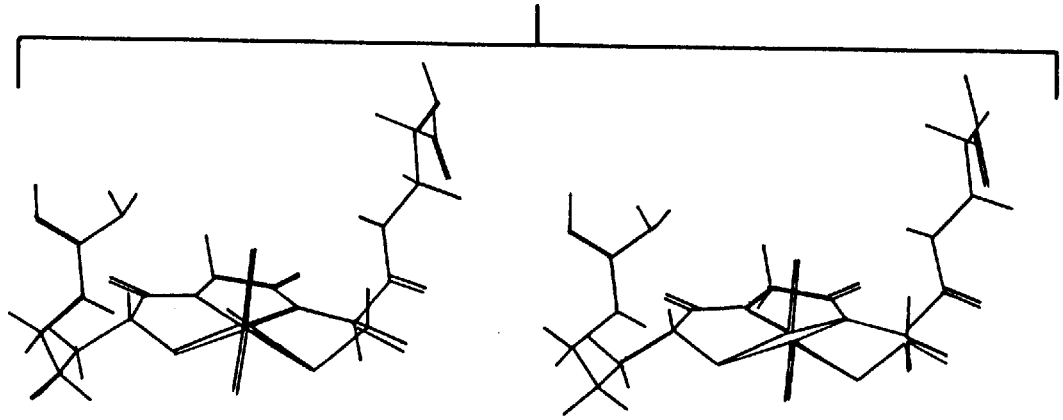
Figure 3A:
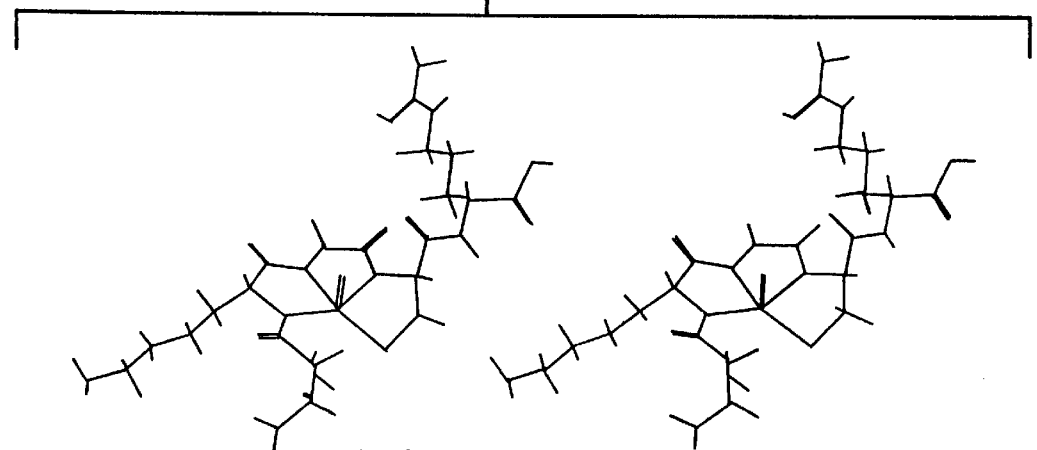
FIG. 3 shows a relaxed stereo view of a metal ion-labeled peptide of this invention with a primary unlabeled structure of Thr-D-Lys-Gly-D-Cys-Arg.
Figure 3B:
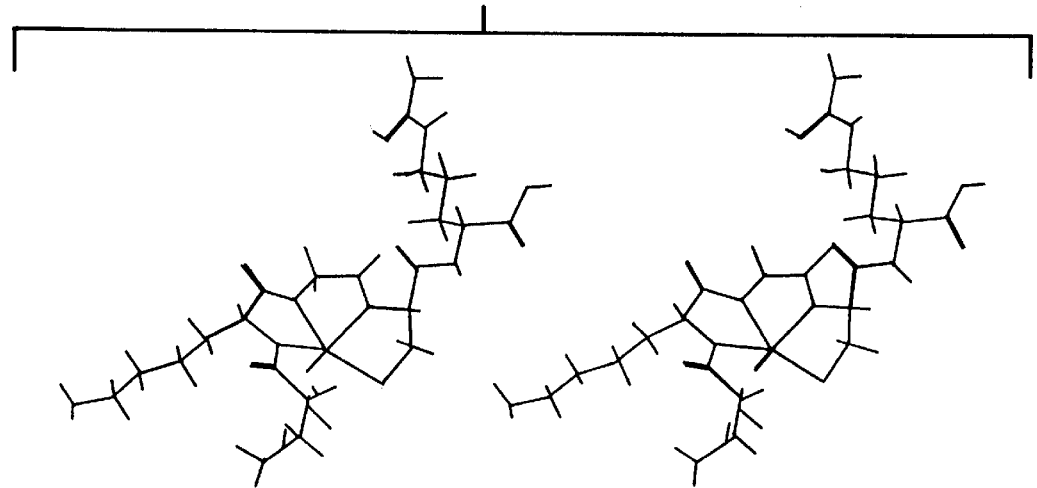
Figure 3C:
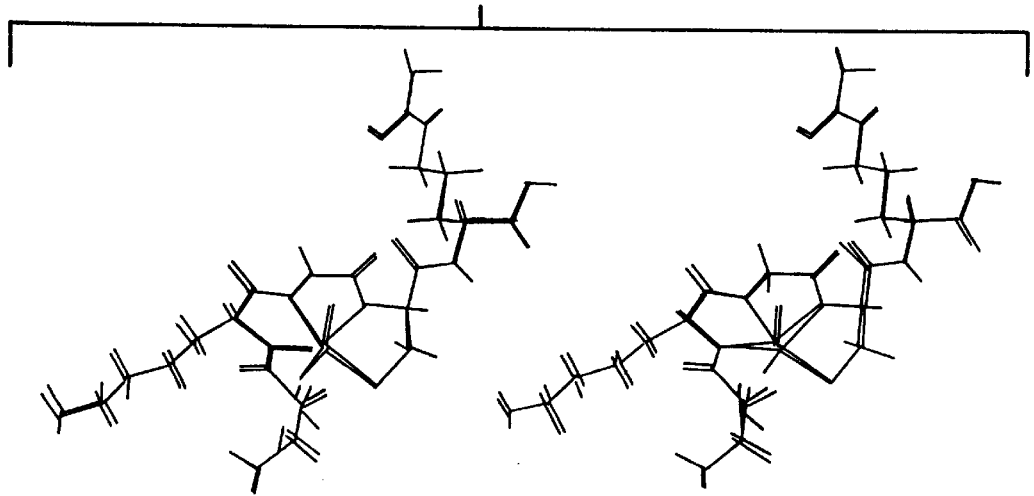

Complexation of a peptide to a metaloxo ion species, such as TcO[V] or ReO[V], can in theory lead to two isomers which differ in having either a syn- or anti-metaloxo group. The peptide-metaloxo complexes produced according to this invention may exhibit this type of syn- and anti-isomerism. These isomers are separable by HPLC and similar means in cases where an optically active amino acid also forms an integral part of the metaloxo ion-complexing part of the molecule. The orientation of the metaloxo group in either syn- or the anti-configuration does not appear to have any effect on the conformational properties of the peptide backbone complexed to the metaloxo group, as is shown in FIGS. 2 and 3, which show the syn- and anti-configuration of two different $^{99m}$Tc-labeled peptides of this invention. FIG. 2 shows a relaxed stereo view of a metal ion-labeled peptide with a primary unlabeled structure of D-Arg-Gly-D-Cys-β-Ala. FIGS. 2-A and 2-B show the two isomers created by the isomerism in the metaloxo group. FIG. 2-C shows the figures of FIGS. 2-A and 2-B superimposed, demonstrating that there is no difference in topography of the biologically relevant amino acid side chains between the two isomers. FIG. 3 shows a relaxed stereo view of a metal ion-labeled peptide with a primary unlabeled structure of Thr-D-Lys-Gly-D-Cys-Arg. FIGS. 3-A and 3-B show the two isomers created by the isomerism in the metaloxo group. FIG. 3-C shows the figures of FIGS. 3-A and 3-B superimposed, demonstrating that there is no difference in topography of the biologically relevant amino acid side chains between the two isomers. As a result, the biological activity of the two isomers is similar, unless metaloxo group in one of the two isomers causes steric hindrance during interaction of the complex with the biological target. In these instances, one of the two isomers may have a higher biological activity profile.

Most metal ion complexes have a coordination number 6 or 4. Complexes with coordination numbers of 2, 3 and 7 are rare. Metal complexes with a true odd coordination number are relatively rare due to their unusual stereochemistry and coordinate bond character. Many complexes of metal ions with a coordination number of 5 are known, mostly as a mono-oxo or di-oxo metal-cation as the central metal ion species. In these types of complexes several transition metal ions are known to exist as different central species for the same oxidation state. One example is molybdenum in 5+state in mono-oxo forms such as Mo(V), $MoO^{3+}$, $MoO_2^+$ and dinuclear forms such as $Mo_2O_2^{6+}$, $Mo_2O_3^{4+}$, and $Mo_2O_4^{2+}$. Similarly, technetium also exists in multiple oxidation states of 1− to 7+ with coordination numbers ranging from 4 to 9 as a Tc or Tc-oxo metal-cation as the central species (Tisato F, Refosco F, Bandoli G: Structural survey of technetium complexes. *Coordination Chem Rev* 135/136:325–397, 1994; *The Chemistry of Technetium in Medicine*, Steigman J and Eckelman W C, National Academy Press, Washington, D.C., 1992). Rhenium chemistry is similar to that of technetium chemistry, and similar sets of rhenium complexes arising due to various metaloxo states, oxidation states, and coordination numbers are possible (Rouschias G: Recent advances in the chemistry of rhenium. *Chemical Rev* 74:531–566, 1974). A variety of geometries exhibited by these complexes include trigonal bipyramid (oxidation state 1-, coordination number 5), octahedral (oxidation states 1–6, coordination number 6), pentagonal bipyramid (oxidation state 3, coordination number 7), square pyramidal (oxidation state 5, coordination number 5). In any event, the metal ion-binding backbone is specified such that the valences of the metal ion are satisfied upon complexation.

Biological-Function Domain. The biological-function domain of the constructs is a structural entity within the molecule that binds the biological target and may either cause signal transduction or block the biological signal transduction. For peptides which can form a ligand and receptor pair, in which the receptor is not a biological target, the discussions pertaining to a biological-function domain apply unless expressly limited to biological systems. The biological-function domain of the peptide includes the various amino acid side chains, arranged so that the domain binds stereospecifically to the receptor and may optionally trigger or block a biological response. The biological-function domain may be either be sychnological (with structural elements placed in a continuous sequence) or rhegnylogical (with structural elements placed in a discontinuous sequence), as such concepts are described generally in Schwyzer R: Peptide-membrane interactions and a new principle in quantitative structure-activity relationships. *Biopolymers* 31:875–792, 1991, the teachings of which are incorporated herein by reference.

The design of a biological-function domain based upon a given complexing backbone for complexing metal ions may be carried out in at least two different ways. In one approach the metal ion-binding backbone and the biological-function domain are merged so that the biologically relevant functional groups are arranged directly on, and are coextensive with, the metal binding domain, and the binding of the metal ion to the metal binding domain fixes the topography of the biological-function domain. Thus, the biological-function domain, when the conformation of the metal binding domain is fixed by binding of the metal ion, possesses relevant functional groups similar to the desired biologically active three-dimensional structure. Metal complexation by this approach therefore causes regional conformational changes that fix the topography of biologically relevant functional groups. This approach is well suited for, but not limited to, peptide ligands that fold as a reverse turn in their biologically active form. Examples of these ligands include opioid peptides, luteinizing hormone releasing hormone, somatostatin, melanotropin, tachykinins, and cholecystokinins, among many others.

In another approach, the biological-function domain is distinct from the metal binding backbone, and the complexation of the metal ion to the metal ion-binding backbone causes the peptide to have a globally constrained secondary structure, resulting in topographic alignment of the biological-function domain in the desired biologically active three-dimensional structure. This type of approach is well suited for, but not limited to, peptide ligands that incorporate a cyclic disulfide, lactam, lactone, thioether or similar bridge, and have a sychnological biological domain. It is also possible to incorporate both approaches in a given construct, so that all or a portion of the metal ion-binding backbone forms a part of the biological-function domain, with one or more distinct distal regions of the molecule forming the balance of the biological-function domain. In such cases, the biological-function domain may be either sychnological or rhegnylogical, but will most generally be rhegnylogical.

This invention thus includes two broad classes of metal ion complexed molecules, which molecules may be peptides, peptidomimetics or other organic molecules. In all cases, the metal ion is complexed to a suitably designed molecule to cause either local or global conformational constrictions. In a locally restricted metallopeptide the metal ion-binding domain and the biological-function domain are coextensive and are indistinguishable from one another. In a globally constrained metallopeptide these two domains can be structurally and spatially distinct, and can be differentiated in the molecule, but the molecule is configured such that complexation of a metal ion to the metal ion-binding domain constricts the conformation of the biological-function domain.

The biological potency, or affinity of the ligand for its receptor, of peptides of this invention is directly related to binding or complexation of a metal ion to the metal ion-binding backbone. The biological potency or affinity of peptides of this invention which are not bound or complexed with a metal ion is either negligible or significantly lower than that obtained with a metal-ion complexed peptide. This feature is highly advantageous in the case of constructs complexed with paramagnetic and radioactive metal ions, in that only the metal ion complexed molecules are biologically relevant; thus, if only 5% of the peptide molecules in a given preparation are metal ion complexed, then only that 5% will be biologically active. The remaining 95% of the peptide molecules, which are not metal ion complexed, will exhibit little or no biological activity. The metal ion labeled species is therefore essentially carrier-free, in that only peptide molecules carrying a metal ion are substantially biologically active. Thus, the entire mixture, include non-complexed peptide molecules, can be administered in vivo or used for in vitro assays without any requirement for purification to separate labeled molecules from unlabeled molecules. This presents significant advantages, in that the amount of biologically active peptide which is administered is substantially smaller than can be achieved by prior art methods. For example, in the case of a biologically active peptide which binds to a desired receptor but is toxic or has undesired biological activity, the toxicity or biological activity is minimized because only those peptide molecules which are labeled with a metal ion are substantially biologically active. Those molecules which are not metal ion complexed, which in the case of radiopharmaceuticals will generally be a substantial majority of the total, will exhibit little or no biological activity, and thus will cause little or no toxicity, competition for receptors or undesired biological activity. Similarly, since only the peptides which are metal ion complexed are significantly biologically active, the specific activity of the percentage of peptides which are metal ion complexed and hence biologically active is at or near the theoretical maximum possible.

Forming Complexes with Metal Ion. The complexation of the metal ions to the peptide, and specifically to the metal ion-complexing backbone of the peptide, is achieved by mixing appropriate amounts of the peptide with the metal ion. This is preferably done in solution, with the solution including an appropriate buffer. In one approach, the metal ion is, when mixed with the peptide, already in the oxidation state required for complexing to the metal ion-complexing backbone. Some metal ions are complexed in their most stable oxidation state, such as ionic forms of calcium, potassium, indium, manganese, copper, zinc, cobalt and other metals. In another approach, the metal ions must be reduced to a lower oxidation state in order to be complexed to the metal ion-complexing backbone. This is true of ferrous, ferric, stannous, stannic, technetiumoxo[V], pertechnetate, rheniumoxo[V], perrhenate and other similar metal ions. Thus, for example, both perrhenate and pertechnetate must be reduced to a lower oxidation state prior to complexing. Reduction may be performed prior to mixing with the peptide, simultaneously with mixing with the peptide, or subsequent to mixing with the peptide. Any means of reduction of metal ions to the desired oxidation state known to the art may be employed. For example, perrhenate or pertechnetate may be reduced by use of stannous ions, dithionite or other means. The stannous or dithionite metal ion reducing agent may be mixed with the metal ion to be reduced either prior or subsequent to addition of the metal ion to the peptide, or the reducing agent may be in solution with the peptide when the metal ion to be reduced, and subsequently complexed to the peptide, is added to the solution.

The stoichiometric ratios between the peptide and the metal ion in the labeling or complexing step can be varied depending on the application. For example, in the case of radiometal complexation, the ratio of radiometal ions to peptide molecules can be varied from less than 1:2 to 1:1000 or higher, without generating substantial radiochemical impurities. In other applications, the ratio of metal ions to peptide molecules can range from at least 1000:1 to 1:1000 or higher. When the concentration of metal ions is higher than the concentration of peptide molecules, all or virtually all of the peptide molecules will be complexed to metal ions. The ratio of metal ion to peptide directly affects the percentage of the peptide which will be conformationally constrained so that it has biological or other ligand activity, but otherwise there is no effect on receptor localization or targeting. For example, it is possible to complex metal ion to only 1% of the peptide molecules, by having a ratio of metal ion to peptide of 1:100, so that only 1% of the peptide molecules will have biological or other ligand activity.

Either radioactive or non-radioactive metal ions can be employed. Where a specific diagnostic or therapeutic advantage can be obtained from use of a radioisotope, then a radioactive metal ion is employed. Where the diagnostic or therapeutic utility is obtained from the conformationally constrained biological-function domain, a non-radioactive metal ion is employed. It is possible and contemplated, and may for certain applications be advantageous, to employ different metal ions with the same peptide product of this invention. For example, a peptide of this invention with an $N_4$, $N_3S_1$ or $N_2S_2$ metal ion-binding domain may be complexed with a gamma-emitting metal ion, such as $^{99m}Tc$; separately with a beta-emitting metal ion, such as $^{186}Re$ or $^{188}Re$; and separately with a non-radioactive metal ion, such as stable ReO[V]. While there might be differences in the complexation chemistry, such as the means necessary to reduce the metal ion to an appropriate oxidation state, no change in the structure of the peptide would be required to successfully complex with the different metal ions.

Polymer Constructs. In order to alter the pharmacokinetic profile of the peptide-metal ion complexes of this invention, the complexes may be conjugated to various polymers, thereby altering the molecular size, charge, hydrophobicity and other characteristics of the molecule. Polymers which may be conjugated to peptide constructs include polyethylene glycol (PGA), polyvinyl alcohol (PVA), polyamino acids, fatty acids, lipid molecules and the like. The peptide-metal ion complexes may also be encapsulated into liposomes, thereby resulting in a marked difference in the pharmacokinetics and bioavailablity of the peptide-metal ion complexes within the liposomes.

Other Diagnostic Imaging Applications. The peptides and methods of this invention may also be applied to diagnostic agents for use in positron emission tomography (PET) and magnetic resonance imaging (MRI). For use as a PET agent, a peptide is complexed with one of the various positron emitting metal ions, such as $^{51}Mn$, $^{52}Fe$, $^{60}Cu$, $^{68}Ga$, $^{72}As$, $^{94m}Tc$, $^{110}In$ and isotopes of At. For MRI applications the complexing metal ion is paramagnetic, such as Mn, Gd, Fe, or Dy.

In both MRI and PET applications of the present invention only the fraction of the molecules that bind the relevant metal ion assume the receptor reactive three-dimensional structure, while the uncomplexed peptide molecule is devoid of or has limited biological potency. Thus the present invention affords an advantage in these diagnostic modalities in that the metal-labeled species can be administered without the need to separate the metal-labeled fraction from the uncomplexed peptide molecules.

Use as Carrier of Therapeutic Agents. The products of this invention and the products made by the methods of this invention may also be used as vectors or carriers for target-specific delivery of other chemical species of therapeutic relevance, such as chemotherapy agents, gene regulation agents, enzyme function inhibition agents, target cell membrane disrupting agents, viral blocking agents, antibody blocking agents, and the like. The therapeutic payload can be conjugated to the peptide at sites other than those essential in either complexing the metal ion or binding the biological target. The therapeutic payload may be conjugated to the peptide either prior to or subsequent to complexing the peptide to a metal ion, and thus activating the biological-function domain.

In Vivo Metal Ion Complexation. The peptide constructs of this invention may also be administered in vivo without complexation to a metal ion. Subsequent complexation of the peptide with a metal ion, which metal ion may be endogenous or may be separately administered, will cause the peptide to become conformationally constrained, thereby causing the biological-function domain to become specific for its target. Thus, administration of a suitably designed peptide made by the methods of this invention, which complexes a metal ion present in the circulation, would convert the peptide into the biologically active form upon complexation with an endogenous or subsequently administered metal ion.

Radiopharmaceutical Applications. Products of this invention, and products made by the methods of this invention, may be employed as radiopharmaceutical agents. For example, when labeled with gamma-emitting radioisotopes, such as $^{99m}$Tc, the products may be utilized for diagnostic nuclear medicine. For such use, the peptide of this invention includes a biological function-domain specific for a receptor which is characteristic of a particular disease state, or which is present on cells which are found in higher concentration at the sites of disease. For example, a peptide with a biological function-domain specific for platelets or fibrin or other blood clot components may be used for diagnostic imaging of thrombi. Similarly, a peptide with a biological function-domain specific for any of a number of white blood cells, including polymorphonuclear cells, may be used for diagnostic imaging of sites of infection or inflammation. The receptor may also be disease specific, such as tumor markers found in certain cancers.

Products of this invention, and products made by the methods of this invention, may also be used as therapeutic agents when labeled with alpha- or beta-emitting radioisotopes. For example, peptides labeled with alpha- or beta-emitting radioisotopes, such as Rhenium-186 ($^{186}$Re) or Rhenium-188 ($^{188}$Re), can be used for therapy of diseases, including specific cell surface receptor-associated diseases such as various cancers.

The products of this invention, and products made by the methods of this invention, may be used for any radiopharmaceutical application for which a biologically active peptide or protein molecule may be employed. This includes, but is not limited to, products which are based on the binding site of antibody fragments, including F(ab')$_2$, Fab, Fv and Fc fragments of monoclonal antibodies, or are otherwise based on the hypervariable region of monoclonal antibodies, including single-chain binding proteins. This also includes other antigen binding domain fragments and biologically active peptides. This allows the rational development of peptide-based imaging and therapeutic agents, by using the methods of this invention, to design and make a peptide, including a peptidomimetic or psuedopeptide, which upon labeling with a metal ion mimics the known binding characteristics of the parent molecule. Examples of suitable products which may be made by the methods of this invention include peptides which have biological-function domains, upon labeling with a metal ion, functionally similar to those of RGD, YIGSR, For-MLF, TGF-beta (tumor growth factor), FGF (fibroblast growth factor), PDGF (platelet-derived growth factor), EGF (epidermal growth factor), NGF (nerve growth factor), neuropeptide Y, cholecytokinin, tumor-related markers, hormones such as estrogen, tuftsin, melanotropin, somatostatin and the like. Over 300 receptors and their agonists are known, each of which is a potential candidate for a product of this invention.

For radiopharmaceutical applications, and other medical applications, the peptides of this invention, and products made by the methods of this invention, offer significant advantages over conventional linear or single-chain peptide constructs. For example, it is known that conformationally constrained and dimeric peptides derived from hypervariable loop sequences of antibodies can bind antigens with an affinity up to 40-fold higher than that obtained with linear sequence peptides. The peptides of this invention, in that they are by definition conformationally constrained upon labeling with a metal ion, have a similarly higher affinity than that obtained with conventional linear sequences.

For radiopharmaceutical applications, and other medical applications, the peptide may be delivered by any means known in the art. This includes intravenous injection, subcutaneous injection, administration through mucous membranes, oral administration, dermal administration, regional administration to an organ, cavity or region, and the like.

High Affinity Complexes. The products of this invention, and products made by the methods of this invention, exhibit extremely high affinity when labeled with a metal ion. This is particularly relevant for products which are small peptide constructs, on the order of three to about twenty amino acids. Prior art linear peptide sequences, which are not conformationally constrained, typically exhibit substantially lower affinity for their target than the parent molecule, such as an antibody hypervariable region, which is conformationally constrained. Thus, the products of this invention may be used directly as therapeutic agents, in which the metal ion serves to conformationally fix the biological function-domain, but in which the metal ion does not itself necessarily serve as a therapeutic component. For example, it is possible to design, using the methods of this invention, peptide-metal ion complexes that display biological activity profiles of a peptide hormone, neurotransmitter, steroid hormone, enzyme inhibitor and the like. The peptide-metal ion complexes of this invention bind biological receptors with high affinity in a stereospecific manner, thereby exerting a biological response as an agonist, antagonist or mixed agonist-antagonist. The peptide-metal ion complex can also be employed as a target-specific suicide substrate, by incorporating a reactive chemical group such as an isocyanate group, thiocyanate group, α-haloketone, mustard moiety or the like in the peptide so that after binding the target receptor or enzyme, the reactive group forms an irreversible bond with the target molecule rendering it ineffective to transduce further biological signals.

Use as a Therapeutic Agent. The products of this invention, and products made by the methods of this invention, may be used, in general, for any application in which a peptide, including peptidomimetics or pseudopeptides, may be employed. The products are particularly useful for peptide drugs in which a globally constrained structure, or a ligand or biological-function domain, is required. In these applications, the metal ion may serve only to conformationally constrain the peptide, or a portion thereof, or may itself be related to the therapeutic nature of the agent. Various peptide drug applications are disclosed elsewhere herein. In general, the products of this invention may find therapeutic uses similar to those of existing peptide- or peptidomimetic-based therapeutics, including (a) hormones such as oxytocin, vasopressin, somatostatin, melanotropins, leutinizing hormone releasing hormone, insulin, calcitonin, steroid hormones, etc.; (b) enzyme inhibitors such as renin and angiotensin converting enzyme inhibitors, HIV proteases, etc.; (c) antibiotics such as valinomycin, penicillin, tetracycline, bleomycin, etc.; (d) ion channel blockers; (e) analgesics; (f) growth factors, and many others. The development of peptide-based pharmaceuticals is described generally in *Peptide Pharmaceuticals: Approaches to the Design of Novel Drugs*, D J Ward, editor, Open University Press, London, 1989, incorporated herein by reference.

Mimics of Non-Peptide Biological-Function Domains. Biological-function domains may be mimics of naturally occurring ligands which are non-peptidic. For example, using the methods and constructs of this invention, it is possible to make mimics of steroids, hormones and other ligands. Thus, this invention encompasses situations in which either the receptor or its naturally occurring ligand or ligands, or both, are not constructed of peptides.

One illustration of the design of metallopeptide constructs is that of a mimic of a non-peptidic natural molecule, paclitaxel (taxol). The crystal structure of paclitaxel is used as starting point (Mastropaolo D et al: Crystal and molecular structure of paclitaxel (taxol). *Proc Natl Acad Sci USA*, 92:6920–6924, 1995) to design a peptidic molecule which is substituted with suitably derivatized side chains. Preferably, a library of molecules of the following general structure is constructed:

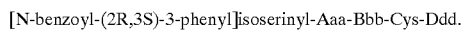
[N-benzoyl-(2R,3S)-3-phenyl]isoserinyl-Aaa-Bbb-Cys-Ddd.

Where Aaa, Bbb and Ddd are randomized amino acid derivatives that mimic one or more functional groups in paclitaxel that are essential for biological activity. These molecules, upon complexation with a metal ion, such as ReO[V], yield exchange-inert metallopeptides in which the derivatized amino acid side chain functionalities spatially mimic at least two or more of the following functionalities of paclitaxel: C-13 side chain, C-1 OH group, C-2 benzoate, C-4 acetate and C-10 acetate. These side chains of paclitaxel are known to be critical for biological activity, with the C-13 side chain, with its unique chirality, being perhaps the most crucial of all (Gueritte-Voegelein F et al: Relationship between the structure of taxol analogues and their antimitotic activity. *J Med Chem* 34:992–998, 1991; Kingston DGI: The chemistry of taxol *Pharma Ther* 52:1–34, 1991; Grenard D et al: Taxol and texotere: Discovery, chemistry, and structure-activity relationships. *Acc Chem Res* 26:160–167, 1993). The C-13 side chain, N-benzoyl-(2R, 3S)-3-phenylisoserine, is now commercially available (Cat. No. 44,437-5, Aldrich Chemical, Milwaukee, Wis.).

Non-Peptide Structurally Determined Metal Ion Constructs. It is also possible, using the methods and teaching of this invention, to design, make and use metallo-construct molecules, which are not composed of amino acids, and which are not peptides as defined herein, but which incorporate both a metal ion-binding domain and a biological-function domain. For example, non-peptidic molecules can be designed so as to complex a metal ion, and which are further characterized by being substantially biologically active for a target biological receptor only upon metal complexation. The basic features of designing this class of constructs are similar to those involved in designing the peptide constructs of this invention. An aliphatic, aromatic, or a combination thereof, backbone is designed to complex a metal ion so that all valences of the metal ion are satisfied. The backbone incorporates a sufficient number of N, S or O metal ion-binding sites, or a combination of N, S and O metal ion-binding sites, to complex a metal ion. In addition, the backbone is derivatized with functional groups and structural elements that are required for binding to a biological target, and which together form a biological-function domain. The biological-function domain may either be totally or partially coextensive with the metal ion-binding backbone; but in any event, complexation of the metal ion causes global structural organization of the molecule, thereby forming a topography that mimics the biological active conformation for a ligand binding a given biological receptor.

A simple illustration of a non-peptide of this invention is an metallo-construct mimic of the RGD sequence, which binds to the integrin family of receptors, that is made by complexing a metal ion, such as $^{99m}$Tc, Re, In, Mn, Fe, or Cu., to an equimolar covalent adduct of diethylenetriamine-pentaacetic acid (DTPA) with ethylenediamine. This adduct may be achieved by reacting ethylenediamine with DTPA-dianhydride. The amino group of the ethylenediamine moiety in this adduct, together with the free carboxylate of the DTPA moiety, mimic the two primary integrin receptor-binding functionalities. The use of higher homologues of ethylenediamine, or use of other di-amines, such as 1,4 piperazine, as well as aromatic amine derivatives in the formation of these adducts, may provide metallo-constructs that are specific for one or more of the integrin family of receptors. Yet another way to construct these types of ligands is by forming an adduct of diethylenetriamine or its homolog with succinic acid or its homolog using anhydride of the latter. The resulting complex, with its N groups, is able to complex a metal ion and provides both a cationic and anionic center to form a biological function domain. The charged functionalities in this class of molecules may also be functionalized using a variety of substitutes, including phenolic, phenyl, imidazole, or indole groups that are known to form a portion of biological-function domains of various peptidic hormones and neurotransmitters, such as opioids, somatostatin, cholecystokinin, melanotropin, and neurokinins. The synthetic methods to form these adducts may require orthogonal protection of one or or more chemically reactive groups.

Use in Peptide and Metallo-Construct Molecule Libraries and Combinatorial Chemistries. There is an increasing emphasis on designing peptide, peptidomimetic, psuedo-peptide, and non-peptide organic molecular libraries that are highly biased in terms of structural and conformational diversity as well as specifically directed towards a particular biological target. In many applications, libraries of peptido-mimetics and small organic molecules are preferred over peptide libraries because of considerations such as metabolic stability, bioavailability and pharmacokinetics. The prior art with respect to libraries and combinatorial chemistry has not addressed or explored the area of metallopeptides and metallo-construct molecules. Metal complexed to a suitably designed peptide or organic molecule so as to satisfy the metal coordination sphere leads to highly constrained structures, with significant advantages in specificity, affinity, metabolic stability, bioavailability and pharmacokinetics.

One application of this invention is the use of either locally or globally constrained metallopeptide structures as templates to assemble libraries. Libraries of metallopeptides may include molecules with either local conformation restrictions or global conformation restrictions, or some combination thereof. This aspect of the invention includes a variety of methods of synthesis, screening and structural elucidation of positive hits in screening systems. The importance of these aspects are well known to those skilled in the art and will also become evident from the following description and examples.

In one embodiment of this invention, the metal-coordinated molecules are obtained from the peptides in which individual amino acids provide the biological target-specific side chains. Various compounds in a library of metallopeptides can be obtained by varying the sequence of amino acids in a set of peptides that are all optimized to form a complex of nearly similar geometry when coordinated with a metal ion. This optimization can be obtained, for example, by appropriate positioning of amino acids having high affinity to complex a metal ion. Examples of naturally occurring amino acids with high affinity for metal complexation include Cys and His. A library of such peptides, therefore, would have at least one of these amino acids that is suitably placed in the sequence, with this amino acid being common to all the molecules in the library, and thus with this amino acid non-randomized. A conceptual, generalized view of a solid phase library of metallopeptides that is constructed using local conformational restriction is:

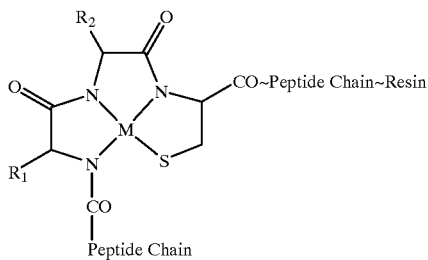

where M is a metal ion, and $R_1$ and $R_2$ are randomly selected amino acid side chains forming parts of the potential biological-function domain. A similar library can also be constructed in which the components are soluble, and thus not bound to a resin.

One illustration of a locally restricted metallopeptide library, in which the members are conformationally constrained upon metal ion complexation, is a library directed towards the family of various integrin receptors that recognize the RGD sequence. In this library, individual amino acid positions are degenerated by selecting a set of cationic amino acids for one position, a second set of anionic amino acids for another position and a third set of selected amino acids with strong metal complexation properties. Other positions in the peptides can be randomized. The common rigid structure of the metal-peptide complex in this library allows for various forms of presentation of the cationic and anionic centers for interaction with the integrin receptors. A library of these structures can help identify specific metallopeptides for individual integrin receptors. The general structure of this library, which can either be soluble or solid-phase library, prior to metal ion complexation is:

$R_1$-Aaa-Bbb-Ccc-Ddd-$R_2$ (for soluble libraries)

or $R_1$-Aaa-Bbb-Ccc-Ddd-$R_2$-Resin (for solid phase bound libraries)

Where:
Aaa=L- or D-configuration residue providing an N for metal ion complexation, such as Arg, Lys, Orn, homoArg, 2,3-diamino propionic acid, 2,4,-diaminobutyric acid, S-aminoethyl cysteine, 3(O-aminotheyl) Ser, or other synthetic basic amino acids.

Bbb=L- or D-configuration residue providing an N for metal ion complexation, such as Gly, Ala, Aib, Val, Nle, Leu or similar amino acids with uncharged side chains.

Ccc=L- or D-configuration residue providing both an N and S, or alternatively two Ns, available for metal ion complexation, such as Cys, HomoCys, Pen, His, or other amino acids, natural or unnatural, containing both an N and S, or alternatively two Ns, available for metal ion binding.

Ddd=L- or D-configuration residue with a negatively charged side chain functional group, such as Asp, Glu, or synthetic amino acids with a negatively charged side chain functional group.

$R_1$, $R_2$=H, Alkyl, aryl, alkylcarbonyl, arylcarbonyl, alkyloxycarbonyl, aryloxycarbonyl, or a polymer such as PEG, PVA, or polyamino acid, attached directly or through a carbonyl group.

Other forms of this library include sets of structures with general formulas shown below, wherein the spatial distances between the cationic and anionic centers can be different than those shown above:

$R_1$-Bbb-Aaa-Ccc-Ddd-$R_2$ (for soluble libraries)

or $R_1$-Bbb-Aaa-Ccc-Ddd-$R_2$-Resin (for solid-phase bound libraries), and $R_1$-Bbb-Ddd-Ccc-Aaa-$R_2$ (for soluble libraries)

or $R_1$-Bbb-Ddd-Ccc-Aaa-$R_2$-Resin (for solid-phase bound libraries), and $R_1$-Ddd-Bbb-Ccc-Aaa-$R_2$ (for soluble libraries)

or $R_1$-Ddd-Bbb-Ccc-Aaa-$R_2$-Resin (for solid-phase bound libraries).

For each of the foregoing, the definitions of $R_1$, $R_2$, Aaa, Bbb, Ccc and Ddd are as described above. All four classes of libraries described above can either be synthesized individually or prepared as one library.

Another example of a biological target-specific library of locally restricted metallopeptides constructed according to this invention are tuftsin mimetics. Tuftsin, the tetrapeptide Thr-Lys-Pro-Arg, is a natural stimulator of phagocytosis. The basic criteria of this library of molecules are similarly a common rigid structural template formed by metal-peptide complexation, the presence of at least one amino acid suitably placed and known to have a high propensity to form a strong initial bond with a metal ion, and the presence of amino acids with side chains able to bind to the biological target receptor. One example, out of various general structures, includes:

$R_1$-Aaa-Bbb-Ccc-Ddd-Eee-$R_2$ (for soluble libraries)

or $R_1$-Aaa-Bbb-Ccc-Ddd-Eee-$R_2$-Resin (for solid phase libraries)

Where:
- Aaa=L- or D-configuration neutral residue, such as Thr, Cys, Pen, Pro, Ser, or similar neutral amino acids, and their corresponding des-amino derivatives.
- Bbb=L- or D-configuration basic residue, providing an N for metal ion complexation, such as Arg, Lys, Orn, homoArg, 2,3-diamino propionic acid, 2,4,-diaminobutyric acid, S-aminoethyl cysteine, S-aminopropyl cysteine or other basic amino acids.
- Ccc=L- or D-configuration resideue with an uncharged side chain, providing an N for metal ion complexation, such as Gly, Ala, Aib, Val, Nle, Leu or similar amino acids with un-charged side chains.
- Ddd=L- or D-configuration residue providing both an N and S, or alternatively two Ns, available for metal ion complexation, such as Cys, HomoCys, Pen, His, or other amino acids, containing both an N and S, or alternatively two Ns, available for metal ion binding.
- Eee=L- or D-configuration basic residue, such as Arg, Lys, Orn, homoArg, 2,3-diamino propionic acid, 2,4,-diaminobutyric acid, S-aminoethyl cysteine, S-aminopropyl cysteine, or other basic amino acids.
- $R_1$=H, Alkyl, aryl, alkylcarbonyl, arylcarbonyl, alkyloxycarbonyl, aryloxycarbonyl, or a polymer such as PEG, PVA, or a polyamino acid, attached directly or through a carbonyl group.
- $R_2$=Amide, substituted amide, ester, or a polymer such as PEG, PVA, or a polyamino acid.

Another embodiment of this invention provides for construction of a library of metallopeptides with global conformational restriction. This type of library encompasses metallopeptides in which a metal binding domain is an isosteric replacement for a disulfide, lactam, lactone, thioether or thioester moiety in cyclic peptides. In these constructs a metal binding site is introduced between two pre-selected ends of a linear peptide that contains the biological function domain. The general structure of a metallopeptide library of this type is:

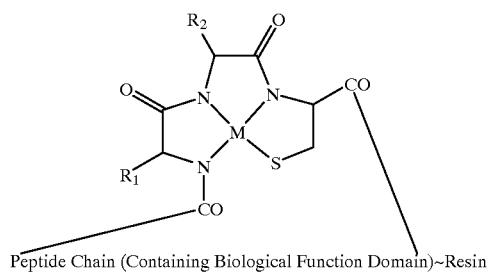

Peptide Chain (Containing Biological Function Domain)~Resin where M is a metal ion and $R_1$ and $R_2$ are structural elements that may provide additional stability to metal complexation, or may modulate biological activity, such as determining the organ of clearance, or altering biodistribution patterns or pharmacokinetics.

One illustration of a globally-constrained metallopeptide library is a library of peptides wherein all the individual members of the library include a metal ion-binding domain and the library is directed specifically towards a family of peptide hormones, such as somatostatin, cholecystokinin, opioid peptides, melanotropins, luteinizing hormone releasing hormone, tachykinins and similar peptide hormones. The general formula of this library of peptides, before complexation to a metal ion, is:

$R_1$-Aaa-$R_3$-Bbb-$R_2$~Resin wherein X is a metal ion chelating domain including a plurality of amino acids, so that all of the valences of the metal ion are satisfied upon complexation of the metal ion with X, wherein $R_1$ and $R_2$ each comprise from 0 to about 20 amino acids, wherein $R_3$ comprises from 1 to 20 amino acids, wherein Aaa and Bbb each comprise an amino acid connected to X through an amide, thioether, thioester, ester, carbamate, or urethane bond, and wherein $R_3$ alone or in combination with either $R_1$ or $R_2$ or $R_1$ and $R_2$ together forms and defines the biological-function domain.

For solid phase libraries the peptide constructs are attached to a resin, and the resin is omitted for soluble libraries. This library of globally constrained metallopeptides can also be screened for detecting compounds that are mimetics for various peptides that are known to exist in a reversed turn structure as their hypothesized biologically active structure. The examples of these include various peptide hormones such as somatostatin, cholecystokinin, opioid peptides, melanotropins, luteinizing hormone releasing hormone, tachykinins and various antibody epitopes.

The functional equivalent of each these peptide libraries may also be obtained through the development of a library of non-amino acid building blocks so as to result in structural mimics of these peptides. The peptide bonds may be replaced by pseudopeptide bonds, such as thioamides, thioethers, substituted amines, carbanate, urethane, aliphatic moieties, and functionally similar constructs.

A metallopeptide library is obtained by post-synthesis peptide, pseudopeptide, non-peptide, or peptidomimetic modification. A peptide library is first assembled according to the sequence specification and degeneration, as described above, by well known methods of peptide synthesis. These libraries can be synthesized as discreet, spatially addressable compounds in parallel synthesis, using split synthesis approaches, or by deconvolution techniques of soluble libraries. Using similar methods, a pseudopeptide, peptidomimetic or non-peptide library can be obtained. The non-peptide libraries may also incorporate one of various tagging approaches that are well known to those skilled in the art. Both solid-phase and soluble libraries can be obtained in this manner. The entire library is then reacted with an appropriate metal-complexing agent to obtain the corresponding metal-coordinated library, comprising a similar class of predetermined structures. For example, to complex a peptide library with rheniumoxo metal ion, the peptide library is treated with oxotrichlorobis(triphenylphosphine) rhenium [V] in the presence of sodium acetate. This procedure results in quantitative complexation of ReO[V] with the peptide. In order to complex Zn, Co, Mn, Fe or Cu ions, the peptide library is treated with chloride or other suitable salts of these metal ions to yield the library of corresponding metal ions. Essentially, a variety of metal ions can be used to construct different metallopeptide libraries. One limiting factor, in selection of the appropriate metal ion, is the relative stability of a particular metal-peptide complex, related in large part to the metal-peptide binding constant or constants. It is well known in the art that some metal-peptide constructs are stable only within specified pH or other special conditions, or are easily oxidized in air. Some peptide-metal ion complexes, such as those with ReO[V], are stable in pure form and can be isolated and stored under normal storage conditions for a long period of time.

A metallopeptide library constructed according to this invention can be screened to identify one or more receptor-binding or pharmacologically-active candidates by various techniques that have been reported in the prior art. Both soluble and solid phase libraries may be directly employed in these assays. These techniques include direct target binding approaches as described by Lam and coworkers (Lam K S et al: *Nature* 354:82–84, 1991; Lam K S et al: *Nature* 360:768, 1992), deconvolution and iterative re-synthesis approaches (Houghten R A et al: *Proc Natl Acad Sci USA* 82:5131–5135, 1985; Berg et al: *J Am Chem Soc* 111:8024–8026, 1989; Dooley C T et al: *Science* 266:2019–2022, 1994; Blondelle S E: *Antimicrob Agents Chemother* 38:2280–2286,1994; Panilla C: *Biopolymers* 37:221–240, 1995), approaches using orthogonal pools of two co-synthesized libraries according to Tartar and coworkers (Deprez B et al: *J Am Chem Soc* 117: 5405–5406, 1995), positional scanning methods devised by Houghton and coworkers that eliminate iterative re-synthesis (Dooley C T et al: *Life Sci* 52:1509–1517, 1993; Pinilla C et al: *Biotechniques* 13:901–905, 1992; Pinilla C et al: *Drug Dev Res* 33:133–145, 1992), and a combination of the positional scanning method with split synthesis methods (Erb E et al: *Proc Natl Acad Sci USA*, 91:11422–11426, 1994).

Among these techniques, the deconvolution and iterative resynthesis approach, the approach involving orthogonal pools of two co-synthesized libraries, and the positional scanning method may be directly applied to soluble metallopeptide libraries to elucidate the structure of a "hit," or peptide identified as a receptor-binding or pharmacologically-active candidate in the screening process. For solid phase libraries, other than spatially addressable parallel synthesis libraries, the structure of hits can be directly determined by various strategies now well known to those skilled in the art. These include direct mass spectrometric analysis of compounds covalently bound to solid phase matrix of particles by the use of matrix-assisted laser desorption/ionization (MALDI) techniques (Siuzadak G et al: *Bioorg Med Chem Lett* 6:979, 1996; Brown B B et al: *Molecular Diversity* 1:4–12, 1995). The technique of creating a series of partially end-capped compounds at each of the synthetic steps during library assembly also helps in unambiguous identification by mass spectrometry (Youngquist R S et al: J Am Chem Soc, 117:3900–3906, 1995; Youngquist R S et al: *Rapid Commun Mass Spectr* 8:77–81, 1994). In addition to these analytical techniques, various encoding strategies that have been devised for structure elucidation in organic molecule-based libraries, including non-peptide and non-nucleotide libraries, may be utilized. Various encoding strategies, such as DNA encoding, peptide encoding, haloaromatic tag encoding, and encoding based on radiofrequency transponders, are now well known in the art and can be used directly in combination with metallopeptide libraries. These tagging strategies require the incorporation of the tags during the course of synthesis of libraries, which can be accomplished during the construction of a metallopeptide libraries, since metal complexation is a final, post-synthesis step.

Industrial and other Non-Pharmaceutical Applications. Peptides made by the methods of this invention may be employed for a wide variety of industrial, agricultural and other non-medical applications. The peptides and methods of this invention apply to any use of peptides, including peptidomimetics and other peptide variants as disclosed herein, in which it is desired that the peptide have a well-defined secondary structure. This necessarily includes peptides which bind to a particular recognition area or other actual or functional equivalent of a biological-function domain, such as peptides which form a specific interaction between a ligand and its acceptor. This method is particularly useful for small peptides, composed of less than about 20 amino acids, which it is desired will be conformationally constrained. Peptides of this invention may be used in any commercial or industrial process or application in which conformationally constrained peptides are desired or may be used. This includes such applications as waste remediation, catalytic peptides, enzymatic peptides, markers and detection systems, pesticides, animal drugs and vaccines, and the like. Peptides of this invention used in a commercial or industrial process or application may serve as carriers for any agent or reagent which may be conjugated or otherwise bound to a peptide, or may be designed so that the peptide has intrinsic biochemical properties, such as a catalytic or enzymatic peptide. Such peptides may also serve as blocking agents, which are designed to bind to a particular receptor, but which do not otherwise transmit any signal or participate in any biochemical reaction. In most applications, the metal ion will only serve to conformationally fix the peptide, and will not itself contribute to the effect of the peptide. However, possible applications include those in which the metal ion is an intrinsic part of a detection system, or in which the metal ion itself has some further effect. This includes, but is not limited to, use of metal ion peptides in which the metal ion is radioactive for commercial or industrial processes or applications.

Metabolic Stability and Bioavailability. Peptides in general are enzymatically labile. A variety of peptidases, such as serine proteases, carboxypeptidases, aminopeptidases, endo- and exo-peptidases, and many others, including peptide-specific proteases, cleave peptides, thereby rendering them biologically inactive. The primary cleavage site is the peptide (or amide) bond between two consecutive amino acids, with cleavage caused by nucleophilic attack by a specific nucleophile in the active site of an enzyme. The metallo-constructs of this invention, and particularly the metallopeptides of this invention, are highly resistant to peptidase and enzymatic degradation, and such resistance is both a characteristic and advantage of constructs of this invention. Without being bound by theory, it is hypothesized that the coordination of the nitrogens of the peptide bonds in metal ion complexation orients the amide carbonyl in a manner that sterically precludes nucleophile attack from enzymes. The stereochemistry thus makes metallopeptides of this invention highly stable against proteolytic enzymes. In addition, the conformational rigidity of these constructs may also preclude a proper fit of the active site of many enzymes.

The stability of many $^{99m}$Tc-labeled constructs of this invention was tested in rodents. All the tested metallopeptides were excreted intact through the urine of these animals. Orally administered $^{99m}$Tc-Thr-[D-Lys-Gly-D-Cys]-Arg was observed to localize at the site of experimentallyinduced inflammation in mice (FIG. 14), and to be excreted intact in the urine. This construct was thus presumptively stable in the presence of gut enzymes and enzymes and peptidases found in the serum after absorption.

Use of Metallo-Constructs to Increase Bioavailability and Pharmacokinetics. In another embodiment of this invention, metal ions complexed to peptides and other organic molecules may cause structural changes in the metallo-construct and thereby alter transport of the metallo-construct across gut-blood and blood-brain barriers, to increase transport through cell membranes, and in general to alter bioavailablity. The metallo-construct reaches or penetrates its target organ or organelle more easily than the construct which has not been complexed with a metal ion. Metal ion complexation alters the structure of the molecule, thereby changing its permeability or pharmacokinetic profile. In this instance, the metal ion-complexed construct may or may not be biologically active. The uncomplexed parent molecule may be biologically active and its biological activity may or may not be impaired as a consequence of complexation with a metal ion.

It is also possible to design metallo-constructs so that the metal ion dissociates at the target site, thereby releasing the biologically active uncomplexed construct. In this case, metal complexation facilitates the passage of the molecule through the tissue barriers. The metal dissociation process may involve a target tissue-specific biological event, including release of a specific protease, in vivo oxidative processes, pH of the tissue medium, or transchelation of the metal ion.

By way of example, an opioid peptide-metal complex may be designed that transits the blood-brain barrier. The disulfide-containing opioid peptide, [D-Pen$^{2,5}$]enkephalin, as well as its corresponding reduced congener with both free sulfhydryl groups [D-Pen(SH)$^2$, D-Pen(SH)$^5$]enkephalin, are both known to be biologically active, but not to show analgesic activity when administered through systemic routes because of their inability to cross the blood-brain barrier (Matsunaga T O, Collins N, Yamamura S, Ramawami V, O'Brien D F, Hruby V F: Comparison of the membrane bound states of two structurally similar delta selective opiod peptides by transferred nuclear Overhauser effect spectroscopy and molecular modeling. *Biochem* 32:13180–13190, 1993). Complexation of [D-Pen(SH)$^2$, D-Pen(SH)$^5$]enkephalin with a metal ion, such as Cu, Zn, or ReO(V), through its endogenous sulfhydryl groups, alters the water association and hydrogen bonding properties of the molecule, which assists in transit through the blood-brain barrier.

Examples of Peptide Design. General design considerations for two peptide constructs, and for design of globally constrained peptides containing a metal-binding sequence, are given below. These design considerations, and modifications thereof, may be employed in any case in which a biological function-domain, or ligand structure, is known.

RGD Analogue Construct. Locally restricted peptides, in which the biological-function domain and metal-peptide backbone are combined, were constructed based upon an analogue to the tripeptide sequence Arg-Gly-Asp (RGD). RGD peptides, related to many extracellular matrix proteins, interact with a variety of heterodimeric receptors called integrins (Craig W S et al: Concepts and progress in the development of RGD-containing peptide pharmaceuticals. *Biopolymers(Peptide Sci)* 37:157–175, 1995), which mediate various cellular and vascular functions including cell-cell adhesion, blood coagulation, and angiogenesis. The integrin receptor which mediates platelet aggregation and blood coagulation is the $\alpha_{IIb}$-$\beta_3$ receptor, also called the integrin heterodimeric glycoprotein IIb/IIIa (GP IIb/IIIa), a transmembrane protein found on the surface of platelets. The integrin receptor associated with angiogenesis is the $\alpha_v$-$\beta_3$ receptor. Many RGD-based ligands have been developed as antagonists of platelet adhesion and for treatment of myocardial infarction (for example, see Jackson S et al: Template-constrained cyclic peptides: Design of high-affinity ligands for GP IIb/IIIa. *J Am Chem Soc* 116:3220–3230, 1994), anti-angiogenesis agents to starve and stop tumor growth (Brooks PC et al: Integrin $\alpha_v$-$\beta_3$ antagonists promote tumor regression by inducing apoptosis of angiogenic blood vessels. *Cell* 79: 1157–1164, 1994; Pfaff M et al: Selective recognition of cyclic RGD peptides of NMR defined conformation by $\alpha$IIb$\beta$3, $\alpha$v$\beta$3 and $\alpha$5$\beta$1 integrins. *J Biol Chem* 269: 20233–20238, 1994; Bach II AC et al: Type II' to type I $\beta$-turn swap changes specificity for integrins. *J Am Chem Soc* 118:293–294, 1996), inhibitors of bone resorption (Duggan M E et al: Design and evaluation of potent non-peptide ligands of $\alpha$v$\beta$3 as inhibitors of bone resorption. 211th National Meeting of the American Chemical Society, New Orleans, La., March 24–28, abstract No. 234, 1996) and as biocompatible coatings (Craig W S et al: Concepts and progress in the development of RGD-containing peptide pharmaceuticals. *Biopolymers(Peptide Sci)* 37:157–175, 1995) to promote cell matrix adhesion, prevent rejection of transplanted tissues and organs, and many other indications.

The GP IIb/IIIa heterodimeric complex changes conformation in response to platelet-stimulating agents, including peptides containing the RGD sequence. Many naturally occurring peptides of different origin, such as echistatin from snake venom and elsewhere, contain the RGD sequence as a common motif for binding to the GP IIb/IIIa receptor. Binding of fibrinogen through RGD motif causes activation of the platelets. Mimics of RGD sequence that can block fibrinogen binding to the GP IIb/IIIa receptor, thereby inhibiting platelet aggregation, are being pursued as therapeutic modalities for myocardial infarction. In addition, radiolabeled forms of these agents show promise as in vivo imaging agents for various forms of thrombus.

To construct a conformationally constrained peptide using the method of this invention, a peptide molecular construct to bind a technetium (or rhenium) metal ion, with the ability after binding the metal ion to bind a platelet fibrinonectin receptor, was designed so that the four available valences of the core of reduced technetium (or rhenium) oxide [V] were coordinated to a peptide sequence capable of complexing the metal. A tripeptide sequence providing an $N_3S_1$ metal ion-complexing backbone, which specifically binds a technetium or rhenium metal ion, was utilized as the starting material. To mimic the biological binding of the RGD sequence, it was determined that the two most important and primary structural aspects required for making receptor contact to the GP IIb/IIIa complex are a positively charged side chain and a negatively charged side chain analogous to the side chains of Arg and Asp residues in typical fibrinonectin peptides containing the receptor active sequence Arg-Gly-Asp (RGD sequence). Decorating the metal-peptide scaffold with these two side chains yielded the RGD mimic tetrapeptide Arg-Gly-Cys-$\beta$-Ala, which is a putative candidate for the platelet fibrinonectin receptor. Further refinements in the structure were made in response to other considerations, including stereochemistry of the side chains of the optically active amino acids, higher in vivo stability of the resulting peptide, higher blood residence time in vivo, and the ease of complexing with the metal ion in the desired configuration. Based on these considerations, a peptide of the following general formula was designed:

R$_1$-Aaa-Bbb-Ccc-Ddd-R$_2$

Where:
- Aaa=L- or D-configuration residue with a positively charged side chain, and providing an N for metal ion complexation, such as Arg, Me-Arg, N-Me-Arg, Lys, Orn, homoArg, 2,3-diamino propionic acid, 2,4,-diaminobutyric acid, S-aminoethyl cysteine, 3(O-aminotheyl) Ser, and similar derivatives and isomers of Lys, Orn, homoArg, and other similar basic amino acids.
- Bbb=L- or D-configuration residue with an uncharged side chain, and providing an N for metal ion complexation, such as Gly, Ala, Aib, Val, Nle, Leu and similar amino acids with uncharged side chains.
- Ccc=L- or D-configuration residue providing an S, and preferably an S and N, for metal ion complexation, or alternatively two Ns for metal ion complexation, such as Cys, HomoCys, Pen, His and other synthetic or derivatized amino acids.
- Ddd=L- or D-configuration residue with a negatively charged side chain, such as β-Ala, N-Me-β-Ala, higher homologues of β-Ala, Asp, N-Me-Asp, Glu, N-Me-Glu, and other synthetic or derivatized amino acids thereof, or alternatively an uncharged amino acid with a free α-carboxyl group.
- R$_1$=H, Alkyl, aryl, alkylcarbonyl, arylcarbonyl, alkyloxycarbonyl, aryloxycarbonyl, or a polymer such as PEG, PVA, or polyamino acid attached directly or through a carbonyl group.
- R$_2$=If Ddd is other than an amino acid with a free α-carboxyl group, β-Ala, N-Me-β-Ala, or a higher homologue of β-Ala, then R$_2$ is an amide or substituted amide.

Representative peptides from this series include D-Arg-Gly-D-Cys-β-Ala and PEG-CO-D-Arg-Gly-D-Cys-β-Ala. These peptides display very high affinity ($K_D$=5–10 nM) for the GP IIb/IIIa platelet receptor in a clot binding assay after their binding to reduced Tc=O [V]. Peptides not complexed to the metal ion are either inactive or have very weak activity ($K_D$=>1 mM).

The structure of the D-Arg-Gly-D-Cys-β-Ala peptide, after binding to technetium, is as follows:

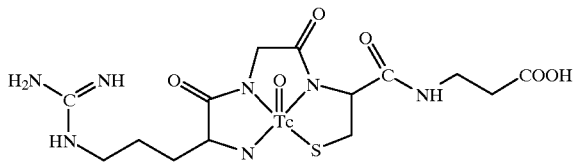

FIG. 2 shows the predicted three-dimensional backbone of the entire peptide, in a relaxed stereo view, after binding of the peptide to technetium. FIGS. 2-A and 2-B are two isomers created by the isomerism of the metaloxo group, while FIG. 2-C shows FIGS. 2-A and 2-B superimposed, demonstrating the topographic homology of biologically relevant amino acid side chains in the two isomers. The construct can similarly be bound to ReO[V] or other suitable metals, which may be either radioactive or non-radioactive.

Peptides of the following general formulas, when labeled with a metal ion, may also be employed as mimics of the RGD sequence:

R$_1$-Bbb-Aaa-Ccc-Ddd-R$_2$,

R$_1$-Bbb-Ddd-Ccc-Aaa-R$_2$, or

R$_1$-Ddd-Bbb-Ccc-Aaa-R$_2$ wherein the elements have the definitions given above for peptides of the general formula R$_1$-Aaa-Bbb-Ccc-Ddd-R$_2$.

A number of metallopeptide constructs were synthesized as mimics of the RGD sequence for various integrin receptors, such as the $\alpha_{IIb}$-$\beta_3$, $\alpha_v$-$\beta_3$, and $\alpha_5$-$\beta_1$ receptors. These constructs were synthesized to bind either $^{99m}$Tc or ReO[V]. The following constructs were synthesized, shown with an Re label (the presumptive metal ion-binding domain is shown in brackets):

ReO[V]-[Arg-Gly-Cys]-β-Ala

ReO[V]-[D-Arg-Gly-Cys]-β-Ala

ReO[V]-[Arg-Gly-D-Cys]-β-Ala

ReO[V]-[D-Arg-Gly-D-Cys]-β-Ala

ReO[V]-[D-Lys-Gly-Cys]-β-Ala

ReO[V]-[D-Lys-Gly-Cys]-Gly

ReO[V]-[Gly-Arg-Cys]-β-Ala

ReO[V]-[Gly-D-Arg-Cys]-β-Ala

ReO[V]-[Gly-Arg-D-Cys]-β-Ala

ReO[V]-[Gly-D-Arg-D-Cys]-β-Ala

ReO[V]-[D-Arg-D-Phe-D-Cys]-β-Ala

ReO[V]-[D-Arg-Gly-D-Cys]

ReO[V]-[Arg-Gly-D-Cys]

ReO[V]-C$_6$H$_5$—CH$_2$—CO-[D-Arg-Gly-D-Cys]-β-Ala

ReO[V]-[Phe-Arg-D-Cys]-β-Ala

ReO[V]-HOOC—(CH$_2$)$_2$—CO-[Phe-Gly-Cys]-Arg

ReO[V]-HOOC—(CH$_2$)$_4$—CO-[Gly-Lys-Cys]

ReO[V]-HOOC—(CH$_2$)$_5$—CO-[Gly-Lys-Cys]

Tuftsin Receptor Peptide Construct. A locally restricted peptide, in which the biological-function domain and metal-peptide backbone are combined, specific for the tuftsin receptor found on polymorphonuclear (PMN) granulocytes, monocytes and macrophages, was designed using a similar route and approach. Native tuftsin is a tetrapeptide of the sequence Thr-Lys-Pro-Arg, located as residues 289–292 of the Fc region of the heavy chain of leukokinin (a cytophilic γ-globulin). It is liberated by a combination of two cleavages. The C-terminal peptide bond is cleaved in the spleen by splenic enzyme and subsequent cleavage of the N-terminal peptide bond by enzyme leukokininase which occurs on the membranes of the granulocytes where it acts to stimulate phagocytosis. The tuftsin sequence stimulates macrophages and polymorphonuclear granulocytes towards phagocytosis. This sequence thus has a role in the immune system response for fighting infections and bacteria and other invasions. There are specific tuftsin receptors present on granulocytes and macrophages. The receptor density is approximately 50,000–100,000 per cell, with the receptor-tuftsin complex reported to internalize after binding. Thus a peptide specific for the tuftsin receptor may be used in the treatment of certain diseases, as is disclosed generally in U.S. Pat. No. 4,390,528 to V A Najjar and U.S. Pat. No. 5,028,593 to K Nishioka, the teachings of which are incorporated herein by reference. Such a peptide may also be radiolabeled with a diagnostic metal ion, such as $^{99m}$Tc, and used to determine sites of concentration of granulocytes and macrophages, such as infections and inflammations, or radiolabeled with a therapeutic metal ion, such as $^{186}$Re or $^{188}$Re, and used in the treatment of disease.

A precursor peptide of the following structure was designed, incorporating both a metal ion-binding backbone, and a biological-function domain, which biological-function domain is biologically active only upon labeling or complexing the metal ion-binding backbone with a metal ion:

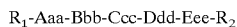

Where:

Aaa=L- or D-configuration residue selected from Thr, Cys, Pen, Pro, or Ser and corresponding des-amino derivatives.

Bbb=L- or D-configuration residue with a positively charged side chain, and containing an N for metal ion complexation, such as Arg, Lys, Orn, homoArg, S-(2-aminoethyl)Cys, O-(2-aminoethyl)Ser and other similar basic amino acids, and derivatives thereof.

Ccc=L- or D-configuration residue with an un-charged side chain, and containing an N for metal ion complexation, such as Gly, Ala, Aib, Val, Nle, Leu and similar amino acids with un-charged side chains.

Ddd=L- or D-configuration residue, providing an S, and preferably an S and N, for metal ion complexation, or alternatively two Ns for metal ion complexation, such as Cys, HomoCys, Pen, His and other synthetic or derivatized amino acids.

Eee=L- or D-configuration residue with a positively charged side chain, such as L- or D-isomers of Arg, Lys, Orn, homoArg, S-(2-aminoethyl)Cys, O-2-aminoethyl)Ser and other similar basic amino acids, and their corresponding des-carboxyl derivatives. A similar aliphatic or aromatic chain with a basic functional group can also be substituted.

$R_1$=H, Alkyl, aryl, alkylcarbonyl, arylcarbonyl, alkyloxycarbonyl, aryloxycarbonyl, or a polymer such as PEG, PVA, or polyamino acid, attached directly or through a carbonyl group. $R_1$ does not exist if Aaa is a des-amino amino acid.

$R_2$=Amide, substituted amide, ester, or a polymer such as PEG, PVA, or polyamino acid. $R_2$ does not exist if Eee is a des-carboxyl amino acid.

One representative peptide from this series includes Thr-D-Lys-Gly-D-Cys-Arg. This peptide displays very high affinity ($K_D$=1–5 nM) for human leukocytes after its binding to reduced TcO[V]. This peptide, when complexed to radioactive $^{99m}$TcO[V], localizes to the site of inflammation or infection upon i.v. administration. The affinity of the peptide which is not complexed to a metal ion is on the order of $K_D$=10$^{-4}$ M.

The structure of the Thr-D-Lys-Gly-D-Cys-Arg peptide after binding to technetium is as follows:

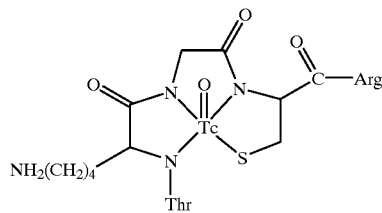

The peptide can similarly be labeled with Re. FIG. 3 shows the predicted three-dimensional backbone of the entire peptide, in a relaxed stereo view, after binding of the peptide to technetium. FIGS. 3-A and 3-B are two isomers created by the isomerism of the metaloxo group, while FIG. 3-C shows FIGS. 3-A and 3-B superimposed, demonstrating the topographic homology of biologically relevant amino acid side chains in the two isomers. Similar peptides can also be designed and synthesized using an $N_4$ metal ion-binding domain, such as Thr-D-Lys-Gly-D-His-Arg.

Globally Constrained Peptides Containing Metal-Binding Sequences. Using this invention, it is also possible to design and make globally constrained peptides, in which the biological-function domain and metal-peptide backbone are structurally distinct and can be differentiated in the molecule, but which are constructed so that complexation of a metal ion to the metal-peptide backbone constricts the conformation of the biological-function domain, so that specificity and/or affinity for the target is substantially increased upon metal ion complexation. In one embodiment, a molecule is designed which consists of a metal binding domain to replace a disulfide, lactam, or a lactone bridge in a parent peptide. The isoester moiety is designed to be placed at the location of two cysteines forming a disulfide in a peptide or the two amino acids forming a lactam or lactone bridge in a peptide. When no metal ion is complexed to the metal binding domain, the molecule exhibits higher conformational freedom than the original disulfide, or lactam or lactone bridge, thereby making the biological-function domain either biologically inactive or less potent. However, upon complexation of the metal ion to the metal binding domain, the molecule is conformationally restricted, in a manner similar to that obtained by the disulfide, or lactam, or a lactone bridge. In a biologically active molecule where these bridges are known to be crucial for bioactivity, metal complexation will restore, and may enhance, the conformation and the topography of the key receptor-recognizing and activating elements, and the desirable functionality associated therewith. The general structure of the precursor molecule and its placement in a peptide chain is as follows:

Where:

X=A complexing backbone for complexing a metal ion, the backbone containing two or more amino acids, so that all of the valences of the metal ion are satisfied upon complexation of the metal ion with X, $R_1$ and $R_2$=Each include from 0 to about 20 amino acids, $R_3$=From 1 to about 20 amino acids, Aaa and Bbb=Each comprise an amino acid connected to X through an amide, thioether or ester bond.

The sequence X can be made of amino acids containing at least one nitrogen, sulfur or oxygen atom available for complexing with the available valences of the metal ion. If less than all of the valences of the metal ion are satisfied upon complexation of the metal ion with the amino acids included in X, then X also includes a derivatized amino acid or spacer sequence, which includes at least one nitrogen, sulfur or oxygen atom available for complexing with the available valences of the metal ion, so that all of said valences of the metal ion are satisfied upon complexation of the metal ion with X. The sequence X can be an amino acid sequence of the formula Ccc-Ddd-Eee or Eee-Ddd-Ccc. In this case, each of Ccc and Ddd can be an amino acid or dipeptide with uncharged side chains, and Eee can be an L- or D-isomer of Cys, HomoCys, or Pen, His or other synthetic or derivatized amino acid containing an S, and preferably containing an S and an N or alternatively two Ns, available for binding to a metal ion. Aaa can be an L- or D-isomer of an amino acid terminating in a carboxyl group or in an amine group. Bbb is a L- or D-isomer of an amino acid terminating in a carboxyl group or in an amino group, selected such that if Bbb has a side chain terminating in a carboxyl group, Eee has a side chain terminating in an amino group, and if Bbb has a side chain terminating in an amino group, Eee has a side chain terminating in a carboxyl group.

The precursor molecule for isosteric replacement of a disulfide, lactam or lactone bridge thus includes constructs on the following models:

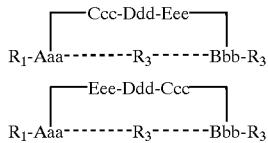

Where:
- Aaa and Bbb=L- or D-isomers of amino amino acids with a side chain terminating either in a carboxyl group, such as Asp, Glu or similar synthetic amino acids, or in an amino group, such as Orn, Lys, or similar unnatural amino acids. If Aaa is a carboxyl group, then Bbb is an amino group, and if Aaa is an amino group, then Bbb is a carboxyl group.
- Ccc and Ddd=L- or D-isomers of Gly, Ala, Aib, Val, Nle, Leu, or similar amino acids with uncharged side chains, or a dipeptide comprising any of these amino acids. Aaa is also a dipeptide composed of a combination of these amino acids.
- Eee=L- or D-isomers of amino acids containing an S for complexing with a metal ion, and preferably an S and an N for complexing with a metal ion, and alternatively two Ns for complexing with a metal ion, such as Cys, HomoCys, Pen, His or similar synthetic or derivatized amino acids.
- $R_1$, $R_2$ and $R_3$=$R_1$ and $R_2$ are from 0 to about 20 amino acid residues, and $R_3$ is from 1 to about 20 amino acid residues, all or any portion of which makes up all or part of the biological-function domain. The biological-function domain may be sychnological or rhegnylogical.

Formulation of Radiopharmaceutical Kits. One application of this invention is to provide peptides for use as radiopharmaceuticals, either diagnostic agents labeled with radioisotopes such as $^{99m}$Tc $^{111}$In, or therapeutic agents labeled with radioisotopes such as $^{188}$Re or $^{186}$Re. $^{99m}$Tc is generally obtained as sodium pertechnetate, and rhenium as perrhenate. In both instances, it is necessary to reduce the pertechnetate or perrhenate to a lower oxidation state so that the metal ion complexes with the peptide. Stannous (also referred to herein as "Sn (II)") may be effectively used for this purpose. Sources of Sn (II) include stannous tartrate, stannous glucoheptonate, stannous gluconate, stannous phosphonate, stannous chloride, stannous sulfate, stannous acetate, and stannous fluoride. The selection of the source of Sn (II) and its final concentration depends on the intended medical application of the peptide, the nature of the peptide, and the metal ion to be used. For example, a significantly higher stannous concentration is required to reduce perrhenate than to reduce pertechnetate. $^{188}$Re in the form of perrhenate may be labeled using kits with between about 2.5 to 15 mM stannous, with total tin correspondingly ranging from about 1 to 5 mg or higher if a larger volume kit is employed, all at a pH of between about 5 and 6. Generally speaking, lower stannous concentration kits require heating, such as for 30 to 60 minutes in a boiling bath, to effectively reduce all the available perrhenate, while high total tin kits have sufficient reduction capacity to reduce the perrhenate within about one hour when incubated at room temperature. Increasing the stannous concentration above about 15 mM has negligible effects on reduction capacity, and at higher concentrations it becomes increasingly difficult to keep the stannous in solution.

For either $^{186}$Re or $^{188}$Re labeling, approximately 5 mM of stannous tartrate, for a total tin concentration of approximately 1.2 mg, was employed with 200 μg of peptide. For labeling the same quantity of peptide with $^{99m}$Tc, approximately 0.5 mM of stannous tartrate was employed. The amount of Sn (II) in the preparation must be such as to be sufficient to completely reduce the metal ion to the desired redox state under the specified reaction conditions, without having such Sn (II) concentrations that the tin precipitates from the solution. Precipitation can be, in large part, controlled by the selection of appropriate buffers and complexing agents. The quantity of Sn (II) also varies with the reaction conditions; for example, with preparations which are incubated at temperatures in the range of 80° C. to 100° C., less Sn (II) is required than if incubation is effected at room temperature. The incubation time also varies depending on the incubation conditions, principally temperature, although pH and other conditions also affect incubation time. Generally speaking, incubation at temperatures in the range of 80° C. to 100° C. are substantially shorter than incubations at room temperature, requiring an incubation period from one-half to one-tenth or less in length.

For labeling with pertechnetate, it is possible to use between 0.2 and 1 mM of stannous, and preferably from 0.5 to 1 mM stannous, with total tin as low as 40 μg, depending upon the fill volume.

Regardless of the method employed, the form of stannous employed depends in part on the buffers utilized in the kits. For example, in kits with buffers containing tartrate as a complexing agent, use of stannous tartrate salt is desirable. For kits containing complexing agents other than tartrate, such as kits containing EDTA, stannous chloride dihydrate may be employed. Generally speaking, all stannous is added in concentrated hydrochloric acid. This favors maintaining the tin in the Sn (II) oxidation state, as stannous ions, rather than the Sn (IV) state, as stannic ions. Sn (II) effectively reduces radiometals such as pertechnetate or perrhenate, while Sn (IV) does not. Complexing agents are generally used in a 2 to 20 molar excess over the total tin, to insure that all of the tin, including both stannous ion and any stannic ion, will be complexed. Uncomplexed tin at neutral pH readily forms an insoluble hydroxide. In the absence of complexing agents, above pH 5.5 colloidal tin species may be formed before the hydroxide precipitates. Complexing agents sequester tin from the hydrolysis reaction, but do not prevent tin from entering into redox reactions. pH titrations of stannous solutions have shown increasing complexing ability with EDTA>>citrate>>glucoheptonate>>tartrate>>malic acid. Though stannous tartrate exists as a 1:1 molar ratio of tin:tartrate as the dry salt, empirical evidence suggests that a minimum 2-fold excess of tartrate is necessary to stabilize stannous at neutral pH. However, EDTA, citrate and glucoheptonate can all stabilize stannous at approximately 1:1 molar ratios at neutral pH; a working formula of 1.2:1 molar ratio of complexing agent:stannous can be satisfactorily utilized.

Regardless of the method employed, high concentrations of tin may be stabilized through the use of appropriate buffers. For example, metal binding buffers, such as diglycine and triglycine at 50 to 100 mM, can increase the stability of high millimolar tin concentrations at neutral pH. For example, a buffer containing 50 mM diglycine or triglycine, with an appropriate complexing agent such as EDTA, citrate, glucoheptonate or tartrate, can be used to stabilize the tin, and prevent precipitation, when the total tin concentration is in the range of 5 to 10 mM. Suitable metal ion buffers include citrate and tartrate, polyaminocarboxylic acids such as EDTA, DTPA and NTA (nitrilotriacetic acid), ACES (N-2-acetamido-2-aminoethanesulfonic acid), ADA (N-2-acetamidoiminodiacetic acid), bicine, tricine, glycylglycine, triglycine, tetraglycine, and MES (2-(N-morpholino)ethanesulfonic acid). For example, it is possible to stabilize a high millimolar stannous solution, comprising 5 mM stannous tartrate in 40 mM KH Phthalate and 10 mM NaK tartrate, at neutral pH and above by addition of a second metal binding buffer, such as glycylglycine, which has a pKa of 8.2, at concentrations from 50 to 100 mM. Generally speaking, the solubility of stannous is enhanced by addition of a second metal binding buffer which has a pKa at or close to the pH of the composition to be radiolabeled. For example, if a radiolabeling composition contains tartrate, which has a pKa of 4.3, and if the composition is to be radiolabeled at a pH significantly different from 4.3, then increased tin complexation, with resultant stability of the tin and protection from precipitation, can be achieved by addition of a second metal binding buffer with a pKa at or near the pH of the composition to be radiolabeled.

Depending on the peptide employed, formulation and reaction conditions must be altered, and can be determined empirically for any given peptide of this invention. In general, complexing or buffering agents will yield different results with different peptides. For example, one peptide construct may be used with SnCl$_2$-tartrate-phthalate, at a ratio of 1–10–40 mM at pH 5.5, in a vial containing 5 μg of peptide in a fill volume of 400 μL, yielding good results when labeled with $^{99m}$Tc as sodium pertechnetate. Another peptide may have radiochemical impurities, or not label completely, using this reducing and buffering solution, but may yield good results with SnCl$_2$-succinate-EDTA, at a ratio of 1–20–1.2 mM at pH 6.2, in a vial containing 5 μg of peptide in a fill volume of 400 μL. Yet another peptide may yield good results with glucoheptonate-Sn, at a ratio of 0.2–1 mM at pH 7.5 to 8.0, in a vial containing 1 to 5 μg of peptide in a fill volume of 400 μL. Other reducing and buffering solutions may similarly be employed, and determined for each particular peptide.

In a given case, the tartrate concentration can range from below 10 mM to over 50 mM. The buffer, such as potassium hydrogen phthalate, can range from over 40 mM to less than 10 mM. Potassium hydrogen phthalate at a 10 mM concentration, and in some instances a lower concentration, is sufficient to yield acceptable radiolabeling results while affording a higher glass transition temperature for facile freeze drying.

A variety of excipients and other agents may be employed as needed. These include agents to increase solubility of certain peptides, lyophilization excipients, and the like. Maltose, inositol, manitol, and other sugars can be added freeze-drying excipient.

In general, quantities as low as 1–5 μg of peptide of this invention may be labeled with $^{99m}$Tc or rhenium using the methods described above. Since only radiolabeled peptide is biologically active, the amount required is, in part, dependent on the quantity of metal ions to be added. For many radiopharmaceutical applications, the peptide should be in a 2- to 20-fold excess over the quantity of metal ions, to insure that all metal ions are incorporated into a peptide molecule. However, for non-radiopharmaceutical applications, the metal ion can be in significant excess over the quantity of peptide, to insure that all peptide molecules have incorporated a metal ion. For such non-radiopharmaceutical applications, the quantity of peptide labeled with metal ion may be as large as is desired.

Most prior art radiopharmaceutical methods involve peptide formulations of 100 μg and higher. The methods of this invention can be used in radiopharmaceutical preparations in formulations containing 5 μg or less, with acceptable radiolabeling obtained with preparations containing as little as 1 μg, and in which the biologically active portion, based on the percentage of total peptide complexed with a metal ion, is from less than 1% to approximately 20% of the total peptide in the formulation. Thus, the amount of total peptide used in a formulation is very low, and the amount of biologically active peptide in the formulation upon labeling with a metal ion is even lower still, by from roughly 5- to 100-fold or less. Use of very small amounts of peptide minimizes dimerization and other aggregation of the peptide, results in very high specific activity, at or near theoretical limits, and provides for much lower toxicity or undesired biological activity, by minimizing the amount of biologically active peptide in the formulation.

The radiopharmaceutical products of this invention are conveniently radiolabeled by adding the radionuclide to a vial containing the peptide, Sn (II), buffers and other excipients. After addition of the radionuclide the solution is allowed to incubate for a period of from 15 minutes to 4 hours, and at a temperature ranging from room temperature to 100° C. After radiolabeling, the product may be tested by HPLC, including reversed phase HPLC with a UV and radioisotope detector in series, by thin layer chromatography or by other means known in the art. The products of this invention will typically have less than 5% radiochemical impurities, and frequently less than 2% radiochemical impurities, the impurities consisting of uncomplexed or unreduced radionuclide, colloids and the like.

The invention is further illustrated by the following non-limiting examples.

EXAMPLE 1
Design and Synthesis of RGD Receptor-Specific Peptide

A molecule based on the receptor binding characteristics of Arg-Gly-Asp (RGD) was designed. Based on a peptide N$_3$S$_1$ metal ion-binding backbone, and modifying and decorating the backbone to arrive at a construct similar to the receptor binding region of RGD, the peptide D-Arg-Gly-D-Cys-β-Ala was designed, and was synthesized by conventional solid phase peptide synthesis. In brief, Fmoc-β-Ala was coupled to 4-alkoxybenzyl alcohol resin, a peptide synthesis resin. After the removal of the Fmoc group by treatment with piperidine, the peptide chain was elongated successively using Fmoc-D-Cys(Trt), FmocGly, and Fmoc-D-Arg(Pmc). The Fmoc group from the resulting peptide-resin, Fmoc-D-Arg(Pmc)-Gly-D-Cys(Trt)-β-Ala-Resin, was removed. Fully unprotected peptide was released from the resin by treatment with TFA. The peptide was purified by reversed phase HPLC and obtained as a lyophilized white powder. Fast-atom mass spectrometric analysis gave the correct mass for the synthesized peptide.

EXAMPLE 2
Alternate Synthesis Method of RGD Receptor-Specific Peptide

The peptide D-Arg-Gly-D-Cys-β-Ala is synthesized by alternate solid phase methods using Boc protected amino acids. In this approach, Boc-β-Ala is first coupled to Merrifield resin or PAM-resin. The Boc group is then removed by treatment with TFA and the peptide chain elongated using successive amino acids, Boc-D-Cys(MeBzl), Boc-Gly, and Boc-D-Arg(Tos). The fully synthesized protected peptide-resin, Boc-D-Arg(Tos)-Gly-D-Cys(MeBzl)-β-Ala-Resin, is then treated with HF to liberate the fully unprotected peptide. The peptide is then purified by reversed phase HPLC.

EXAMPLE 3
Alternate Synthesis Method of RGD Receptor-Specific Peptide

The peptide D-Arg-Gly-D-Cys-β-Ala is also synthesized by conventional methods of solution-phase peptide synthesis. In brief, Boc-D-Cys(MeBzl) is coupled to β-Ala-OEt using a coupling agent such as DCC-HOBt. The Boc group is cleaved by treatment of the resulting dipeptide Boc-D-Cys(MeBzl)-β-Ala-OEt with TFA. It is then coupled to Boc-Gly using a similar approach. After the removal of the Boc group from the resulting tripeptide Boc-Gly-D-Cys(MeBzl)-β-Ala-OEt and subsequent coupling with Boc-D-Arg(Tos), a fully protected tetrapeptide is obtained. The C-terminal ester group is saponified and the resulting peptide treated with HF to result in fully unprotected peptide which is purified by reversed phase HPLC.

EXAMPLE 4
Preparation of D-Arg-Gly-D-Cys-β-Ala Conjugated to Higher Molecular Weight Molecules The D-Arg-Gly-D-Cys-β-Ala peptide of Example 1 was conjugated to various forms of polyethylene glycol (PEG) to obtain higher molecular weight constructs for biodistribution studies. PEG of various molecular weights (100–8000) and mono-methoxy PEG of similar molecular weights was activated with disuccinimide carbonate according to the teachings of S. Zalipsky (*Bioconjugate Chemistry* 4:296–299, 1993). The activated PEG was then treated with the peptide D-Arg-Gly-D-Cys-β-Ala taken in phosphate buffer (125 mM, pH 6.5) in presence of 1 mM HOBt. After 1 hour at room temperature, the reaction mixture was extracted several times with dichloromethane. The combined organic extract was washed once with water and evaporated to dryness. The product was then precipitated by the addition of anhydrous ether. The product was purified once by precipitation from an ethanol-ether system. The following constructs were synthesized in this manner: [PEG$_{8000(M/W)}$]-(D-Arg-Gly-D-Cys-β-Ala)$_2$, [Me-PEG$_{5000(M/W)}$]-D-Arg-Gly-D-Cys-β-Ala, and [Me-PEG$_{2000(M/W)}$]-D-Arg-Gly-D-Cys-β-Ala.

EXAMPLE 5
Radiolabeling and Formulation of Radiopharmaceutical Kits Using D-Arg-Gly-D-Cys-β-Ala and Stannous-Tartrate-Phthalate Direct Labeling. The D-Arg-Gly-D-Cys-β-Ala peptide obtained as set forth in Example 1 was labeled with $^{99m}$Tc in the presence of stannous as a reducing agent in a tartrate-phthalate buffer. 100 µg of the peptide was mixed with generator eluted $^{99m}$Tc-sodium pertechnetate (1–35 mCi of radioactivity in up to 500 µL volume). To this was added a nitrogen purged solution (400 µL) of stannous-tartrate-phthalate (1 mM–10 mM–40 mM, pH 6.1). The head space of the vial was purged with nitrogen and the solution left at room temperature for 30 minutes A small aliquot of this $^{99m}$Tc labeled peptide was analyzed by reversed phase HPLC on a C-18 column (VYDAC, Cat. No. 218TP104). A gradient of 0–20% acetonitrile completed in 30 minutes at a flow rate of 1.5 mL/minute was employed. The radioelution profile was generated by a radio-detection flow cell system attached to the HPLC. The profile indicated that the $^{99m}$Tc-labeled peptide eluted at 11.1 minutes. A small amount of radiolabeled fraction was also present that eluted at 13.8 minutes, which may be a dimeric species composed of 2:1 peptide-$^{99m}$Tc complex. The profile also indicated that the detectable amount of reduced $^{99m}$Tc that eluted with the solvent peak (retention time 2.2 minutes), if any, was no more than 4%. A 10 µCi sample of the labeled preparation was spotted on an instant thin layer chromatography (ITLC) strip (1.5×10 cm. silica gel impregnated strips, Gelman Science, Ann Arbor, Mich.) and developed with 150 mM NaCl. Radioactivity measurements on this strip revealed that the origin had only 2–4.5% of radioactivity, which corresponds to the amount of $^{99m}$Tc colloid present in the preparation. The labeled preparation, when stored at room temperature for up to 36 hours, did not show any change in its HPLC and ITLC profiles. The HPLC and ITLC results together suggest a very good $^{99m}$Tc labeling profile for this peptide.

Kit Formulation. A radiopharmaceutical kit was formulated using the same buffer system. Each vial contained 100 µg of the D-Arg-Gly-D-Cys-β-Ala peptide of Example 1 and a nitrogen purged solution (200–400 µL) of stannous-tartrate-phthalate (1 mM–10 mM–40 mM, pH 6.1). The kits were stored under refrigeration, and some kits were lyophilized. The lyophilized vials were backfilled with nitrogen and sealed. To label either the refrigerated vials or the lyophilized vials, the contents of the vial were mixed with generator-eluted $^{99m}$Tc-sodium pertechnetate (1–35 mCi of radioactivity in up to 500 µL volume), and the solution was left at room temperature for 30 minutes. Substantially similar radiochemical yields and profiles were obtained with these kits.

Kits were formulated with as little as 5 µg of the D-Arg-Gly-D-Cys-β-Ala peptide of Example 1 and a nitrogen-purged solution (200–400 µL) of stannous-tartrate-phthalate (1 mM–10 mM–40 mM, pH 6.1). Kits with 5 µg of D-Arg-Gly-D-Cys-β-Ala were labeled with 2 mCi of $^{99m}$Tc and the equivalent of 50 mCi of $^{99m}$Tc as 99Tc, for a metal ion concentration equivalent to 52 mCi of $^{99m}$Tc, with no significant radiochemical impurities. The ratio of metal ion to peptide was 1:22 with 52 mCi equivalent of $^{99m}$Tc. By increasing the quantity of $^{99}$Tc, successful labeling was achieved at as low as a 1:8 metal ion-to-peptide ratio using 5 µg kits, and at as low as a 1:2 ratio using 2 µg kits.

PEG Conjugated Product Labeling. The products of Example 4 were directly labeled by the method described above, with similar radiochemical yields and profiles obtained. The elution times necessarily varied depending on the form of PEG employed as a conjugate.

Alternate Synthesis Peptide. The method of radiolabeling is independent of the origin of the peptide, and may be employed as described above with peptides made using the methods of any of Examples 2 or 3.

EXAMPLE 6
Radiolabeling and Formulation of Radiopharmaceutical Kits Using D-Arg-Gly-D-Cys-β-Ala and Stannous-Tartrate-Phthalate-Glycylglycine Direct Labeling. The D-Arg-Gly-D-Cys-β-Ala peptide obtained as set forth in Example 1 was labeled using stannous as a reducing agent for $^{99m}$Tc-sodium pertechnetate, with the stannous stabilized in a tartrate-phthalate-glycylglycine buffer. The general methodology was similar to that of Example 5 except that a nitrogen purged solution (200–400 μL) of stannous-tartrate-phthalate-glycylglycine (1 mM–10 mM–40 mM–50 mM, pH 6.6) was used. Labeling efficiency results similar to those in Example 5 were obtained using the same HPLC and ITLC techniques.

Kit Formulation. A radiopharmaceutical kit is formulated using the same buffer system. Each vial contains from 1 to 100 μg of the D-Arg-Gly-D-Cys-β-Ala peptide of Example 1 and a nitrogen-purged solution (200–400 μL) of stannous-tartrate-phthalate-glycylglycine as set forth above. For some kits, excipients are added, including maltose, manitol, and other sugars. The kits are stored under refrigeration, or are optionally lyophilized. The lyophilized vials are backfilled with nitrogen and sealed. To label either the refrigerated vials or the lyophilized vials, the contents of the vial are mixed with generator-eluted $^{99m}$Tc-sodium pertechnetate (1–35 mCi of radioactivity in up to 500 μL volume).

PEG Conjugated Product Labeling. The products of Example 4 are directly labeled by the methods described in this Example.

Alternate Synthesis Peptide. The method of radiolabeling of this Example is independent of the origin of the peptide, and may be employed as described above with peptides made using the methods of any of Examples 2 or 3.

EXAMPLE 7
Radiolabeling and Formulation of Radiopharmaceutical Kits Using D-Arg-Gly-D-Cys-β-Ala and Stannous-Tartrate-Succinate Direct Labeling. The D-Arg-Gly-D-Cys-β-Ala peptide obtained as set forth in Example 1 was labeled using stannous as a reducing agent for $^{99m}$Tc-sodium pertechnetate, with the stannous stabilized in a tartrate-succinate buffer. The general methodology was similar to that of Example 5 except that a nitrogen purged solution (200–400 μL) of stannous-tartrate-succinate (1 mM–10 mM–20 mM, pH 6.2) was used. Labeling efficiency results similar to those in Example 5 were obtained using the same HPLC and ITLC techniques.

Kit Formulation. A radiopharmaceutical kit is formulated using the same buffer system. Each vial contains from 1 to 100 μg of the D-Arg-Gly-D-Cys-β-Ala peptide of Example 1 and a nitrogen-purged solution (200–400 μL) of stannous-tartrate-succinate as set forth above. The kits may be lyophilized, with the lyophilized vials backfilled with nitrogen and sealed. To label, the contents of the vial are mixed with generator-eluted $^{99m}$Tc-sodium pertechnetate (1–35 mCi of radioactivity in up to 500 μL volume).

PEG Conjugated Product Labeling. The products of Example 4 are directly labeled by the methods described in this Example.

Alternate Synthesis Peptide. The method of radiolabeling of this Example is independent of the origin of the peptide, and may be employed as described above with peptides made using the methods of any of Examples 2 or 3.

EXAMPLE 8
Radiolabeling and Formulation of Radiopharmaceutical Kits Using D-Arg-Gly-D-Cys-β-Ala and Stannous-Edta-Succinate Direct Labeling. The D-Arg-Gly-D-Cys-β-Ala peptide obtained as set forth in Example 1 was labeled using stannous as a reducing agent for $^{99m}$Tc-sodium pertechnetate, with the stannous stabilized in an EDTA-succinate buffer. The general methodology was similar to that of Example 5 except that a nitrogen purged solution (200–400 μL) of stannous-EDTA-succinate (1 mM–1.1 mM–20 mM, pH 6.2) was used. Labeling efficiency results similar to those in Example 5 were obtained using the same HPLC and ITLC techniques.

Kit Formulation. A radiopharmaceutical kit is formulated using the same buffer system. Each vial contains 1 to 100 μg of the D-Arg-Gly-D-Cys-β-Ala peptide of Example 1 and a nitrogen purged solution (200–400 μL) of stannous-EDTA-succinate as set forth above. Excipients may be added, and the kits lyophilized and backfilled with nitrogen and sealed. To label, the contents of the vial are mixed with generator eluted $^{99m}$Tc-sodium pertechnetate (1–35 mCi of radioactivity in up to 500 μL volume).

PEG Conjugated Product Labeling. The products of Example 4 are directly labeled by the methods described in this Example.

Alternate Synthesis Peptide. The method of radiolabeling of this Example is independent of the origin of the peptide, and may be employed as described above with peptides made using the methods of any of Examples 2 or 3.

EXAMPLE 9
Radiolabeling and Formulation of Radiopharmaceutical Kits Using D-Arg-Gly-D-Cys-β-Ala and Glucoheptonate The D-Arg-Gly-D-Cys-β-Ala peptide obtained as set forth in Example 1 was labeled using stannous as a reducing agent for $^{99m}$Tc-sodium pertechnetate, with the stannous stabilized in glucoheptonate, which also served as a transchelation agent. To label, a solution of the peptide (100 μg in 100 μL saline) was added to a GlucoScan (DuPont, Wilmington, Del.) kit freshly reconstituted with 1–35 mCi of $^{99m}$Tc-sodium pertechnetate (200–500 μL) for 10 minutes at room temperature. The reaction mixture was allowed to stand at room temperature and was then analyzed by HPLC and ITLC techniques as described in Example 5. Labeling efficiency results similar to those in Example 5 were obtained using the same HPLC and ITLC techniques.

EXAMPLE 10
Radiolabeling and Formulation of Radiopharmaacetical Kits Using D-Arg-Gly-D-Cys-β-Ala and Stannous-Borate-Tartrate The D-Arg-Gly-D-Cys-β-Ala peptide obtained as set forth in Example 1 was labeled using stannous as a reducing agent for $^{99m}$Tc-sodium pertechnetate, with the stannous stabilized in borate-tartrate buffer. The general methodology was similar to that of Example 5 except that a nitrogen purged solution (200–400 μL) of stannous-borate-tartrate (1 mM–50 mM–20 mM, pH 9.3) was used. Labeling efficiency results similar to those in Example 5 were obtained using the same HPLC and ITLC techniques.

EXAMPLE 11
Saturation Binding of $^{99m}$Tc-[D-Arg-Gly-D-Cys]-β-Ala to Platelets Saturation binding of $^{99m}$Tc-labeled D-Arg-Gly-D-Cys-β-Ala peptide to human platelets was demonstrated using a freshly prepared preparation of platelet rich plasma (PRP). The concentration of platelets in PRP was adjusted using PPP to a final value of 3×10$^8$ platelets/mL per each assay tube. Increasing amounts of $^{99m}$Tc-labeled peptide were added to constant amounts of PRP taken in different assay tubes. This was followed by the addition of ADP to a final concentration of 10 μM in order to activate the platelets. Similar volumes of PPP were used at each concentration of the $^{99m}$Tc-labeled peptide as a measure of the non-specific binding component under the experimental conditions. Binding was allowed to take place for 30 minutes after which the tubes were transferred to an ice bath. A 200 μL aliquot corresponding to 0.6×10$^8$ platelets was filtered through a glass fiber filter that was presoaked in PPP for 30 minutes. The filters were then washed three times with 1 mL of PBS and counted in a gamma counter for the bound radioactivity. The data was normalized to account for the decay of $^{99m}$Tc and plotted. An analysis of the data gave a value for $K_D$ in the range of 5–10 nM for the $^{99m}$Tc-labeled D-Arg-Gly-D-Cys-β-Ala peptide.

Figure 4:
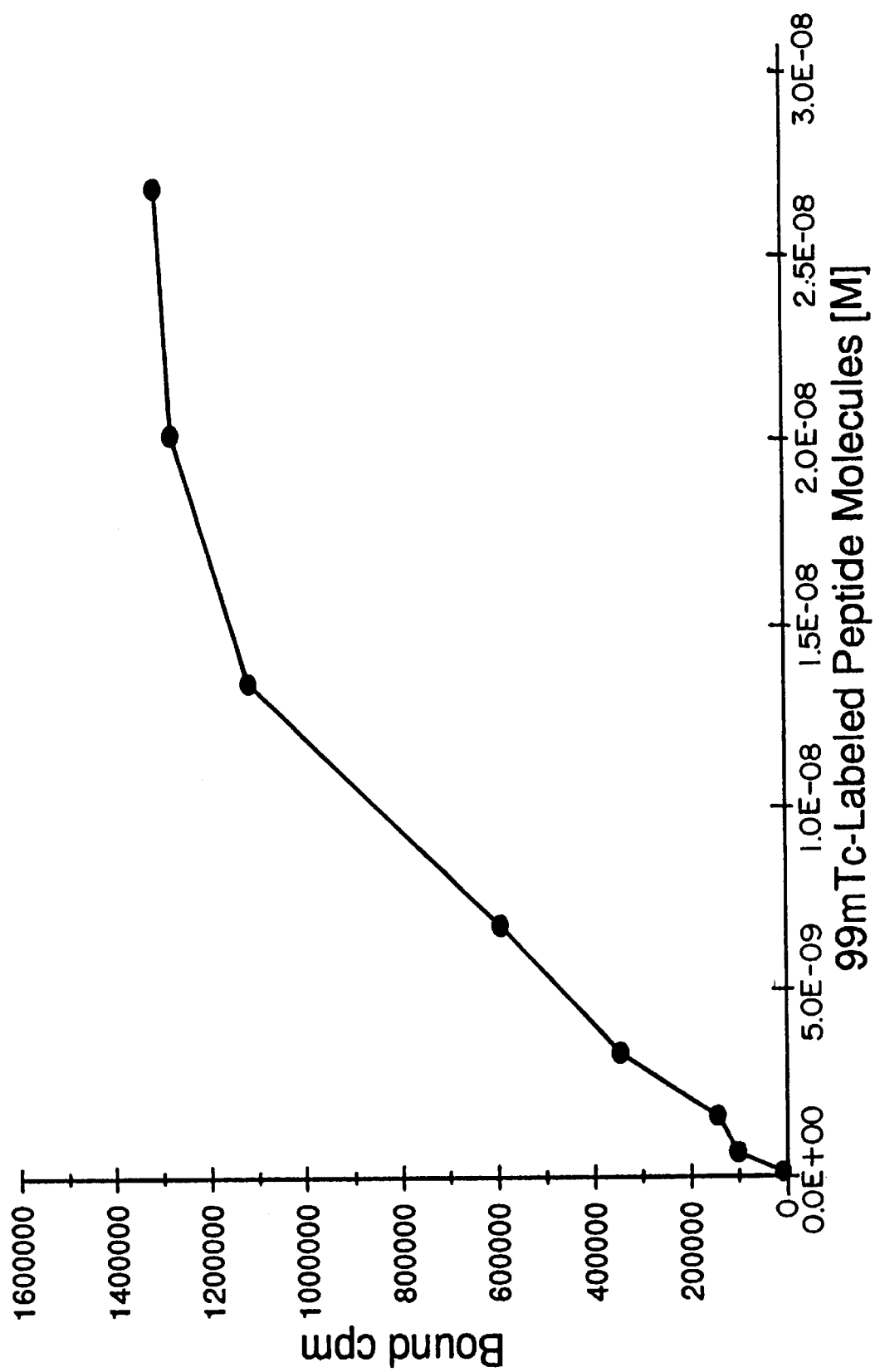
FIG. 4 shows a saturation binding isotherm of binding of $^{99m}$Tc-labeled D-Arg-Gly-D-Cys-β-Ala with human activated platelets.

EXAMPLE 12
Saturation Binding of $^{99m}$Tc-[D-Arg-Gly-D-Cys]-β-Ala to Fixed Platelets Saturation binding of $^{99m}$Tc-labeled D-Arg-Gly-D-Cys-β-Ala peptide to ADP-activated and formalin-fixed human platelets was demonstrated using a preparation of platelet rich plasma (PRP) that was prepared according to the teachings of U.S. Pat. No. 5,332,726, incorporated herein by reference, except that ADP (10 μM final concentration) was used instead of thrombin to activate the platelets. The concentration of fixed platelets obtained in this manner was adjusted using PPP to a final value of 3×10$^8$ platelets/mL per each assay tube. Increasing amounts of $^{99m}$Tc-labeled peptide were added to these constant amounts of fixed platelets taken in different assay tubes. Similar volumes of PPP were used in respect to each concentration of the $^{99m}$Tc-labeled peptide as a measure of the non-specific binding component under the experimental conditions. The binding was allowed to take place for 30 minutes and the assay subjected to the protocol as described in Example 11. The data obtained in this case was also normalized to account for the decay of $^{99m}$Tc and plotted. The results demonstrate saturation binding kinetics of the peptide for its activated platelet receptor as is shown in FIG. 4. The X-axis shows the actual fraction of $^{99m}$Tc-labeled molecules of the total peptide molecules, with only the $^{99m}$Tc-labeled molecules presumed to have biological activity. analysis of the data gave a value for $K_D$ in the range of 5–10 nM for the $^{99m}$Tc-labeled D-Arg-Gly-D-Cys-β-Ala peptide, comparable to the results obtained in Example 11.

EXAMPLE 13
Saturation Binding of $^{99m}$Tc-[D-Arg-Gly-D-Cys]-β-Ala to Clots Saturation binding of $^{99m}$Tc-labeled D-Arg-Gly-D-Cys-β-Ala peptide of Example 5 to blood clots was demonstrated using freshly prepared human blood clots. 100 μL aliquots of the freshly drawn human blood were placed in glass tubes and allowed to incubate at room temperature for 1.5 hours. After further incubation for 30 minutes at 4° C., the clots which had formed were washed three times with 1 mL of 1 mM EDTA in PBS. Increasing amounts of $^{99m}$Tc-labeled peptide were added to these clots in triplicates. Empty glass tubes were included in the assay as a measure of non-specific binding component under the experimental conditions. The binding was allowed to take place for 60 minutes at room temperature. All the tubes were then transferred to an ice bath. 1 mL of ice cold PBS was added to each tube and the clots washed by aspirating off the PBS. The clots were further washed three more times with 1 mL of PBS in a similar manner and the tubes containing the clots counted for bound radioactivity in a gamma counter. The data obtained in this manner were normalized to account for the decay of $^{99m}$Tc and plotted. The results revealed the saturation binding kinetics of the peptide for its activated platelet receptor on the platelets embedded in the clots. An analysis of the data gave a value for $K_D$ in the range of 5–10 nM for the $^{99m}$Tc-labeled D-Arg-Gly-D-Cys-β-Ala peptide, comparable to the results obtained in Examples 11 and 12.

EXAMPLE 14
Saturation Binding of $^{99m}$Tc-[D-Arg-Gly-D-Cys]-β-Ala to Clots Using Carrier Free Preparation Saturation binding of a carrier-free preparation of $^{99m}$Tc-labeled D-Arg-Gly-D-Cys-β-Ala peptide to blood clots was demonstrated, using the methods of Example 13. The carrier-free preparation of the $^{99m}$Tc-labeled peptide was prepared by passing a freshly labeled preparation of $^{99m}$Tc-labeled peptide of Example 5 through an affinity column composed of a solid phase (agarose or polystyrene beads) to which a thiol reacting group has been attached. Maleimide bound to polystyrene and bromoacetylated dextrose resins used for this purpose were obtained from commercial sources. These functionalities of the resin are reactive towards the thiol groups of the Cys residue in the peptide. As a consequence, the molecules of the peptide that were not bound to $^{99m}$Tc atom were irreversibly retained on the column. The effluent from the column therefore contained the pure $^{99m}$Tc-labeled molecules of the peptide. This preparation was used in a clot binding experiment as described in Example 13. An analysis of the data yielded a value for $K_D$ in the range of 5–10 nM. These results were very much comparable with those obtained in Examples 11 through 13, confirming that it was the $^{99m}$Tc-labeled fraction of the peptide that was biologically active, and exhibited receptor binding.

EXAMPLE 15
Saturation Binding of PEG-$^{99m}$Tc-[D-Arg-Gly-D-Cys]-β-Ala to Clots Saturation binding of $^{99m}$Tc-labeled PEG$_{8000}$-D-Arg-Gly-D-Cys-β-Ala peptide of Example 4 to blood clots was demonstrated using freshly prepared human blood clots in a manner similar to that described in Example 13. The PEG-conjugated peptide was labeled with $^{99m}$Tc according to the methods described in Example 5. The results gave a value for $K_D$ in the range of 5–20 nM for $^{99m}$Tc-labeled PEG$_{8000}$-D-Arg-Gly-D-Cys-β-Ala peptide, comparable to the results obtained in Examples 11 through 14.

Figure 5:
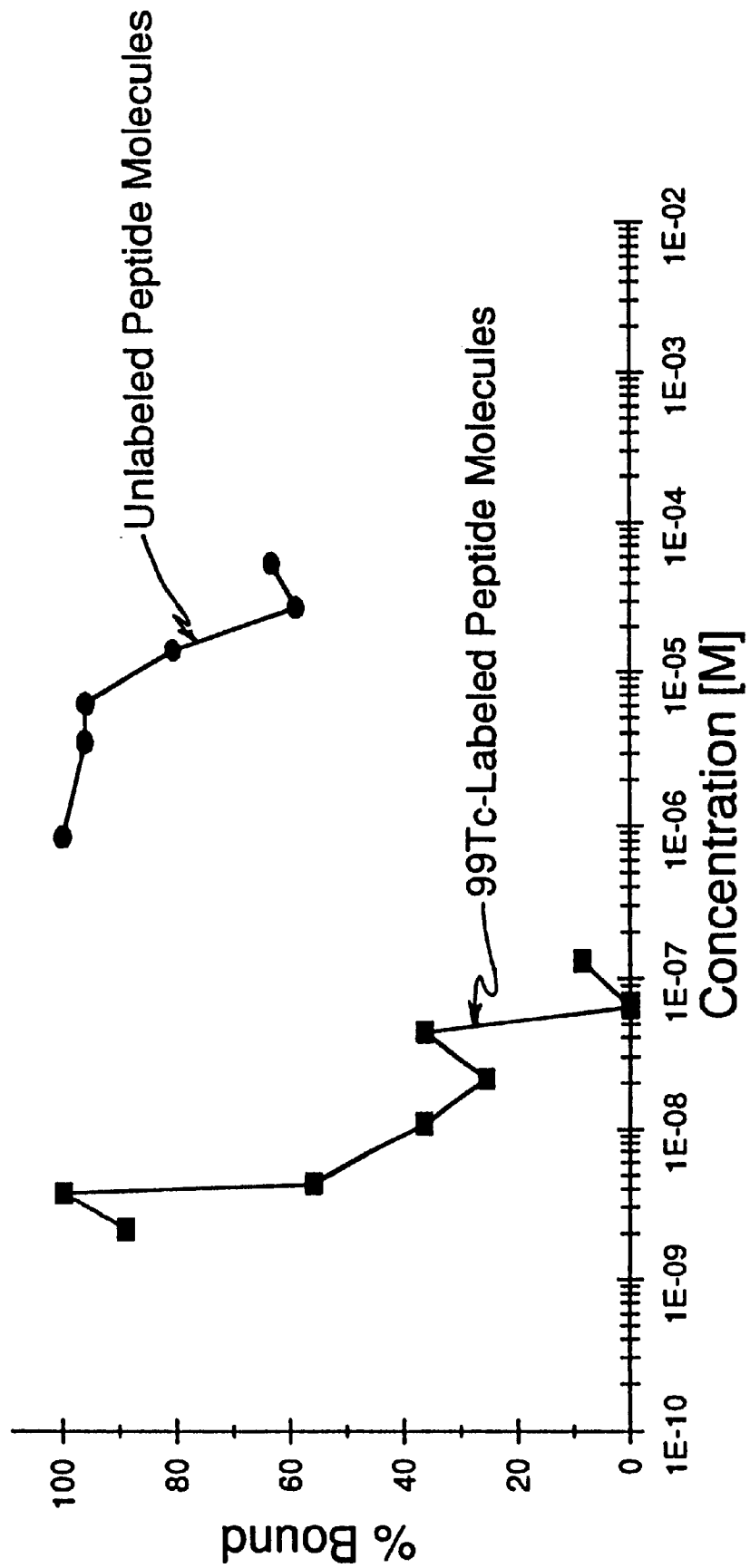
FIG. 5 shows results of competition binding of $^{99}$Tc-labeled D-Arg-Gly-D-Cys-β-Ala and unlabeled D-Arg-Gly-D-Cys-β-Ala with $^{99m}$Tc-labeled D-Arg-Gly-D-Cys-β-Ala for binding to human platelets.

EXAMPLE 16
Competition of Cold $^{99m}$Tc-[D-Arg-Gly-D-Cys]-β-Ala With $^{99m}$Tc-[D-Arg-Gly-D-Cys]-β-Ala in Binding Assays Activated and formalin-fixed platelets (3×10$^8$ platelets/mL per assay tube), as described in Example 12, were incubated with a mixture of $^{99m}$Tc-labeled D-Arg-Gly-D-Cys-β-Ala and $^{99m}$Tc-labeled D-Arg-Gly-D-Cys-β-Ala peptide. A constant but trace amount of the $^{99m}$Tc-labeled peptide was used in this assay. The amount of $^{99m}$Tc-labeled peptide, however, varied between 10$^{-9}$ M to 10$^{-7}$ M in terms of the $^{99}$Tc-labeled fraction of the total peptide molecules. Both the $^{99m}$Tc-labeled and the $^{99}$Tc-labeled peptides were prepared according to the methods of Example 5. This data demonstrates binding inhibition with the $^{99}$Tc-labeled peptide, and yields an $IC_{50}$ in the range of 5–10 nM for the $^{99m}$Tc-peptide. FIG. 5 depicts the binding curve obtained in this experiment for $^{99}$Tc-labeled peptide.

EXAMPLE 17

Competition of D-Arg-Gly-D-Cys-β-Ala With $^{99m}$Tc-[D-Arg-Gly-D-Cys]-β-Ala in Binding Assays This study was conducted as set forth in Example 16, except that D-Arg-Gly-D-Cys-β-Ala peptide was employed instead of $^{99}$Tc-[D-Arg-Gly-D-Cys]-β-Ala. The amount of the unlabeled peptide varied between $10^{-6}$ M to $10^{-4}$ M. The data from this assay showed that the unlabeled peptide has substantially lower affinity, in the range of $IC_{50}>10^{-4}$ M, in competing with the $^{99m}$Tc-labeled peptide for the receptor site. FIG. 5 depicts the binding curve obtained in this experiment for unlabeled peptide, together with the binding curve for $^{99}$Tc-labeled peptide.

EXAMPLE 18

Competition of Sn-D-Arg-Gly-D-Cys-β-Ala With $^{99m}$Tc-[D-Arg-Gly-D-Cys]-β-Ala in Binding Assays This study was conducted as set forth in Example 16, with D-Arg-Gly-D-Cys-β-Ala incubated in a buffer containing stannous ions (the same buffer used for $^{99m}$Tc-labeling of the peptide). The amount of presumptively Sn-labeled peptide varied between $10^{-6}$ M to $10^{-4}$ M. The data showed that the Sn-labeled peptide has substantially lower affinity in competing with the $^{99m}$Tc-labeled peptide for the receptor site. The presence of stannous does not interfere with the affinity of the peptide for its platelet receptors.

EXAMPLE 19

Figure 6:
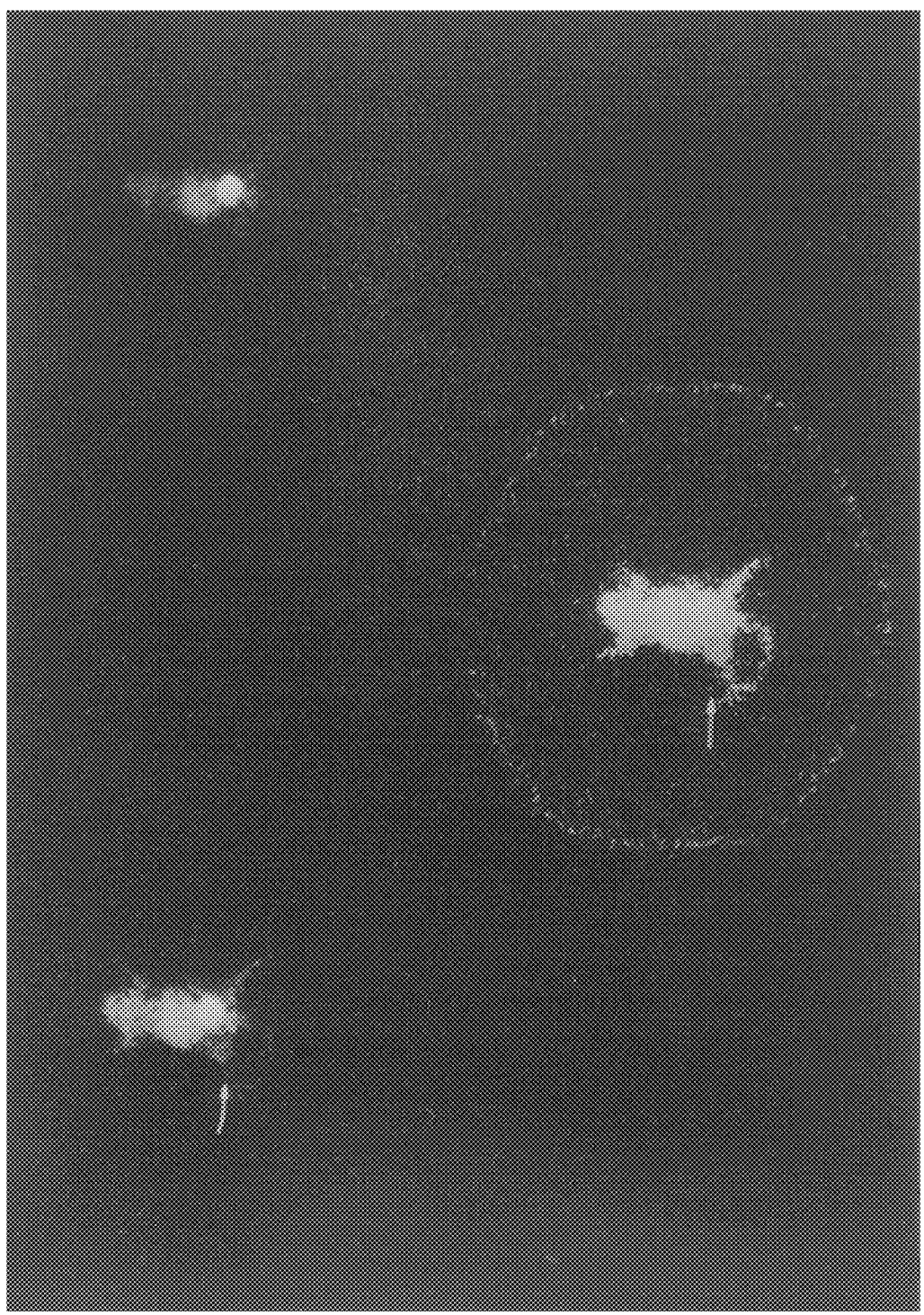
FIG. 6 shows a gamma camera image of an induced clot in a leg in an animal model using $^{99m}$Tc-labeled D-Arg-Gly-D-Cys-β-Ala.

Imaging of Clot in Leg Using $^{99m}$Tc-[D-Arg-Gly-D-Cys]-β-Ala 100 to 200 µL of a saline solution of thrombin (10–20 units) was injected intramuscularly in the upper thigh region of mice. This was done to induce formation of blood clots at the site of injection. 5–30 minutes after injection of thrombin, 50–200 µCi of $^{99m}$Tc-labeled D-Arg-Gly-D-Cys-β-Ala peptide prepared according to the method of Example 5 was injected in the animal through the tail vein. Gamma camera images were taken immediately thereafter by placing the animal on a parallel collimator attached to the camera. During the course of imaging the animal was subdued by intraperitoneal injections of ketamine. The site of clot inducement in the leg could be visualized as a result of the accumulation and localization of the $^{99m}$Tc-labeled peptide. Continual imaging was possible up to 45–60 minutes post-injection of the peptide or until the clot was cleared by the animal's body-defense mechanisms. FIG. 6 shows a gamma camera image of a mouse obtained at 25 minutes after injection of the $^{99m}$Tc-labeled peptide, which was 38 minutes after injection of 100 µL of thrombin injected into the leg of the animal.

EXAMPLE 20

Imaging of Lung Clot Using $^{99m}$Tc-[D-Arg-Gly-D-Cys]-β-Ala

Figure 7:
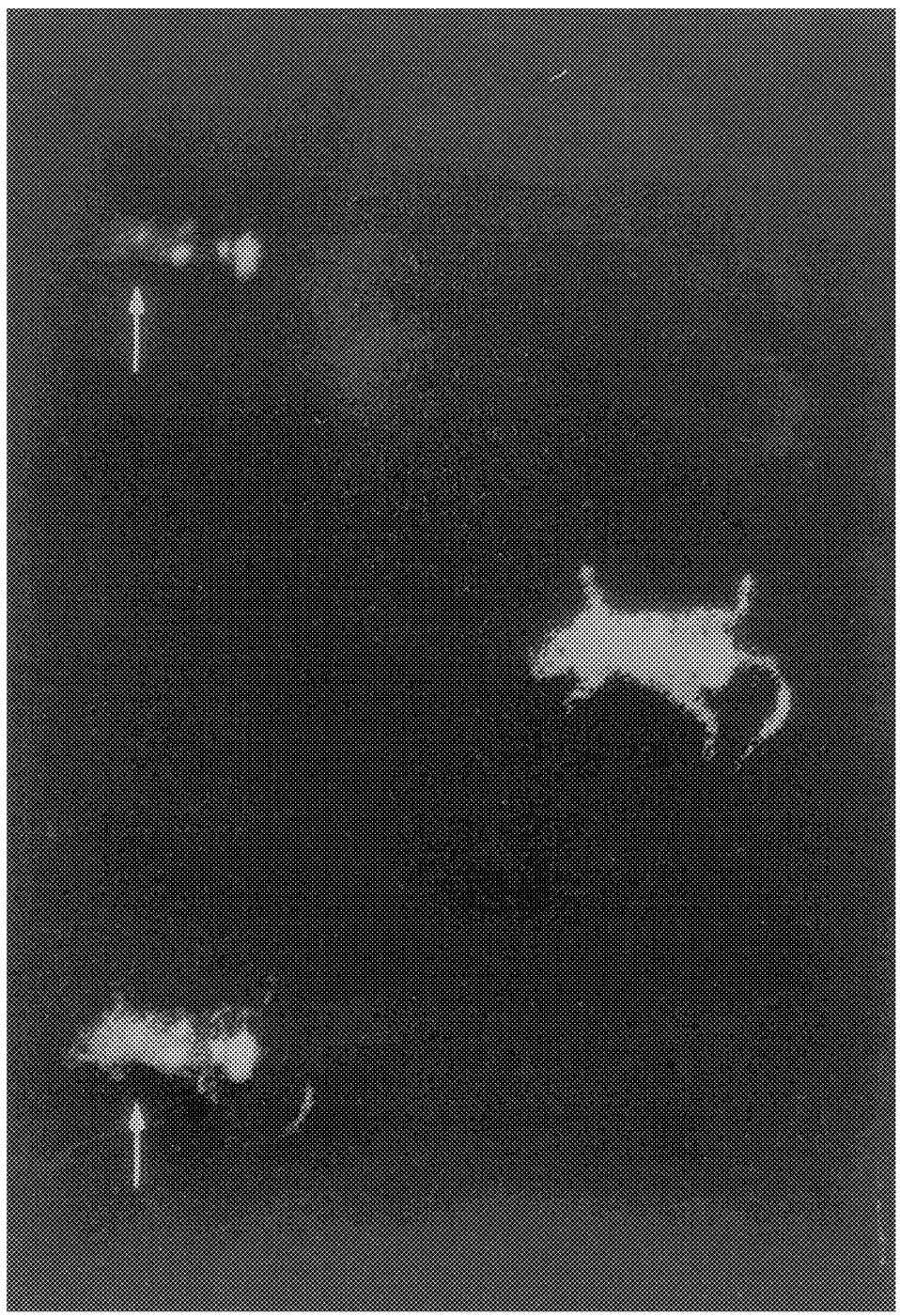
FIG. 7 shows a gamma camera image of an induced lung clot in an animal model using $^{99m}$Tc-labeled D-Arg-Gly-D-Cys-β-Ala.

300 µL of saline reconstituted thrombin (30 units) was incubated with about 100 million polyvinyl fluoridine beads (5 micron average size) for 1 hour. The beads were then recovered by centrifugation and re-suspended in 300 µL of fresh saline. 100 to 200 µL of this suspension, or 100–200 µL of the original saline solution of thrombin (10–20 units), was injected in a rat through its tail vein. This process causes blood clotting, with the clots getting trapped in the lung. These pulmonary emboli were then imaged with tail-vein injected $^{99m}$Tc-labeled D-Arg-Gly-D-Cys-β-Ala prepared by the method of Example 5, injected within 5–30 minutes of administration of thrombin. Gamma camera images were taken immediately thereafter by placing the animal on a parallel collimator attached to the gamma camera. During the course of imaging the animal was subdued by intraperitoneal injections of ketamine. The pulmonary emboli induced in this manner could be visualized as a result of the accumulation and localization of the $^{99m}$Tc-labeled peptide. Continual imaging was possible up to 45–60 minutes post injection of the peptide, or until the clot was cleared by the animal. FIG. 7 shows the gamma camera image of a pulmonary embolism obtained at 7 minutes after injection of the $^{99m}$Tc-labeled peptide, which was 34 minutes after injection of 200 µL of thrombin-coated beads.

EXAMPLE 21

Design and Synthesis of Tuftsin Analogue

A molecule based on the receptor binding characteristics of tuftsin was designed. Using an amino acid $N_3S_1$ metal ion-binding backbone, and modifying and decorating the backbone to arrive at a construct similar to the receptor binding region of tuftsin, the sequence Thr-D-Lys-Gly-D-Cys-Arg was designed so that the peptide would bind the tuftsin receptor on granulocytes after labeling with $^{99m}$Tc, or another suitable metal ion. The peptide was made by solid-phase peptide synthesis, using methods similar to the method of Example 1. In brief, Fmoc-Arg(Pmc) was coupled to 4-alkoxybenzyl alcohol resin, a peptide synthesis resin. After the removal of the Fmoc group by treatment with piperidine, the peptide chain was elongated successively using Fmoc-D-Cys(Trt), Fmoc-Gly, Fmoc-D-Lys(Boc), and Fmoc-Thr(Bu$^t$). Fmoc group from the resulting peptide-resin, Fmoc-Thr(Bu$^t$)-D-Lys(Boc)-Gly-D-Cys(Trt)-Arg(Pmc)-Resin, was removed in a similar fashion. Fully unprotected peptide was released from the resin by treatment with TFA. The peptide was purified by reversed phase HPLC and obtained as a lyophilized white powder. Fast atom mass spectrometric analysis gave correct mass for the synthesized peptide.

The peptide may also be synthesized by similar general methods of solid-phase peptide synthesis using Boc-chemistry, as well as solution-phase peptide synthesis methods analogous to those described in Examples 2 and 3.

EXAMPLE 22

Preparation of Thr-D-Lys-Gly-D-Cys-Arg Conjugated to Higher Molecular Weight Molecules The conjugation of high molecular weight carrier molecules, such as PEG, PVA, fatty acids and others, to the peptide Thr-D-Lys-Gly-D-Cys-Arg is achieved either after the synthesis of the peptide or during the synthesis of the peptide. The attachment of these carrier molecules to the peptide is by the method of Example 4, or carrier molecules are also attached to the peptide during its synthesis by solid-phase or solution-phase methods of peptide synthesis. The carrier molecules are attached either at the N-terminus or C-terminus, or at both termini.

EXAMPLE 23

Radiolabeling and Formulation of Radiopharmaceuticals Using Thr-D-Lys-Gly-D-Cys-Arg Direct Labeling Method A for the Peptide: The peptide Thr-D-Lys-Gly-D-Cys-Arg synthesized according to the method of Example 21 was labeled with $^{99m}$Tc in the presence of stannous as reducing agent that was pre-stabilized in a succinate-EDTA buffer. 100 µg of the peptide was mixed with generator eluted $^{99m}$Tc-sodium pertechnetate (1–35 mCi of radioactivity in up to 500 µL volume). To this was added a nitrogen purged solution (200–400 µL) of stannous-succinate-EDTA buffer (1 mM–20 mM–1.1 mM, pH 6.2). The head space of the vial was purged with nitrogen and the solution placed in a boiling water bath for 25 minutes. The solution after cooling was optionally diluted further with saline. A small aliquot of this $^{99m}$Tc labeled peptide was analyzed by reversed phase HPLC on a C-18 column (VYDAC, Cat. No. 218TP104). A gradient of 0–30% acetonitrile completed in 30 minutes at a flow rate of 1.5 mL/minute was employed. The radioelution profile was generated by a radio-detection flow cell system attached to the HPLC. The profile indicated that the $^{99m}$Tc-labeled peptide eluted as a major peak that split into a doublet of peaks at its apex (retention times of 12.9 and 13.1 minutes). These doublets seemed to represent two isomers of the labeled species due to an isomerism in the $^{99m}$TcO[V] core. A sample of the peptide labeled in a similar fashion, but not placed in the boiling water bath, exhibited additional peaks centered at 14.8 and 16.2 minutes, which might be due to multimeric species of the peptide-$^{99m}$Tc complex which on heating collapse to the major peak representing a 1:1 peptide-$^{99m}$Tc complex. The elution profile also indicated that the detectable amount of reduced $^{99m}$Tc (not complexed to the peptide) that elutes with the solvent peak (retention time 2.2 minutes), if any, was no more than 4%. A 10 µCi sample of the labeled preparation was spotted on an instant thin layer chromatography (ITLC) strip (1.5×10 cm silica gel impregnated strips, Gelman Science, Ann Arbor, Mich.) and developed with 150 mM NaCl. Radioactivity measurements on this strip revealed that the origin had only 2–4.5% of radioactivity, which corresponds to the amount of $^{99}$HTc colloid present in the preparation. The labeled preparation, when stored at room temperature for up to 36 hours, did not show any change in its HPLC and ITLC profiles. The HPLC and ITLC results together demonstrate a very good $^{99m}$Tc labeling profile for this peptide.

Method A Radiopharmaceutical Kit Formulation: The peptide Thr-D-Lys-Gly-D-Cys-Arg was formulated in a kit form to facilitate convenient $^{99m}$Tc labeling. To achieve this, 100 µg of the peptide taken in a 5 mL serum vial was mixed with 400 µL of nitrogen-purged stannous-succinate-EDTA buffer (1 mM–20 mM–1.1 mM EDTA, pH 6.2). The head space of the vial was immediately purged with nitrogen. The contents were then lyophilized, filled with argon or nitrogen and sealed. The lyophilized kits can be stored for longer periods of time at 4° C. For technetium labeling generator-eluted $^{99m}$Tc-sodium pertechnetate (1–35 mCi of radioactivity in up to 500 µL volume) was injected into the vial. The contents of the vial were thoroughly mixed, and the vial was vented with an injection needle and placed in a boiling water bath for 25 minutes. After cooling the contents can be diluted with saline or PBS. Examination of an aliquot by HPLC and ITLC techniques as described above gave results identical to those that were obtained under direct labeling of the peptide.

Alternate Method A Radiopharmaceutical Kit Formulation. The peptide Thr-D-Lys-Gly-D-Cys-Arg was also formulated in a kit form with each vial containing 5µg of the peptide and 400 µL of nitrogen-purged stannous-succinate-EDTA buffer (1 mM–20 mM–1.1 mM EDTA, pH 6.2). Kits with 5 µg of peptide were labeled with 2 mCi of $^{99m}$Tc and the equivalent of 50 mCi of $^{99m}$Tc as $^{99}$Tc, for a metal ion concentration equivalent to 52 mCi of $^{99m}$Tc, with no significant radiochemical impurities. The ratio of metal ion to peptide was 1:15.4 with 52 mCi equivalent of $^{99m}$Tc. By increasing the quantity of $^{99}$Tc, successful labeling was achieved at as low as a 1:8 metal ion-to-peptide ratio using 5 µg kits.

Direct Labeling Method before the Peptide: The peptide Thr-D-Lys-Gly-D-Cys-Arg, synthesized according to the method of Example 21, was labeled with $^{99m}$Tc in the presence of stannous as reducing agent that was pre-stabilized in sodium glucoheptonate. Between 1–10 µg of the peptide was mixed with generator-eluted $^{99m}$Tc-sodium pertechnetate (1–35 mCi of radioactivity in 0.5–3.5 mL volume). To this was added a nitrogen-purged solution (200–400 µl) of stannous-glucoheptonate buffer (1 mM–200 mM , pH 7.5–8.5). The head space of the vial was purged with nitrogen and the solution placed in a boiling water bath for 15 minutes. The solution after cooling was optionally diluted further with saline. A small aliquot of this $^{99m}$Tc labeled peptide was analyzed by reverse phase HPLC on a C-18 column as described in Example 23 and similar results obtained as described for Method A. In general, 92–95% of the radioactivity was found, by ITLC and SepPak techniques, to be peptide-bound, with 2–5% of radioactivity eluted as uncomplexed $^{99m}$Tc and 1–3% as $^{99m}$Tc-colloid. For SepPak analysis, a 10–100 µCi sample of the labeled preparation was applied to a SepPak Plus C-18 Cartridge which had been washed with EtOH (10 mL), and equilibrated with 10 mL of 0.001 N HCl (Eluant-A). The cartridge was successively eluted with 10 mL volumes of Eluant-A and Eluant-B (1:1 EtOH-Saline). In both instances, the cartridge eluate was measured for eluted radioactivity to give an estimation of (a) hydrophilic impurities such as free $^{99m}$Tc and (b) labeled peptide. The radioactivity left bound to the eluted cartridge yields an estimation of the non-elutable impurities such as $^{99m}$Tc colloid. The labeled preparation, when diluted with saline (up to 10 mL) or stored at room temperature for up to 36 hours, did not show any change in its HPLC, ITLC or SepPak elution profiles. The HPLC, ITLC, and SepPak results together suggest a very good $^{99m}$Tc labeling profile for this peptide.

Method B Radiopharmaceutical Kit Formulation: The peptide Thr-D-Lys-Gly-D-Cys-Arg was also formulated in a kit form to facilitate convenient $^{99m}$Tc labeling. Between 1 and 10 µg of the peptide taken in a 5 mL serum vial was mixed with 400 µL of nitrogen-purged stannous-glucoheptonate buffer (1 mM–200 mM, pH 7.5–8.5) and lyophilized as described in Example 23. The one-step lyophilized labeling kits obtained in this manner were labeled by addition of sodium pertechnetate $^{99m}$Tc as described in Example 23, and tested by HPLC, ITLC and SepPak quality control procedures. The results obtained were substantially identical to those obtained for Method B described above.

Direct Labeling Method C for the Peptide: The peptide Thr-D-Lys-Gly-D-Cys-Arg, synthesized according to the method of Example 21, was labeled with $^{99m}$Tc in the presence of stannous as reducing agent that was stabilized in tartrate-phalate buffer, as described in Example 5.

EXAMPLE 24

Alternate Radiolabeling of Thr-DLys-Gly-D-Cys-Arg

The peptide of Example 21 was also labeled by the direct labeling approach described in Example 23 using alternate buffers for stabilization of the stannous ions. The following alternate buffers were employed: (a) stannous-tartrate-phthalate (1 mM-10 mM–40 mM, pH 6.2), (b) stannous-tartrate-phthalate-glycylglycine (1 mM–10 mM–40 mM–50 mM , pH 6.6), and (c) stannous-tartrate-succinate (1 mM–10 mM–20 mM, pH 6.2). Labeling both at room temperature or

Figure 8:
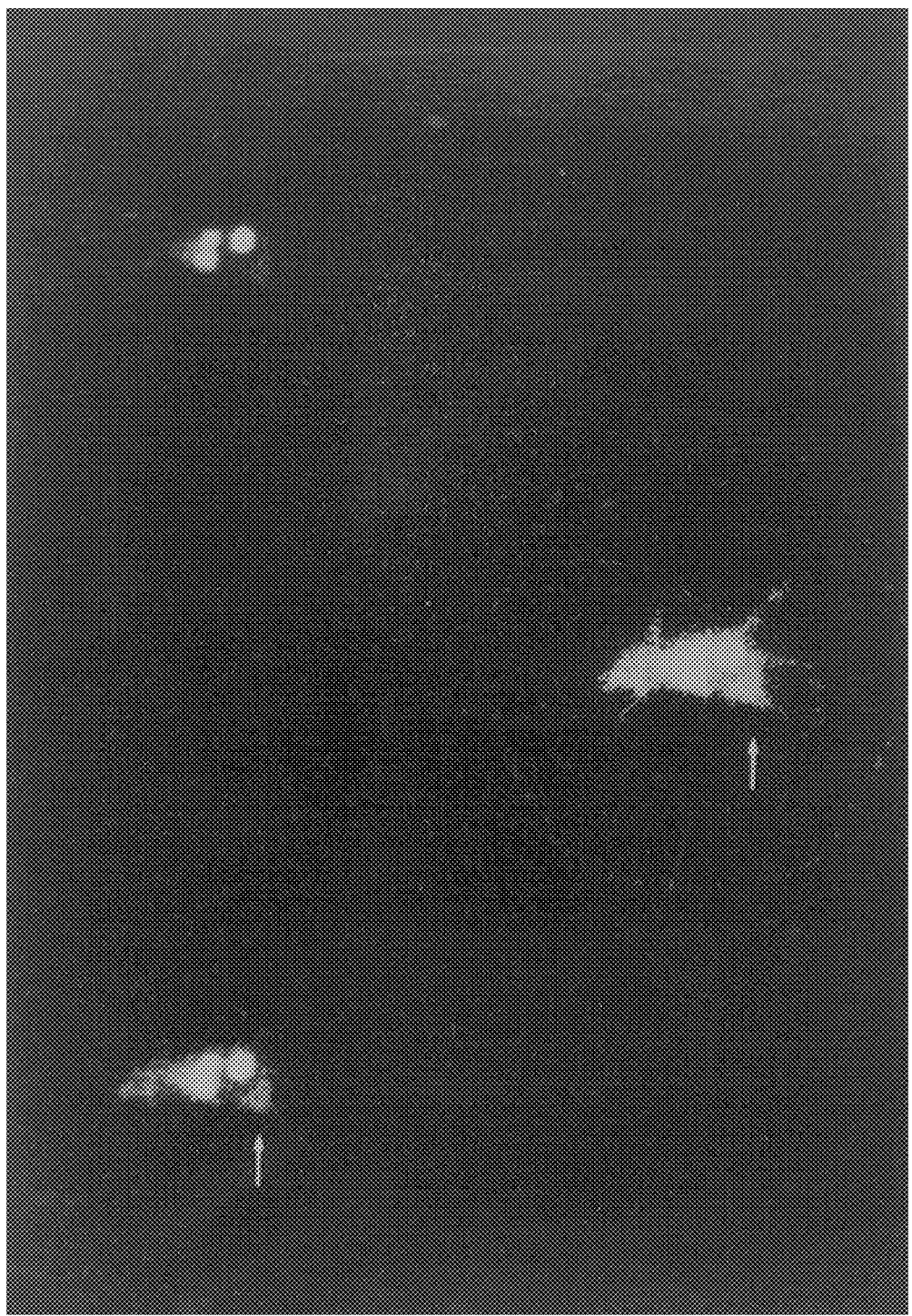
FIG. 8 shows gamma camera images of mice with sour milk induced abscesses in the leg, with the image taken 20 minutes after injection of $^{99m}$Tc-Thr-D-Lys-Gly-D-Cys-Arg.
Figure 9:
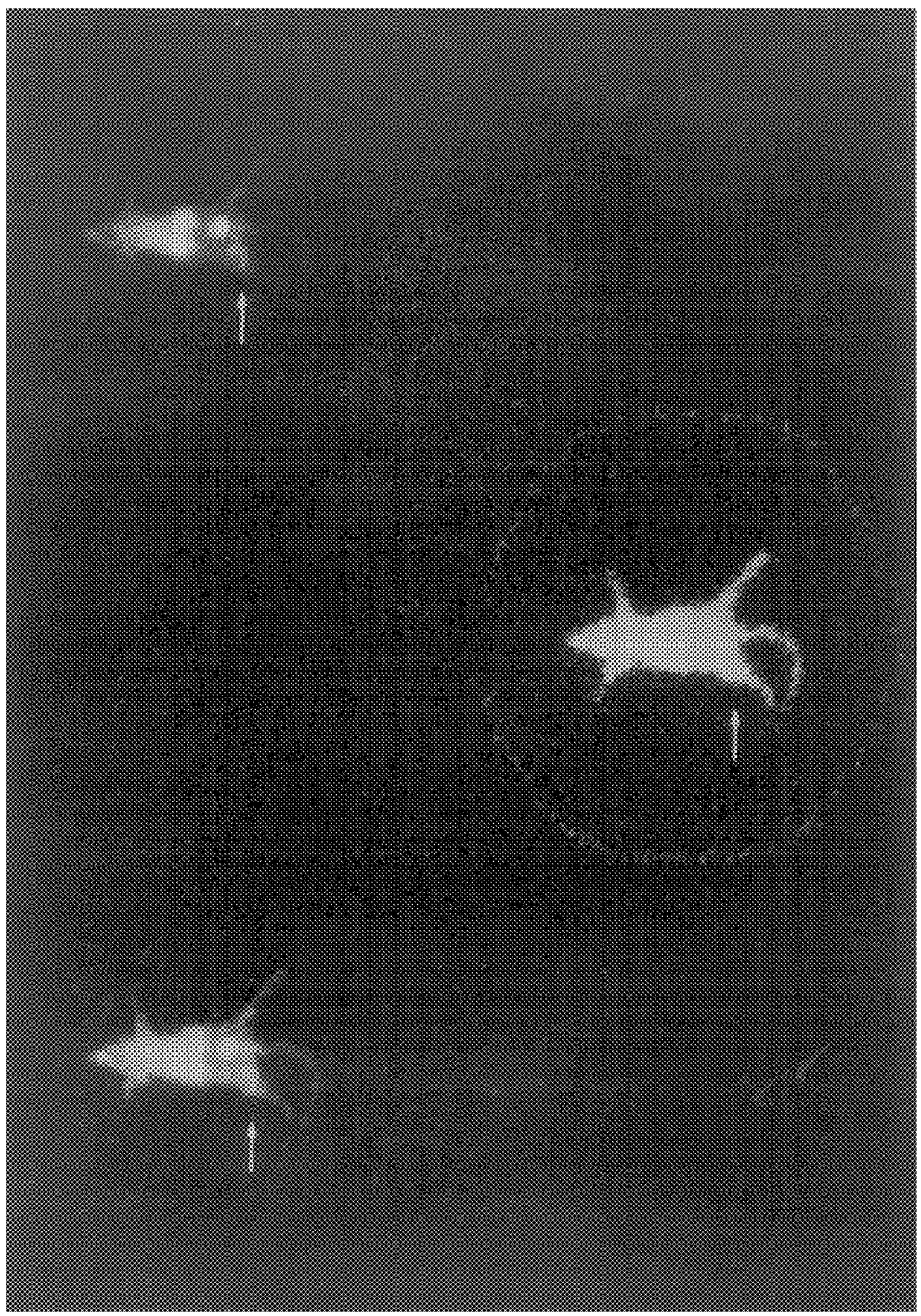
FIG. 9 shows gamma camera images of mice with sour milk induced abscesses in the leg, with the image taken 4 hours after injection of $^{99m}$Tc-Thr-D-Lys-Gly-D-Cys-Arg.

EXAMPLE 25
Imaging Sour Milk Induced Abscess Using $^{99m}$Tc-Thr-[D-Lys-Gly-D-Cys]-Arg 100–200 μL of sour milk (a milk sample allowed to stand at room temperature for 14 hours) was injected in the upper thigh region of a rat or mouse to cause an abscess. 30–60 minutes after injection of the sour milk, a $^{99m}$Tc-labeled Thr-D-Lys-Gly-D-Cys-Arg preparation (50–200 μCi) of Example 23 was injected through the animal's tail vein. Gamma camera images were taken immediately thereafter by placing the animal on a parallel collimator attached to the camera. During the course of imaging, the animal was subdued by intraperitoneal injections of ketamine. The site of abscess was visualized as a result of the accumulation and localization of the $^{99m}$Tc-labeled peptide. Continual imaging was possible for more than 7 hours post injection of the peptide. FIGS. 8 and 9 show gamma camera images of mice with sour milk induced abscesses in the leg. The $^{99m}$Tc-labeled peptide was injected 55 minutes after injection of the sour milk. The image in FIG. 8 was taken 20 minutes after injection of the $^{99m}$Tc-labeled peptide, and the image in FIG. 9 was taken 4 hours after injection of the $^{99m}$Tc-labeled peptide.

EXAMPLE 26
Imaging Ketamine Induced Abscess Using $^{99m}$Tc-Thr-[D-Lys-Gly-D-Cys]-Arg 100 μL of a saline solution of ketamine (100 mg/mL) was injected in the upper thigh region of a rat or mouse to cause an inflammation. After 30–60 minutes, a $^{99m}$Tc-labeled Thr-D-Lys-Gly-D-Cys-Arg preparation (50–200 μCi) of Example 23 was injected through the animal's tail vein. Gamma camera images were taken immediately thereafter as described in Example 25. The site of inflammation was visualized as a result of the accumulation and localization of the $^{99m}$Tc-labeled peptide. Continual imaging was possible for more than 2 hours post injection of the peptide.

EXAMPLE 27
Plasma Stability of $^{99m}$Tc-LABELED Constructs 10 to 100 μL of a variety of $^{99m}$Tc-labeled peptide constructs of this invention, labeled with up to 2 mCi of $^{99m}$Tc and prepared generally as described in Examples 5 and 23, were mixed with an equal volume of human platelet poor plasma (PPP). The resulting mixture was then incubated for one hour at 37° C. An aliquot of both this mixture and the $^{99m}$Tc-labeled peptide construct not incubated with PPP was then analyzed by reversed-phase HPLC under the general conditions described in Examples 5 and 23. A comparison of the generated radioelution profile of the PPP and $^{99m}$Tc-labeled peptide construct mixtures with that of samples not incubated with PPP revealed no substantive difference in the two HPLC profiles. No peaks, other than those of the $^{99m}$Tc-peptide construct not incubated with PPP, were detected in any profiles, suggesting complete or near complete stability of the $^{99m}$Tc-labeled peptide constructs in the presence of serum proteases contained in PPP. The following $^{99m}$Tc-labeled peptide constructs were assayed for stability in human serum:

$^{99m}$Tc-[D-Arg-Gly-D-Cys]-β-Ala $^{99m}$Tc-[Arg-Gly-D-Cys]-β-Ala, $^{99m}$Tc-[Gly-D-Arg-D-Cys]-β-Ala

Thr-$^{99m}$Tc-[D-Lys-Gly-D-Cys]-Arg.

Figure 10:
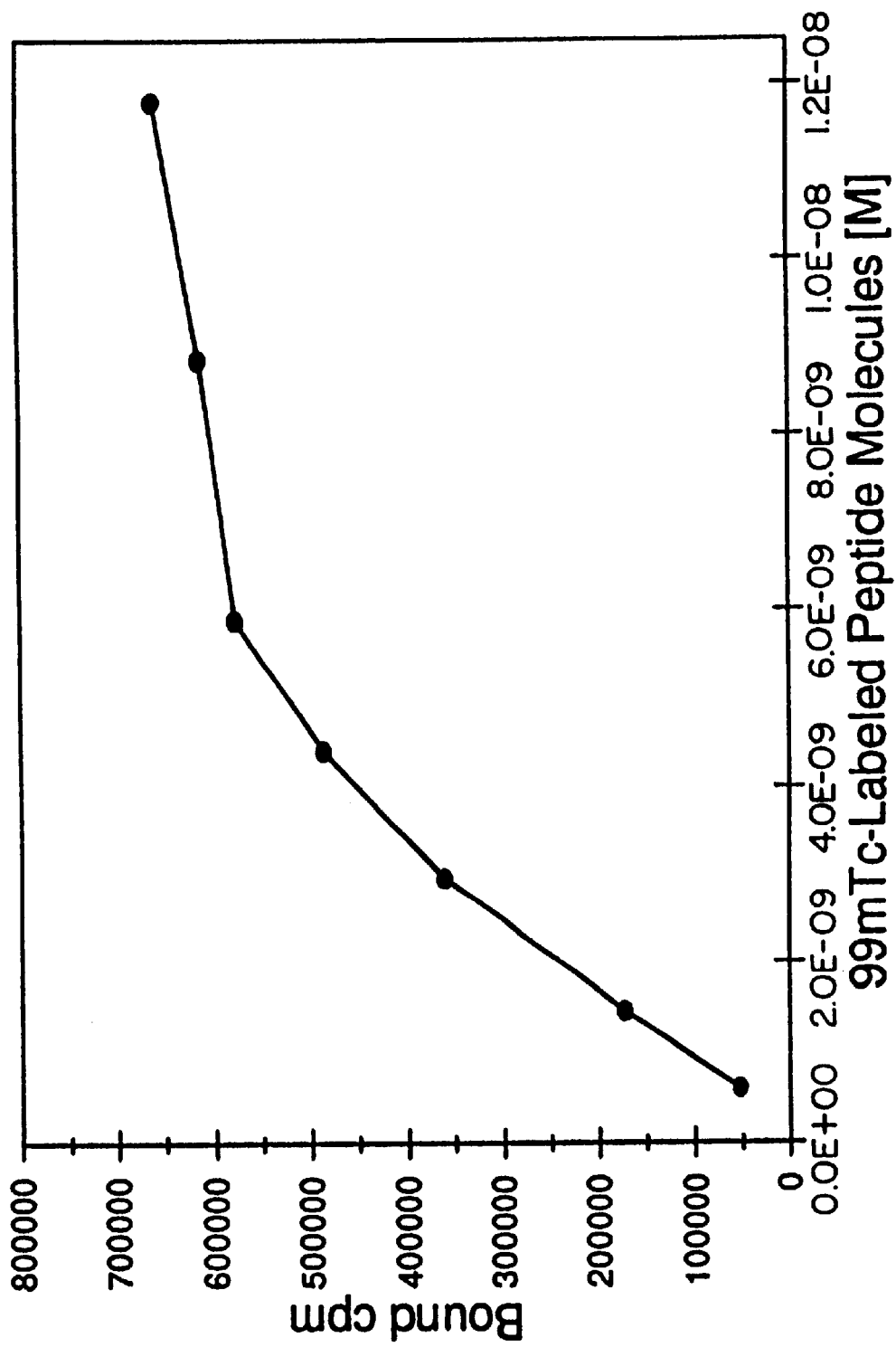
FIG. 10 shows a saturation binding isotherm of binding of $^{99m}$Tc-labeled Thr-D-Lys-Gly-D-Cys-Arg with human polymorphonuclear leukocytes.

EXAMPLE 28
Saturation Binding of Human Polymorphonuclear Cells Using 99$^{99m}$Tc-Thr-[D-Lys-Gly-D-Cys]-Arg Saturation binding of 99$^{99m}$Tc-labeled Thr-D-Lys-Gly-D-Cys-Arg peptide, prepared by the method of Example 23, to human PMN leukocytes was demonstrated using both freshly collected PMN leukocytes from human blood as well as formalin-fixed PMN leukocytes. The concentration of PMN cells in the PBS as incubation medium was $2.5 \times 10^6$ cells/mL per one assay tube. Increasing amounts of $^{99m}$Tc-labeled peptide were added to constant amounts of cells taken in different assay tubes. Similar volumes of PBS were used at each concentration of the $^{99m}$Tc-labeled peptide as a measure of the non-specific binding component under the experimental conditions. The binding was allowed to take place for 30 minutes after which the tubes were transferred to an ice bath. A 200 μL aliquot corresponding to $0.5 \times 10^6$ cells was filtered through a glass fiber filter that was pre-soaked in 50% calf serum in PBS for 30 minutes. The filters were then washed three times with 1 mL of PBS and counted in a gamma counter for the bound radioactivity. The data was normalized to account for the decay of $^{99m}$Tc and plotted. The results reveal the saturation binding kinetics of the peptide for its receptor on PMN cells. An analysis of the data gave an value for $K_D$ in the range of 1–5 nM. FIG. 10 shows the binding curve obtained in this experiment.

EXAMPLE 29
Saturation Binding of HL-60 Cells Using $^{99m}$Tc-Thr-[D-Lys-Gly-D-Cys]-Arg Saturation binding of $^{99m}$Tc-labeled Thr-D-Lys-Gly-D-Cys-Arg peptide, prepared by the method of Example 23, to HL-60 cells (a human leukemic cell line) was demonstrated using both freshly cultured HL-60 cells as well as formalin-fixed HL-60 cells. The assay was performed as described for PMN leukocytes in Example 28. An analysis of the data gave a value for $K_D$ in the range of 1–5 nM.

Figure 11:
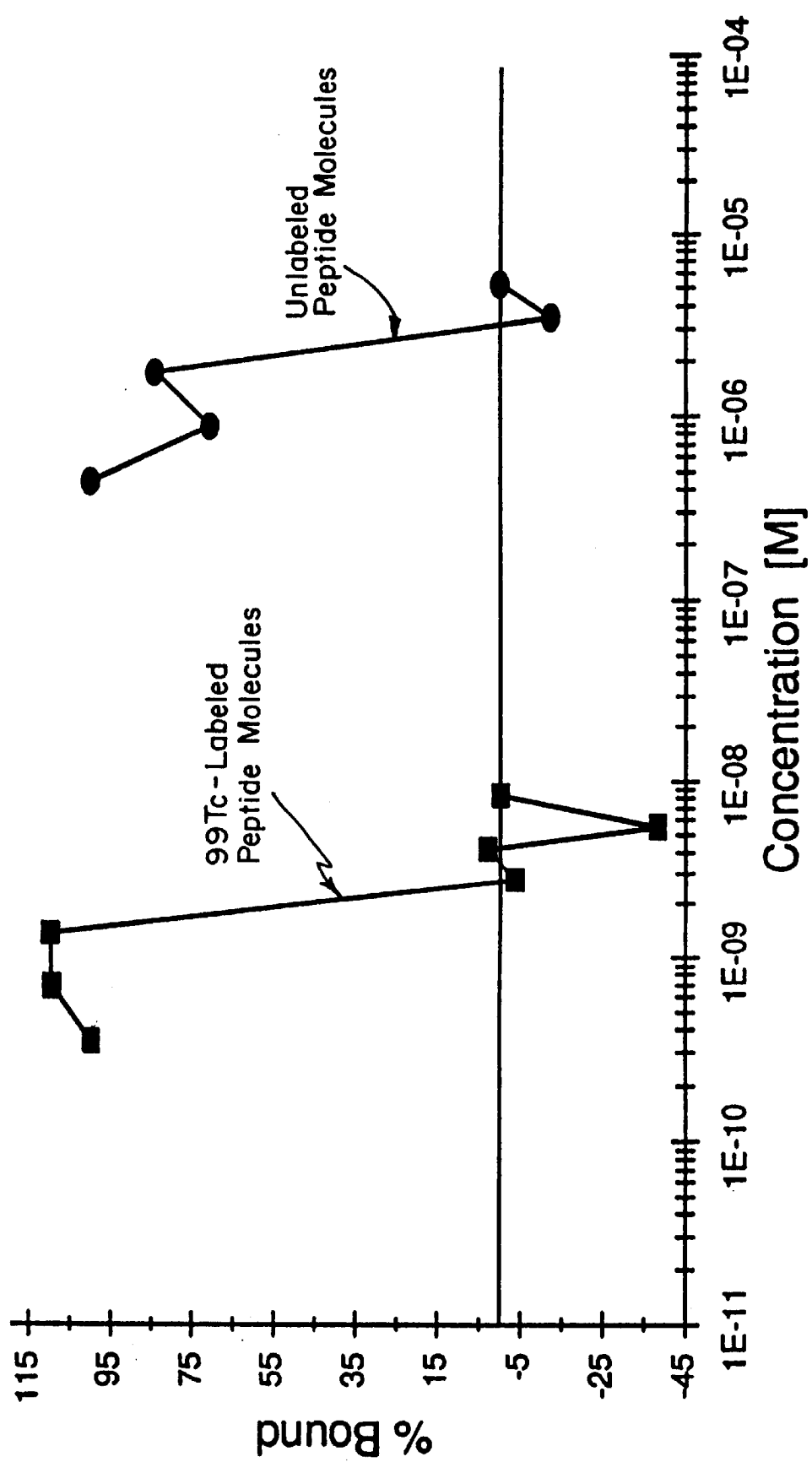
FIG. 11 shows results of competition binding of $^{99}$Tc-labeled Thr-D-Lys-Gly-D-Cys-Arg and unlabeled Thr-D-Lys-Gly-D-Cys-Arg with $^{99m}$Tc-labeled Thr-D-Lys-Gly-D-Cys-Arg for binding to human polymorphonuclear leukocytes.

EXAMPLE 30
Competition Binding to Human Polymorphonuclear Cells Using $^{99m}$Tc-Thr-[D-Lys-Gly-D-Cys]-Arg and $^{99}$Tc-Thr-[D-Lys-Gly-D-Cys]-Arg Formalin-fixed PMN leukocytes ($2.5 \times 10^6$ cells in a final volume of one mL per assay tube), as generally discussed in Example 28, were incubated with a mixture of $^{99m}$Tc-labeled Thr-D-Lys-Gly-D-Cys-Arg and $^{99}$Tc-labeled Thr-D-Lys-Gly-D-Cys-Arg peptide. A constant but trace amount of the $^{99m}$Tc labeled peptide was used in this assay. The amount of $^{99}$Tc-labeled peptide, however, varied between $10^{-9}$ M to $10^{-7}$ M in terms of the $^{99}$Tc labeled fraction of the peptide molecules. For this experiment, both the $^{99m}$Tc-labeled as well as the $^{99m}$Tc-labeled peptides were prepared according to the methods of Example 24, with the assay performed as described in Example 28. The data from this assay showed that the IC$_{50}$ m value for the $^{99m}$Tc-labeled peptide was in the range of 1–5 nM, while the native peptide without a metal ion had an IC$_{50}$ in the range of 2–5 mM. This value was similar to the ones obtained in the various saturation binding experiments described in Examples 28 and 29. FIG. 11 shows the binding curves obtained in this experiment for $^{99}$Tc-labeled peptide.

EXAMPLE 31
Competition Binding to Human Polymorphonuclear Cells Using $^{99m}$Tc-Thr-[D-Lys-Gly-D Cys]-Arg And Unlabeled Thr-D-Lys-Gly-D-Cys-Arg This experiment was conducted using the methods of Example 30, except that unlabeled Thr-D-Lys-Gly-D-Cys-Arg peptide, in concentrations from $10^{-10}$ M to $10^{-4}$ M, was used. The unlabeled peptide did not effectively compete with the $^{99m}$Tc-labeled peptide. The calculated $IC_{50}$ value for unlabeled peptide was over $10^{-5}$ M, substantially higher than the $IC_{50}$ value for the $^{99m}$Tc-labeled peptide. This results indicates that the $^{99m}$Tc and $^{99}$Tc-labeled peptide molecules are biologically active, while the unlabeled peptide has marginal biological activity. FIG. 11 shows the binding curves obtained in this experiment for unlabeled peptide, together with the binding curve for 99Tc-labeled peptide.

EXAMPLE 32
Competition Binding to Human Polymorphonuclear Cells of $^{99m}$Tc-Thr-[D-Lys-Gly-D-Cys]-Arg Using Natural Tuftsin Formalin fixed PMN leukocytes ($2.5 \times 10^6$ cells in a final volume of one mL per assay tube), as described in Example 28, were incubated with a mixture of $^{99m}$Tc-labeled Thr-D-Lys-Gly-D-Cys-Arg and natural tuftsin Thr-Lys-Pro-Arg peptide. A constant trace amount of the $^{99m}$Tc-labeled peptide was prepared as described in Example 28. The amount of the unlabeled peptide, however, varied between $10^{-10}$ M to $10^{-5}$ M. The assay was performed as described in Example 28. The results yielded an $IC_{50}$ for natural tuftsin in the range of 100 nM, which is consistent with the results obtained by earlier investigators. The results also demonstrated that $^{99m}$Tc-Tbr-[D-Lys-Gly-D-Cys]-Arg binds the same receptor as the naturally occurring tuftsin molecule.

EXAMPLE 33
Competition Binding to HL-60 Cells Using $^{99m}$Tc-Thr-[D-Lys-Gly-D-Cys]-Arg and $^{99}$Tc-Thr-[D-Lys-Gly-D-Cys]-Arg Competition binding of $^{99m}$Tc-labeled Thr-D-Lys-Gly-D-Cys-Arg and $^{99}$Tc-labeled Thr-D-Lys-Gly-D-Cys-Arg for the tuftsin receptor on HL-60 cells was also performed according to the method of Example 28, using HL-60 cells as described in Example 29. The $IC_{50}$ value of 1–5 nM for $^{99}$Tc-labeled Thr-D-Lys-Gly-D-Cys-Arg obtained was similar to that obtained for the corresponding $^{99m}$Tc-labeled peptide in the saturation binding experiment of Example 29.

EXAMPLE 34
Competition Binding to HL-60 Cells Using $^{99m}$Tc- Thr-[D-Lys-Gly-D-Cys]-Arg and Unlabeled Thr-D-Lys-Gly-D-Cys-Arg Competition binding of $^{99m}$Tc-labeled Thr-D-Lys-Gly-D-Cys-Arg and Thr-D-Lys-Gly-D-Cys-Arg peptide for the tuftsin receptor on HL-60 cells was performed according to the method of Example 31. An $IC_{50}$ value of $>10^{-5}$ M for Thr-D-Lys-Gly-D-Cys-Arg peptide was obtained, confirming that the corresponding $^{99m}$Tc- or $^{99}$Tc-labeled species was the biologically active species.

EXAMPLE 35
Competition Binding to HL-60 Cells of $^{99m}$Tc-Thr-[D-Lys-Gly-D-Cys]-Arg Using Natural Tuftsin Competition binding of $^{99m}$Tc-labeled Thr-D-Lys-Gly-D-Cys-Arg and naturally occurring tuftsin Thr-Lys-Pro-Arg peptide for the tuftsin receptor on HL-60 cells was also performed according to the method of Example 32. A similar $IC_{50}$ value of 100 nM for natural Thr-Lys-Pro-Arg peptide was obtained from this experiment, as was the observation that the $^{99m}$Tc-labeled Thr-D-Lys-Gly-D-Cys-Arg binds to the same receptor as natural tuftsin, but the $99^{99m}$Tc-labeled peptide has higher affinity for its receptor than does the natural peptide.

Figure 12:
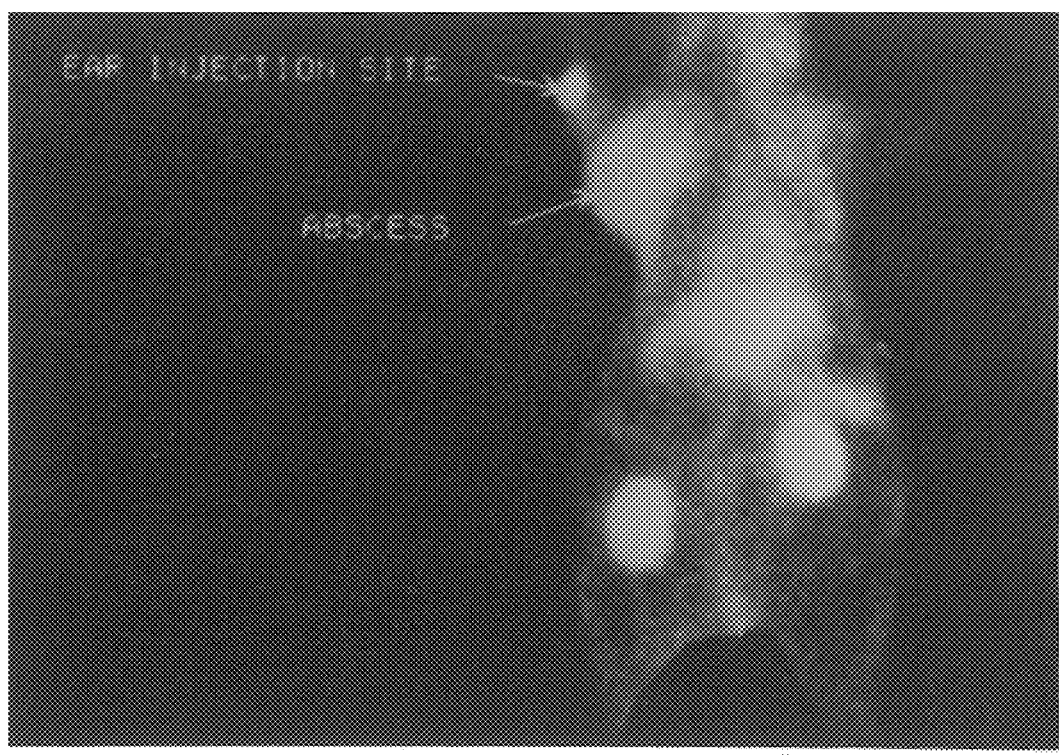
FIG. 12 shows gamma camera images of a turpentine-induced abscess in a rabbit, with the image taken 15 minutes after injection of $^{99m}$Tc-Thr-D-Lys-Gly-D-Cys-Arg.

EXAMPLE 36
Imaging Rabbit with Turpentine-Induced Sterile Abscess Using $^{99m}$Tc-Thr-[D-Lys-Gly-D-Cys]-Arg Turpentine was injected into the left hind thigh of a rabbit, according to a previously described animal model (Tsan MF: Studies of gallium accumulation in inflammatory lesions: III. Role of polymorphonuclear leukocytes and bacteria. *J Nucl Med* 19:492–495, 1978). Four days later an injection of 0.5 mCi $^{99m}$Tc-Thr-[D-Lys-Gly-D-Cys]-Arg, prepared according to the method of Example 23, was administered to the rabbit through its ear vein. Scintigraphic images were obtained that visualized the abscess site within 10 minutes post-injection of the peptide. FIG. 12 shows the results obtained at 15 minutes post injection. The abscess could be visualized for the course of the study period, four hours post injection.

EXAMPLE 37
Imaging Rabbit with Whiffle Ball-Induced Inflammation Using $^{99m}$Tc-Thr-[D-Lys-Gly-D-Cys]-Arg A whiffle ball was implanted subcutaneously in the left hind thigh of a rabbit using a reported model (Tsan MF, supra). Seven days later, an injection of casein was made into the whiffle ball to cause a localized inflammation, which was followed by an injection of 0.5 mCi $^{99m}$Tc-Thr-[D-Lys-Gly-D-Cys]-Arg, prepared by the method of Example 23, and administered to the rabbit through its ear vein. Scintigraphic images were obtained that visualized the inflammation site within the whiffle ball 10 minutes post-injection, and the images persisted for the course of the study period, four hours post-injection.

EXAMPLE 38
Imaging HL-60 Tumors in Mouse Model Using $^{99m}$Tc-Thr-[D-Lys-Gly-D-Cys]-Arg 500,000 HL-60 cells were mixed with 100 μL of a solution of Matrigel®, a basement membrane maxtrix product distributed by Becton Dickinson Labware (Bedford, Mass.), in saline (0.1% in saline). This was injected subcutaneously in the left hind thigh of a nude mouse, forming a visible and palpable tumor xenograft within 10 to 20 days. Between 20 and 40 μCi of $^{99m}$Tc-Thr-[D-Lys-Gly-D-Cys]-Arg prepared according to Example 23 was injected through the tail vein of the mouse. Whole body scintigraphic images of the mouse were taken starting 10 minutes post-injection. The localization of the peptide to the xenograft was visualized within 10 minutes and was observed throughout the experimentation period of six hours.

EXAMPLE 39
Imaging Tumors Using $^{99m}$Tc-Thr-[D-Lys-Gly-D-Cys]-Arg

Patients with tumors of various types, including small cell lung cancer, mammary cancer, prostate cancer, and melanoma, are injected with 5–20 mCi of $^{99m}$Tc-Thr-[D-Lys-Gly-D-Cys]-Arg prepared according to Example 23 or 24, with the total amount of peptide being between about 1 and 10 μg. Periodic whole body scintigraphic images are obtained starting 10 minutes post-injection to observe the localization of the radiolabeled peptide to the sites of cancer. The effectiveness of the labeled peptide to image these tumors is noted.

EXAMPLE 40
Imaging Abscesses and Inflammation Using $^{99m}$Tc-Thr-[D-Lys-Gly-D-Cys]-Arg Patients with suspected sites of abscess or inflammation are injected with 5–20 mCi of $^{99m}$Tc-Thr-[D-Lys-Gly-D-Cys]-Arg prepared according to Example 23 or 24, with the total amount of peptide being between about 1 and 10 µg. Periodic whole body scintigraphic images are obtained starting 10 minutes post-injection to observe the localization of the radiolabeled peptide to the sites of abscess or inflammation. The effectiveness of the labeled peptide to image these sites is noted.

EXAMPLE 41
Stable Rhenium Complexed Peptide: Synthesis and Stability of Thr-ReO[V]-[D-Lys-Gly-D-Cys]-Arg as a Potent Phagocyte Stimulatory Compound The peptide Thr-D-Lys-Gly-D-Cys-Arg was designed as a peptide that would bind the tuftsin receptor on granulocytes after complexation with ReO[V], and was synthesized as described in Example 21. 91 mg of this peptide as its trifluroacetate salt was taken in methanol (15 mL) and 85 mg of oxotrichlorobis(triphenylphosphine) rhenium[V] was added (Johnson N P et al: *Inorganic Chemistry*, 9:145–148, 1967). After addition of methanolic sodium acetate (1 mL), the reaction mixture was refluxed until the color of the reaction was changed from greenish yellow to dark violet or dirty brown. About 15 to 25 minutes of refluxing was sufficient. The methanol was then evaporated off, the residual solid dissolved in water, filtered and the filtrate lyophilized to yield a crude rhenium complex of the peptide. The crude rhenium complexed peptide was purified by semi-preparative RP-HPLC as generally described in Example 23. The HPLC profile of the product was similar to that described for corresponding $^{99m}$Tc-labeled peptide in the sense that the Re-labeled peptide exhibited two similar peaks, with retention times of 13.8 and 14.3 minutes, representing two isomers (syn and anti) arising due to isomerism in ReO[V] core. The Re-labeled peptide also exhibited UV absorption at λ 320–360 nm, characteristic of a ReO[V] coordinated species. The purified product was obtained as a light pinkish solid after lyophilization from aqueous solution. Electron spray mass spectrometry (ES-MS) gave the correct results for the mass of rhenium complexed peptide. The mass calculated was 761 and 763 (due to two natural isotopes of Re), and the mass found (M+1) was 762.3 and 764.3. Complexation of the metal ion to the peptide can also be readily confirmed by circular dichroism studies. The purified product was found to be stable, as determined by RP-HPLC, when stored at −20° C. for a five month study period. Aqueous solutions of the purified product stored at 2–5° C. were also found to be stable over the same time period.

Figure 13:
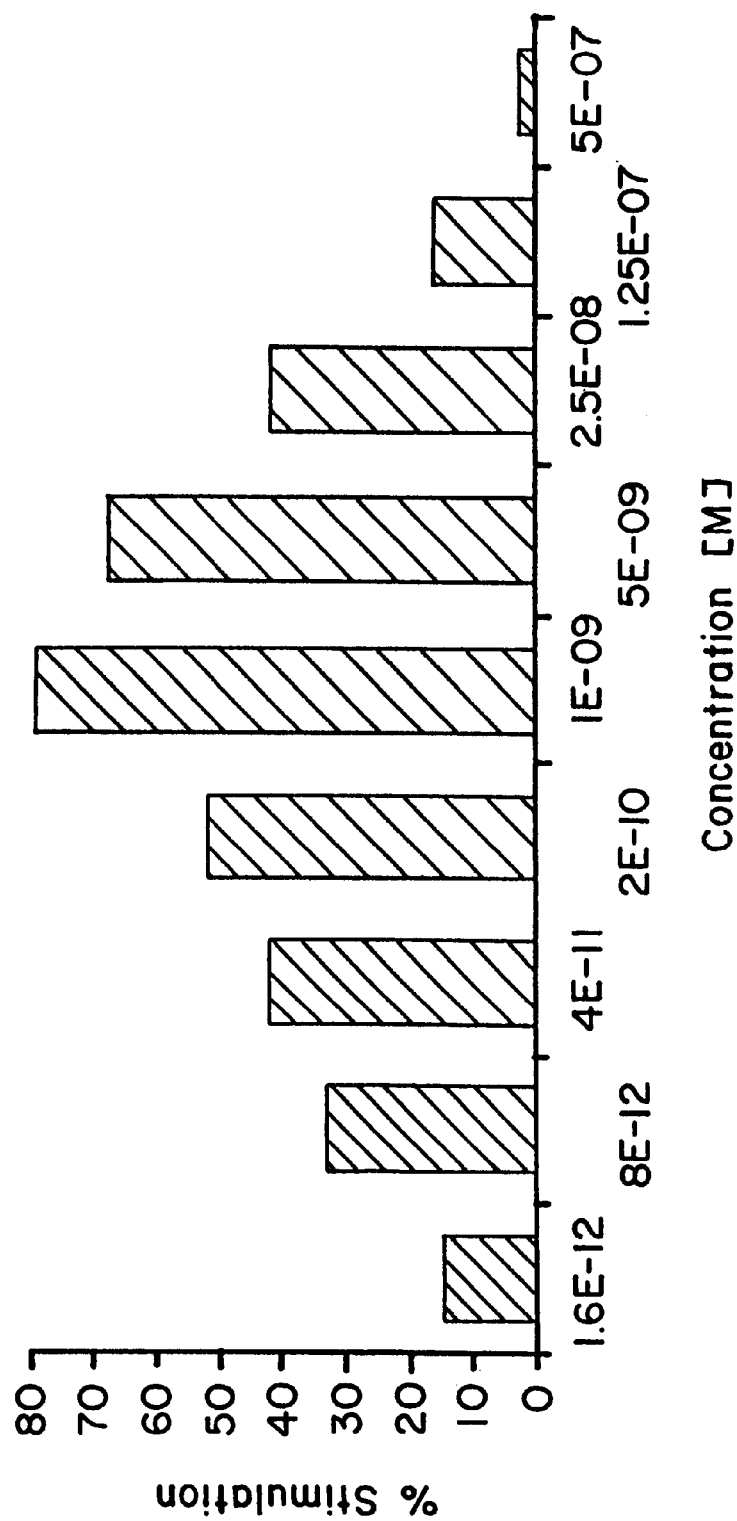
FIG. 13 shows a histogram of the dose-response relationship of the percent of stimulation of phagocytosis of heat inactivated yeast cells by human polymorphonuclear granulocytes upon exposure to ReO[V]-Thr-[D-Lys-Gly-D-Cys]-Arg.

EXAMPLE 42
Stimulation of Phagocytosis by Thr-ReO[V]-[D-Lys-Gly-D-Cys]-Arg a Potent Mimic of Natural Tuftsin An assay was performed using freshly harvested polymorphonuclear (PMN) granulocytes. Human blood from a donor (50–100 mL) was mixed with the anticoagulant ACD. The blood was processed to obtain buffy coat which was centrifuged through a lymphocyte separation medium (histopaque, from Sigma Chemical Co., St. Louis, Mo.). The contaminating erythrocytes were lysed by hypotonic treatment. The cells were washed with medium, differentially counted and were found to be approximately 96% PMNs with >95% viability. 400 µL of the cell suspension (1×10$^6$ cells) was incubated in a 3 mL polystyrene tube with 5 µL of a concentration of Thr-ReO[V]-[D-Lys-Gly-D-Cys]-Arg, prepared as in Example 41, (to yield final incubation concentration in the range $1\times10^{-12}$ to $1\times10^{-7}$ M) for 15 minutes at 37° C. A 100 µL suspension of heat inactivated yeast cells (5×10$^6$ cells) was then added. The final volume, 0.5 mL, of cell suspension with heat inactivated yeast cells was then incubated for 15 minutes at 37° C. Assays were performed in triplicates with multiple concentrations of Thr-ReO[V]-[D-Lys-Gly-D-Cys]-Arg, with a PBS blank as control for measuring the basal level of PMN stimulation. The assay tubes were then moved to storage at 4° C. to stop the reaction and smears were prepared, stained and counted for number of yeast cells ingested by 400 PMNs by count. The percentage phagocytosis stimulation was calculated according to the formula: [(Number of yeast cells ingested by metallopeptide stimulated cells—Number of yeast cells ingested by control cells)/(Number of yeast cells ingested by metallopeptide stimulated cells)]×100. The data is presented in FIG. 13 and shows a bell-shaped dose response curve for the metallopeptide with maximal stimulation seen at about 1 nM concentration.

EXAMPLE 43
Nitroblue Tetrazolium Dye Reduction Assay for Measurement of Stimulation of Hexose Monophosphate Shunt Activity by Thr-ReO[V]-[D-Lys-GlyD-Cys]-Arg, a Potent Mimic of Natural Tuftsin An assay was performed using freshly harvested polymorphonuclear (PMN) granulocytes as described in Example 42. The cells and all the reagent solutions were brought to 37° C. before the start of assay. 595 µL of the cell suspension (10×10$^6$ cells) was incubated in a 10 mL borosilicate glass tube and mixed with 400 µL of nitroblue tetrazolium solution (0.1% in PBS) and 5 µl of a concentration of Thr-ReO[V]-[D-Lys-Gly-D-Cys]-Arg, prepared as in Example 41, (to yield a final incubation concentration in the range $1\times10^{-12}$ to $1\times10^{-7}$ M) and incubated for 30 minutes at 37° C. The solution was centrifuged and the cells washed once with PBS. The cell pellet was extracted with dioxane (1 mL) by gentle sonication (10–15 minutes) to dissolve formazan that was produced inside the cells. The clear solution obtained after centrifugation was read spectrophotometrically at λ 540 nm. The assay was run in triplicates with several concentrations of Thr-ReO[V]-[D-Lys-Gly-D-Cys]-Arg and using a PBS blank as control for measuring basal level of PMN activity. The results indicated that maximum stimulation is obtained with 1–5 nM concentration of the metallopeptide. Natural tuftsin showed maximal stimulation at 100 nM concentration. The dose response curve in both cases was a bell shaped curve where increasing concentrations beyond maximum stimulation produced decreased biological response.

EXAMPLE 44
In Vivo Stability of $^{99m}$-Tc-Labeled Constructs

A group of six mice was injected intravenously, through the tail vein, or subcutaneously with between 50–100 µCi of $^{99m}$Tc-complexed peptides of this invention. Urine samples from the animals were collected at various time intervals between 30 and 120 minutes. The urine samples were centrifuged to sediment insoluble particulates and the supernatant analyzed by reversed-phase high-performance liquid chromatography using an online radiotracer detector. The radioelution profiles of all the urine samples for all the tested $^{99m}$Tc-peptides were identical to those of the parent $^{99m}$Tc-peptides. No peak other than that corresponding to the $^{99m}$Tc-peptide construct was detected in any profiles, suggesting that the $^{99m}$Tc-peptide constructs are excreted intact through the kidneys, and do not undergo any metabolic degradation. This thus provides evidence that the $^{99m}$Tc-peptide constructs tested, and generally the metallopeptides of this invention, are metabolically stable. The following table shows the $^{99m}$Tc-peptide constructs that were assayed:

TABLE 1

Result of RP-HPLC of Urine Following Intravenous or Subcutaneous Administration of $^{99m}$Tc-Labeled Constructs

| $^{99m}$Tc-Labeled Construct | Routes of Administration | Time Point (Min.) | % Peak Bound of Labeled Construct | % Peak Bound In Urine |
|---|---|---|---|---|
| $^{99m}$Tc-[Arg-Gly-Cys]-β-Ala | iv | 30–120 | 100% | 100% |
| $^{99m}$Tc-[D-Arg-Gly-D-Cys]-β-Ala, | iv, sc | 30–120 | 100% | 100% |
| $^{99m}$Tc-[Arg-Gly-D-Cys]-β-Ala | iv | 30–120 | 100% | 100% |
| $^{99m}$Tc-[D-Arg-Gly-Cys]-β-Ala | iv | 30–120 | 100% | 100% |
| $^{99m}$Tc-[Gly-Arg-D-Cys]-β-Ala | iv | 30–120 | 100% | 100% |
| $^{99m}$Tc-[Gly-D-Arg-D-Cys]-β-Ala | iv | 30–120 | 100% | 100% |
| $^{99m}$Tc-[Gly-D-Arg-Cys]-β-Ala | iv | 30–120 | 100% | 100% |
| $^{99m}$Tc-[Gly-Arg-Cys]-β-Ala | iv | 30–120 | 100% | 100% |
| Thr-$^{99m}$Tc-[D-Lys-Gly-D-Cys]-Arg | iv, sc, oral | 30–120 | 100% | 100% |
| Tyr-$^{99m}$Tc-[Gly-Phe-NH-(CH$_2$)$_2$SH] | iv | 30–120 | 100% | 100% |

EXAMPLE 45

Oral Bioavailability of THR-$^{99m}$Tc-[D-Lys-Gly-D-Cys]-Arg

Figure 14:
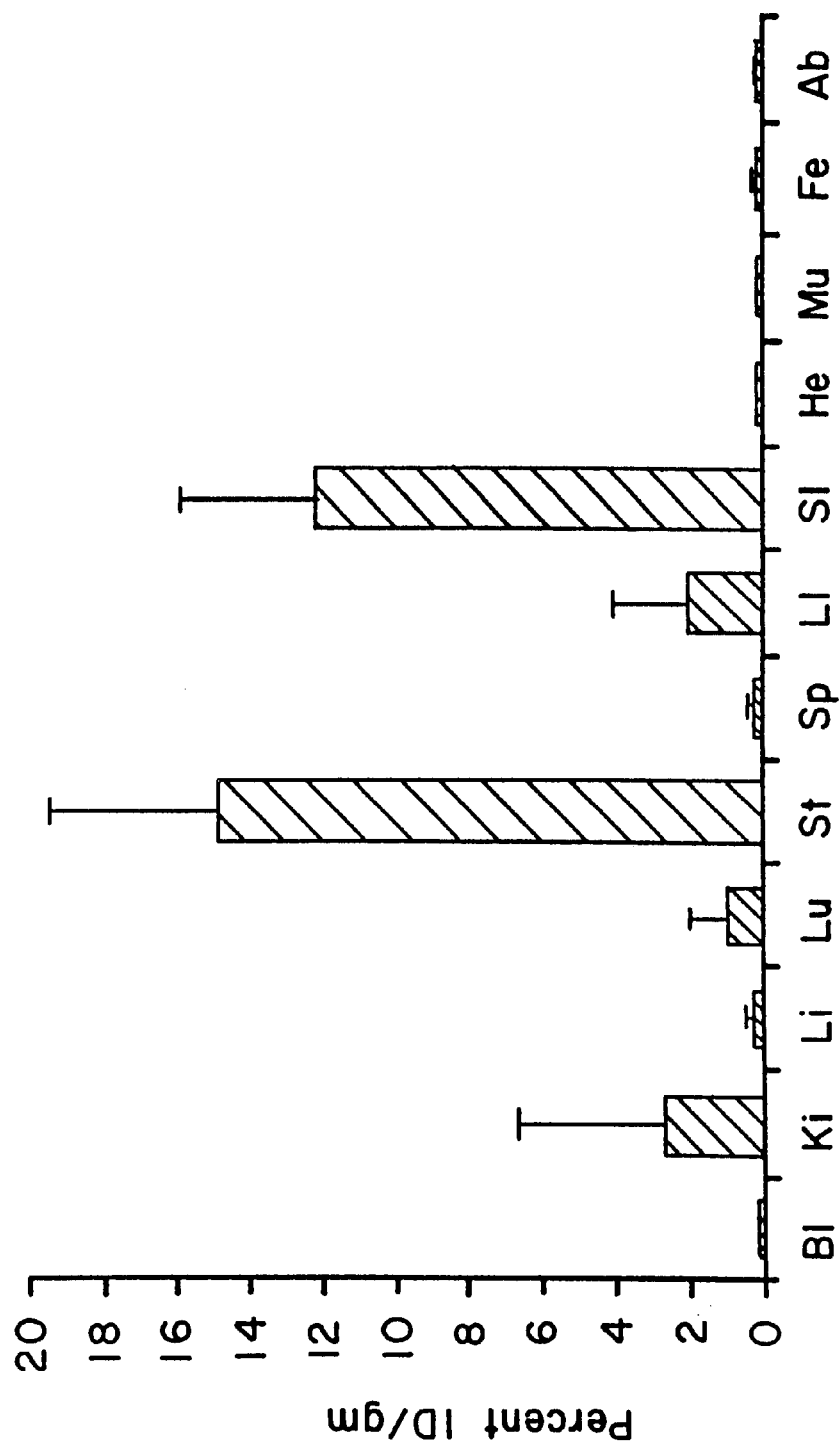
FIG. 14 shows the biodistribution profile of $^{99m}$Tc-Thr-[D-Lys-Gly-D-Cys]-Arg in mice two hours after its oral administration. Percent of injected dose per gram (percent ID/gm) of various organs is shown. Bl is blood, Ki is kidney, Li is liver, Lu is lung, St is stomach, Sp is spleen, LI is large intestine, SI is small intestine, He is heart, Mu is normal thigh muscle, Fe is femur and Ab is the inflammation site in thigh muscle.

10 μg kit was prepared according to Example 23, and labeled with 5 mCi of $^{99m}$Tc with a final volume of 1.5 mL. Alternatively, direct labeling methods or other kit formulation described herein could also be used. The preparation was analyzed by HPLC to ascertain complexation of $^{99m}$Tc to the peptide, and analyzed by SepPak-C18 cartridges to ascertain the amount of the colloid present in the labeled kit. A measured amount of Thr-$^{99m}$Tc-[D-Lys-Gly-D-Cys]-Arg in the range of 170–250 μCi (50–75 μl total volume) was administered orally in each of six mice that had been given a ketamine injection (10 μg in 100 μl) in the right thigh muscle one hour earlier to induce a localized inflammation. The administration of Thr-$^{99m}$Tc-[D-Lys-Gly-D-Cys]-Arg was done under ketamine anesthesia injected i.p. The injected animals were then transferred back to their cages and were allowed unrestrained movement. After 120 minutes the animals were sacrificed and death scintigraphic images for whole body radioactivity distribution were taken with a scintigraphic camera equipped with an open collimator. The animals were dissected and their major organs removed, weighed, and counted for radioactivity in a gamma counter. The ketamine inflamed muscle was also removed for measuring accumulation of radioactivity at this site, with a similar piece of muscle from the contralateral leg removed for comparison purposes. The scintigraphic images of the sacrificed animals showed clear visualization of the ketamine-induced inflammation. The radioactive peptide was also observed to be distributed throughout the body, which was indicative of effective oral absorption of the peptide, and transiting to the circulatory system. A large amount of activity, however, was present in the gut. The orally-absorbed portion of the peptide was apparently excreted entirely through the renal route, as was evident from higher accumulation in the kidney. Selected organ biodistributions are shown in FIG. 14. No other significant organ accumulation was observed. The ketamine inflamed muscle showed 7.7 times the accumulation of the contralateral muscle. The inflamed muscle to blood ratio was 1:1.6.

Independent urine analysis from these animals by reversed-phase HPLC technique as described in Example 44 revealed the presence of intact Thr-$^{99m}$Tc-[D-Lys-Gly-D-Cys]-Arg in the urine, providing additional evidence of oral absorption of the intact peptide. These studies, therefore, provide evidence showing Thr-$^{99m}$Tc-[D-Lys-Gly-D-Cys]Arg is an inflammation imaging agent which is orally absorbed in pharmacologically significant amounts, is metabolically stable in vivo, and is excreted intact in the urine.

EXAMPLE 46

Isosteric Replacement of a Disulfide Bridge in a Cyclic Somatostatin Peptide

A Somatostatin Analogue with a Disulfide Bridge Isoster: The biological activity of somatostatin and its analogues depends on the integrity of its disulfide bond. Reduction of this bond that opens up the ring structure is known to be detrimental to its biological activity. A typical and known somatostatin molecule is of the formula:

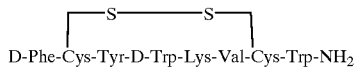

D-Phe-Cys-Tyr-D-Trp-Lys-Val-Cys-Trp-NH$_2$

Following is a molecule of somatostatin designed according to the method of this invention that has a $^{99m}$Tc, $^{99}$Tc, $^{188}$Re, or $^{186}$Re binding domain that replaces a disulfide bridge in the parent somatostatin analogue described above:

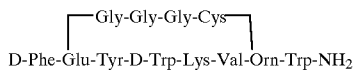

D-Phe-Glu-Tyr-D-Trp-Lys-Val-Orn-Trp-NH$_2$

This molecule after binding to the requisite metal ion gains biological activity, and binds to the somatostatin receptor.

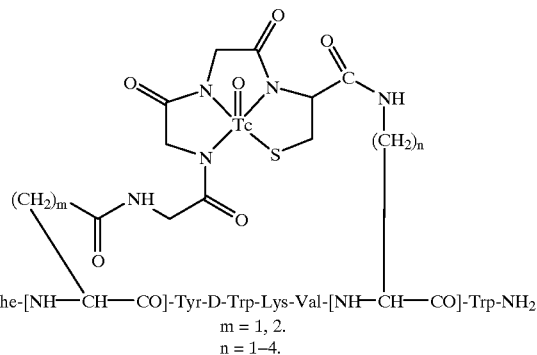

D-Phe-[NH—CH—CO]-Tyr-D-Trp-Lys-Val-[NH—CH—CO]-Trp-NH$_2$
m = 1, 2.
n = 1–4.

The metal ion-binding domain, here Gly-Gly-Gly-Cys, can be substituted with other metal ion-binding domains, including but not limited to, Gly-Gly-Cys and Gly-Gly-His, in both L- and D-configurations, as well as other constructs composed of amino acids and mimics thereof, each amino acid or mimic including an N, an S, two Ns or an N and S available to satisfy the valences of the metal ion coordination sphere.

This molecule can be easily synthesized by well known methods of solid-phase peptide synthesis. The labeling of this molecule with metal ions can be achieved easily by methods described in Examples 5–10, or modifications thereof.

EXAMPLE 47
Isosteric Replacement of a Lactam Bridge in a Cyclic Melanotropin Peptide A Melanotropin Analogue with a Lactam Bridge Isoster: The high potency of the melanotropin analogue described below depends on the integrity of its lactam bridge. Absence of this bridge, and the resulting lack of conformational constraint, is known to be detrimental to its biological activity. A melanotropin cyclic peptide of the general formula Ac-Nle-Asp-His-D-Phe-Arg-Trp-Lys-NH$_2$ (with cyclic bridge between Asp and Lys)

was used as the starting material.

The following molecule is designed according to the method of this invention, and has a $^{99m}$Tc, $^{99}$Tc, $^{188}$Re, or $^{186}$Re binding domain that replaces the lactam bridge in the parent melanotropin analogue:

Ac-Nle-Asp-His-D-Phe-Arg-Trp-Lys-NH$_2$ (with Gly-Gly-Gly-Cys bridge between Asp and Lys)

This precursor molecule, after binding to the requisite metal ion, has biological activity at the melanotropin receptor.

Ac-Nle-[NH—CH—CO]-His-D-Phe-Arg-Trp-[NH—CH—CO]—NH$_2$
m = 1.2.
n = 1–4.

The metal ion-binding domain, here Gly-Gly-Gly-Cys, can be substituted with other metal ion-binding domains, including but not limited to, Gly-Gly-Cys and Gly-Gly-His, in both L- and D-configurations, as well as other constructs composed of amino acids and mimics thereof, each amino acid or mimic including an N, an S, two Ns or an N and S available to satisfy the valences of the metal ion coordination sphere.

This molecule can been easily synthesized by well known methods of solid-phase peptide synthesis. The labeling of this molecule with metal ions can be achieved easily by methods described in Examples 5–10, or modifications thereof.

EXAMPLE 48
Somatostatin Analogue Peptide for $^{111}$In Labeling

A linear peptide D-Phe-Lys(N$^\epsilon$ bis carboxymethyl)-Tyr-D-Trp-Lys-Val-Lys(N$^\epsilon$ bis carboxylmethyl)-Trp-NH$_2$ is synthesized according to well established methods of solution phase or solid phase peptide synthesis. This sequence, after complexation with $^{111}$In, binds to somatostatin receptors. A solution of the peptide is made in an appropriate buffer and is mixed with $^{111}$InCl$_3$ to yield $^{111}$In-labeled peptide species in which the conformation of the peptide is folded and fixed by the complexation of the $^{111}$In metal ion to the carboxymethyl groups placed on the $\epsilon$-amino groups of the two lysine residues in the peptide sequence. Those peptide molecules which are not complexed to $^{111}$In do not bind the somatostatin receptor.

EXAMPLE 49
Melanotropin Analogue Peptide for $^{111}$In Labeling

A peptide, Ac-Nle-Lys(N$^\epsilon$ bis carboxymethyl)-His-D-Phe-Arg-Trp-Lys(N$^\epsilon$ bis carboxylmethyl)-NH$_2$, is synthesized according to established methods of solution phase or solid phase peptide synthesis. After complexation with $^{111}$In this peptide binds to melanotropin receptors. A solution of the peptide is made in an appropriate buffer and is mixed with $^{111}$InCl$_3$ to yield $^{111}$In-labeled peptide species in which the conformation of the peptide is fixed by the complexation of the $^{111}$In metal ion to the carboxymethyl groups placed on the $\epsilon$-amino groups of the two lysine residues in the peptide sequence. The portion of the peptide molecules that remain uncomplexed to $^{111}$In do not bind melanotropin receptors.

EXAMPLE 50
Estrogen Analogue Peptide for Tc or Re Labeling

A peptide derivative, Tic(7-OH)-Thr-NH(CH$_2$)$_2$SH or D-Tic(7-OH)-D-Thr-NH(CH$_2$)$_2$SH, is synthesized according to the well established methods of peptide synthesis as a ligand designed to mimic estrogen upon its complexation with $^{99m}$TcO[V] or ReO[V]. The peptide derivative Tic(7-OH)-Thr-NH(CH$_2$)$_2$SH has biological activity as an estrogen analogue after labeling with a metal ion, and has the following structure:

The peptide is labeled according to the methods similar to those described in Examples 5–10, or 23–24, or modifications thereof. The labeled molecule binds the estrogen receptor whereas the unlabeled molecule has little or no affinity for this receptor.

EXAMPLE 51
Alternate Estrogen Analogue Peptide for Tc or Re Labeling

A peptide derivative with the structure Tic(7-OH)-Ser-Cys or D-Tic(7-OH)-D-Ser-Cys is synthesized according to well established methods of peptide synthesis as another ligand designed to bind estrogen receptor after its complexation with $^{99m}$TcO[V] or ReO[V]. The peptide derivative Tic(7-OH)-Ser-Cys has biological activity as an estrogen analogue after labeling with a metal ion, and has the following structure:

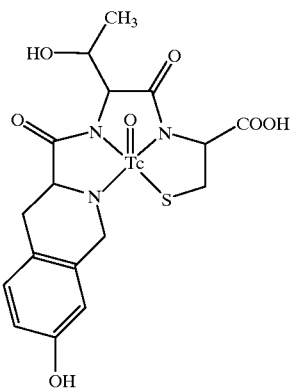

The peptide is labeled according to the methods similar to those described in Examples 5–10, or 23–24, or modifications thereof. The labeled molecule binds the estrogen receptor whereas the unlabeled molecule has little or no affinity for this receptor.

EXAMPLE 52
Laminin-Derived Yigsr Peptide Analogue for Tc or Re Labeling

Platelets contain a 67 kDa receptor which binds to laminin-derived peptide sequences containing Tyr-Ile-Gly-Ser-Arg (YIGSR) (Tandon N N, Holland E A, Kralisz U, Kleinman H K, Robey F A, and Jamieson G A: Interaction of human platelets with laminin and identification of the 67 kDa laminin receptor on platelets. *Biochem J* 274:535–542, 1991). This platelet receptor appears to play an important role in the interaction of platelets with the intact laminin molecule. Platelet adherence to laminin via this receptor does not in itself result in platelet activation (Ill CR, Engvall E, and Ruoslahti E: Adhesion of platelets to laminin in the absence of activation. *J Cell Biol* 99:2140–2145, 1984).

Peptides containing the YIGSR peptide sequence have been proposed as antimetastatic agents. U.S. Pat. No. 5,039,662, Peptide with Anti-Metastatic Activity, to Schasteen C S; U.S. Pat. No. 5,092,885, Peptides with Laminin Activity, to Yamada Y, Graf J O, Iwamoto Y, Rober F, Kleinman H K, Sasaki M and Martin G R; and U.S. Pat. No. 5,236,903, Polypeptide Comprising Repeated Cell-Adhesive Core Sequences, to Saiki I, Nishi N, Azuma I, Tokura S. These patents involve longer sequences containing the YIGSR peptide sequence, acylated YIGSR peptide sequences, cyclic YIGSR sequences, and repeated YIGSR linear sequences.

A peptide derivative, Tyr-Ile-Gly-Ser-Cys-Arg, <SEQ ID NO:5> is synthesized according to established methods of peptide synthesis as a ligand designed to mimic the adhesive pentapeptide sequence, YIGSR, of laminin upon its complexation with $^{99m}$TcO[V] or ReO[V]. The peptide is labeled according to the methods similar to those described in Examples 5–10, or 23–24, or modifications thereof. The labeled molecule binds the laminin receptor, while the unlabeled molecule has little or no affinity for this receptor.

EXAMPLE 53
Use of Somatostatin Analogues for Cancer Imaging

The somatostatin analogues of any of Examples 46 or 48 are labeled with between 5 and 20 mCi of $^{99m}$Tc, or in the case of Example 48, with between 2 and 10 mCi of $^{111}$In, using methods similar to those described in Examples 5–10, or 23–24, or modifications thereof. The analogues of this invention may be employed at a ratio of peptide to metal ion of as low as 2:1, and in some instances lower, and thus the minimum quantity of peptide is generally determined by the quantity of metal ion. Generally, the total amount of peptide will be between about 1 and 10 μg. The labeled somatostatin analogues are administered, by i.v. injection or regional delivery, to patients suspected of having somatostatin-receptor positive cancers, and periodic whole body scintigraphic images are obtained starting 10 minutes post-injection to determine the localization of the radiolabeled peptide to the tumor site or sites. The effectiveness of the labeled peptide to image these tumors is noted.

EXAMPLE 54
Use of Melanotropin Analogues for Cancer Imaging

The melanotropin analogues of any of Examples 47 or 49 are labeled with between 5 and 20 mCi of $^{99m}$Tc, or in the case of Example 49, with between 2 and 10 mCi of $^{111}$In, using methods similar to those described in Examples 5–10, or 23–24, or modifications thereof. The analogues of this invention may be employed at a ratio of peptide to metal ion of as low as 2:1, and in some instances lower, and thus the minimum quantity of peptide is generally determined by the quantity of metal ion. Generally, the total amount of peptide will be between about 1 and 10 μg. The labeled melanotropin analogues are administered, by i.v. injection or regional delivery, to patients suspected of having melanotropin-receptor positive cancers, such as melanomas, and periodic whole body scintigraphic images are obtained starting 10 minutes post-injection to determine the localization of the radiolabeled peptide to the tumor site or sites. The effectiveness of the labeled peptide to image these tumors is noted.

EXAMPLE 55
Use of Estrogen Analogues for Cancer Imaging

The estrogen analogues of any of Examples 50 and 51 are labeled with between 5 and 20 mCi of $^{99m}$Tc using methods similar to those described in Examples 5–10, or 23–24, or modifications thereof. The analogues of this invention may be employed at a ratio of peptide to metal ion of as low as 2:1, and in some instances lower, and thus the minimum quantity of peptide is generally determined by the quantity of metal ion. Generally, the total amount of peptide will be between about 1 and 10 μg. The labeled estrogen analogues are administered, by i.v. injection or regional delivery, to patients suspected of having estrogen-receptor positive cancers, such as breast cancer, and periodic whole body scintigraphic images are obtained starting 10 minutes post-injection to determine the localization of the radiolabeled peptide to the tumor site or sites. The effectiveness of the labeled peptide to image these tumors is noted.

EXAMPLE 56
Use of Somatostatin Analogues for Cancer Therapy

The somatostatin analogues of Example 46 are labeled with between 1 and 100 mCi of either $^{186}$Re or $^{188}$Re, using methods similar to those described in Examples 5–10, or 23–24, or modifications thereof, with increased Sn (II) concentrations as required to reduce the perrhenate. Patients are optimally selected who have demonstrated somatostatin-receptor positive tumors, which may conveniently be done by diagnostic imaging of Example 53. The analogues of this invention may be employed at a ratio of peptide to metal ion of as low as 2:1, and in some instances lower, and thus the minimum quantity of peptide is generally determined by the quantity of metal ion in the therapeutic radioisotope preparation. Generally, the total amount of peptide for therapeutic applications will be between about 5 and 25 μg. The labeled somatostatin analogues are administered, by i.v. injection or regional delivery, to patients suspected of having somatostatin-receptor positive cancers, with repeat administrations given as necessary to obtain the desired therapeutic effect. Since both $^{186}$Re and $^{188}$Re emit both gamma and beta radiation, periodic whole body gamma scintigraphic images may be obtained starting as soon as 10 minutes post-injection to determine the localization of the radiolabeled peptide to the tumor site or sites. The effectiveness of the labeled peptide to treat these tumors is noted.

EXAMPLE 57

Use of Melanotropin Analogues for Cancer Therapy

The melanotropin analogues of Example 47 are labeled with between 1 and 100 mCi of either 186Re or $^{188}$Re, using methods similar to those described in Examples 5–10, or 23–24, or modifications thereof, with increased Sn (II) concentrations as required to reduce the perrhenate. Patients with melanoma are optimally selected who have demonstrated melanotropin-receptor positive tumors, which may conveniently be done by diagnostic imaging of Example 54. The analogues of this invention may be employed at a ratio of peptide to metal ion of as low as 2:1, and in some instances lower, and thus the minimum quantity of peptide is generally determined by the quantity of metal ion in the therapeutic radioisotope preparation. Generally, the total amount of peptide for therapeutic applications will be between about 5 and 25 µg. The labeled melanotropin analogues are administered, by i.v. injection or regional delivery, to patients suspected of having melanoma or melanotropin-receptor positive cancers, with repeat administrations given as necessary to obtain the desired therapeutic effect. Since both $^{186}$Re and $^{188}$Re emit both gamma and beta radiation, periodic whole body gamma scintigraphic images may be obtained starting as soon as 10 minutes post-injection to determine the localization of the radiolabeled peptide to the tumor site or sites. The effectiveness of the labeled peptide to treat these tumors is noted.

EXAMPLE 58

Use of Estrogen Analogues for Cancer Therapy

The estrogen analogues of any of Examples 50 and 51 are labeled with between 1 and 100 mCi of either $^{186}$Re or $^{188}$Re, using methods similar to those described in Examples 5–10, or 23–24, or modifications thereof, with increased Sn (II) concentrations as required to reduce the perrhenate. Patients are optimally selected who have demonstrated breast cancer or other estrogen-receptor positive tumors, which may conveniently be done by diagnostic imaging of Example 55. The analogues of this invention may be employed at a ratio of peptide to metal ion of as low as 2:1, and in some instances lower, and thus the minimum quantity of peptide is generally determined by the quantity of metal ion in the therapeutic radioisotope preparation. Generally, the total amount of peptide for therapeutic applications will be between about 5 and 25 µg. The labeled estrogen analogues are administered, by i.v. injection or regional delivery, to patients suspected of having estrogen-receptor positive cancers, with repeat administrations given as necessary to obtain the desired therapeutic effect. Since both $^{186}$Re and $^{188}$Re emit both gamma and beta radiation, periodic whole body gamma scintigraphic images may be obtained starting as soon as 10 minutes post-injection to determine the localization of the radiolabeled peptide to the tumor site or sites. The effectiveness of the labeled peptide to treat these tumors is noted.

EXAMPLE 59

Imaging of Thrombosis Using $^{99m}$Tc-D-Arg-Gly-D-Cys-β-Ala

The RGD analogue D-Arg-Gly-D-Cys-β-Ala of any of Examples 1–4 is radiolabeled by any of the methods of Examples 5–10, or 23–24, or modifications thereof, with between 5 and 20 mCi of $^{99m}$Tc. The analogues of this invention may be employed at a ratio of peptide to metal ion of as low as 2:1, and in some instances lower, and thus the minimum quantity of peptide is generally determined by the quantity of metal ion. Generally, the total amount of peptide for diagnostic imaging applications will be between about 1 and 10 µg. The labeled RGD analogue is administered by i.v. injection to patients suspected of having thrombosis or a blood clot, and periodic whole body scintigraphic images are obtained starting 10 minutes post-injection to determine the localization of the radiolabeled peptide to accumulations of platelets, including sites of thromboses or blood clots. The effectiveness of the labeled peptide to image thrombosis is noted.

EXAMPLE 60

Imaging of Tumors using $^{99m}$Tc-D-Arg-Gly-D-Cys-β-Ala

The RGD analogue D-Arg-Gly-D-Cys-β-Ala of any of Examples 1–4 is radiolabeled by any of the methods of Examples 5–10, or 23–24, or modifications thereof, with between 5 and 20 mCi of $^{99m}$Tc. The analogues of this invention may be employed at a ratio of peptide to metal ion of as low as 2:1, and in some instances lower, and thus the minimum quantity of peptide is generally determined by the quantity of metal ion. Generally, the total amount of peptide for diagnostic imaging applications will be between about 1 and 10 µg. The labeled RGD analogue is administered, by i.v. injection or regional delivery, to patients suspected of having metastatic or other tumors, and periodic whole body scintigraphic images are obtained starting 10 minutes post-injection to determine the localization of the radiolabeled peptide to the tumor site or sites. The effectiveness of the labeled peptide to image these tumors is noted.

EXAMPLE 61

Design and Synthesis of Tetradendate Metal Ion RGD Analogue

A peptide derivative D-Arg-Gly-His-β-Ala is synthesized according to the well established methods of peptide synthesis, such as the methods of Examples 1 to 3 or modifications thereof. The peptide derivative D-Arg-Gly-His-β-Ala is complexed with a tetradendate metal ion, such as Cu, Co, Zn, Ni, or Mn. Upon complexation to the metal ion, the peptide binds specifically to the heterodimeric receptor GP IIb/IIIa on activated platelets. This peptide-metal ion complex therefore is able to bind thrombus in vivo and may find use as an anti-thrombus agent and as an therapeutic agent for myocardial infarction. A complex of this peptide with Mn may also be utilized for locating deep vein thrombi or pulmonary emboli in mammals by magnetic resonance imaging techniques. The peptide molecules without the metal ion are either inactive or extremely weak ligands for the platelet receptor.

EXAMPLE 62

Design and Synthesis of Tetradendate Metal Ion Tuftsin Analogue

A peptide derivative Thr-D-Lys-Gly-D-His-Arg is synthesized according to the well established methods of peptide synthesis, such as the methods of Examples 1 to 3 or modifications thereof. The peptide derivative Thr-D-Lys-Gly-D-His-Arg is complexed with a tetradendate metal ion, such as Cu, Co, Zn, Ni, or Mn. Upon complexation to the metal ion, the peptide binds specifically to the tuftsin receptor on polymorphonuclear leukocytes and macrophages and stimulates phagocytosis in these cells. This peptide-metal ion complex therefore may be utilized to enhance the biological actions that are mediated through PMN leukocytes and macrophages in fighting infection and antigen processing and presentation. A complex of this peptide with Mn may also be utilized for locating infection and inflammation foci in mammals by magnetic resonance imaging techniques. The peptide molecules without the metal ion are either inactive or extremely weak ligands for the tuftsin receptor.

EXAMPLE 63
Synthesis and Stability of Thr-ReO[V]-[D-Lys-Gly-D-His]-Arg as a Phagocyte Stimulatory Compound The peptide Thr-D-Lys-Gly-D-His-Arg is designed and synthesized as another peptide to bind the tuftsin receptor on granulocytes after complexation with ReO[V] as described in Example 41. This peptide is designed to contain an $N_4$ ligand for metal complexation. Three of the four nitrogens coordinating the Re metal ion are part of the peptide backbone, while the fourth nitrogen is the imidazole nitrogen from the side chain of His residue. 32 mg of this peptide as its trifluroacetate salt is reacted with 40 mg of oxotrichlorobis(triphenylphosphine)rhenium[V], and is purified by HPLC methods as described in Example 41. Formation of the Re-labeled peptide can easily be confirmed by UV absorption at λ 320–360 nm, circular dichroism studies, elemental analysis and electron spray mass spectrometry (ES-MS).

EXAMPLE 64
$^{99m}$Tc-labeled Thr-D-Lys-Gly-D-His-Arg as a Radiolabeled Phagocyte Stimulatory Compound Direct Labeling of the Peptide: The peptide Thr-D-Lys-Gly-D-His-Arg was designed with an $N_4$ metal ion-binding domain, and with a biological-function domain mimicing the tuftsin receptor. The peptide was synthesized as described in Example 21 and labeled with $^{99m}$Tc in a stannous reducing agent containing sodium glucoheptonate as described in Method B of Example 23. Briefly, between 1–10 μg of the peptide was mixed with generator-eluted $^{99m}$Tc-sodium pertechnetate (1–35 mCi of radioactivity in 0.5–3.5 mL volume), to which was added a nitrogen-purged solution (200–400 μL) of stannous-glucoheptonate buffer (1 mM–200 mM, pH 7.5–8.5). The head space of the vial was purged with nitrogen and the solution incubated either at room temperature for 60 minutes or in a boiling water bath for 15 minutes. The solution, after cooling, was optionally diluted further with saline. A small aliquot of this $^{99m}$Tc-labeled peptide was analyzed by RP-HPLC on a C-18 column, with the radioelution profile showing two peaks (retention times of 11.2 and 13 min). The first peak was generally in a higher amount than the second, with the ratio of the two peaks ranging from 3:1 to 5:1. Samples of the labeled peptide were also assayed using ITLC strips and SepPak cartridges as described in Example 23. In general 75–85% of the radioactivity was found to be peptide bound, with 10–20% of radioactivity eluted as uncomplexed $^{99m}$Tc and 1–3% shown to be $^{99m}$Tc-colloid.

EXAMPLE 65
Cu Metal Ion Binding D-Arg-Gly-D-His-βAla Peptide Construct

The peptide derivative D-Arg-Gly-D-His-β-Ala is synthesized according to established methods of the peptide synthesis, as generally described in Examples 1 to 3, as a ligand that after complexation with a tetradentate metal ion such as Cu, Co, Zn, Ni, or Mn binds specifically to the heterodimeric receptor GP IIb-IIIa on activated platelets. This peptide-metal ion complex will thus bind thrombus in vivo and may find use as an anti-thrombus agent and as a therapeutic agent for myocardial infraction. A complex of this peptide with Mn may also be utilized for locating deep vein thrombi or pulmonary emboli in mammals by magnetic resonance imaging techniques. The peptide molecules without the metal ion are either inactive or extremely weak ligands for the platelet receptor.

EXAMPLE 66
Cu Metal Ion Binding Thr-D-Lys-Gly-D-His-Arg Peptide Construct

The peptide derivative Thr-D-Lys-Gly-D-His-Arg is synthesized according to established methods of the peptide synthesis, as generally described in Examples 1 to 3, as a ligand that after complexation with a tetradentate metal ion such as Cu, Co, Zn, Ni, or Mn binds specifically to the tuftsin receptor on polymorphonuclear leukocytes and macrophages and stimulates phagocytosis in these cells. This peptide-metal ion complex therefore may be utilized to enhance the biological actions that are mediated through PMN leukocytes and macrophages in fighting infection, and antigen processing and presentation. A complex of this peptide with Mn may also be utilized for locating infection and inflammation foci in mammals by magnetic resonance imaging techniques. The peptide molecules without the metal ion are either inactive or extremely weak ligands for the platelet receptor.

EXAMPLE 67
Construction of a Solid Phase Library of Metallopeptides Directed Towards Various Integrin Receptors Well established methods of peptide synthesis are used to obtain a library of linear peptides. A p-methylbenzhydramine linked polystyrene resin (substitution level 0.2–0.35 mM/gm) is derivatized with 6-N-Fmoc-aminohexanoic acid to act as a spacer between the resin and peptide chain. The Fmoc group is deblocked with 20% piperidine, the resin split into eight equal parts, and each individual part is coupled separately with only one of the following Fmoc-protected amino acid derivatives: Asp, Glu, N-Me-Asp, N-Me-Glu, D-Asp, D-Glu, D-N-Me-Asp, and D-N-Me-Glu. After the completion of these couplings, all eight resin parts are mixed together, the Fmoc group deblocked and the resin is again divided into four equal parts. Each individual part is coupled separately with only one of these Fmoc-protected amino acid derivatives: Cys(Trt), His(Trt), D-Cys(Trt), D-His(Trt). After completion of the coupling reaction, the resin is again combined, the Fmoc group deblocked and Fmoc-Gly is coupled to this resin. After removal of the Fmoc group from the glycine, the resin is divided into 16 equal parts. Each part is reacted with only one of the following 16 amino acid derivatives: Fmoc-Arg(Pmc), Fmoc-Lys(Boc), Fmoc-Orn(Boc), Fmoc-Apr(Boc), Fmoc-Abu(Boc), Fmoc-Aec(Boc), Fmoc-Apc(Boc), Fmoc-D-Arg(Pmc), Fmoc-D-Lys(Boc), Fmoc-D-Orn(Boc), Fmoc-D-Apr(Boc), Fmoc-D-Abu(Boc), Fmoc-D-Aec(Boc), Fmoc-D-Apc(Boc). After the completion of the couplings all the peptide resins are again pooled together. The Fmoc group is removed first, followed by the removal of the Boc group and other acid labile side chain protecting groups from various amino acids under a nitrogen atmosphere. The peptide resin obtained in this manner is then reacted with oxotrichlorobis-(triphenylphosphine)rhenium[V] in the presence of sodium acetate to complex rheniumoxo ions to the peptides. The resulting library of 512 (8×4×1×16) rhenium-peptide complexes obtained in this manner is stored for use in bioassays.

EXAMPLE 68
Construction of Solid Phase Library of Metallopeptides Directed Towards Various Integrin Receptors with Orthogonal Multiple Release Linker System A library of 512 metallopeptides as described in Example 67 may also be synthesized using the orthogonal multiple release linker system described by M. Lebl and co-workers (Lebl M, Krchnak V, Sepetov N F, Seligmann B, Strop P, Felder S, Lam K S: One-bead-one-structure combinational libraries. *Biopolymers (Peptide Sci)* 37:177–198, 1995), incorporated herein by reference, so that partial amounts of peptides can be released from the beads for bioassy in solution. For this purpose, the linker is first attached to the resin as described by M. Lebl et al, followed by the coupling of amino acids according to Example 67. Complexation of metal ions is also done according to the method described in Example 67.

EXAMPLE 69
Construction of Solid Phase Library of Metallopeptides Directed Towards Various Integrin Receptors with Photolinker Release System A library of 512 metallopeptides as described in Example 67 may also be synthesized using a photolabile peptide release linker system described by J. C. Chabala in *Synthetic Chemical Libraries in Drug Development,* London, 1995, so that peptides can be released from the beads for their bioassays in solution. For this purpose, first the linker is attached to the resin as described by J. C. Chabala, followed by the coupling of amino acids according to Example 67. Complexation of metal ions is also done according to the methods described in Example 67.

EXAMPLE 70
Construction of Solid Phase Library of Metallopeptides Directed Towards Various Integrin Receptors A library of 512 metallopeptides as described in Example 67 may also be synthesized using Boc chemistry for peptide synthesis. The general synthetic strategy of constructing the library remains the same except that Boc-protected amino acids are used. The side chain functionalities of these amino acids are protected by base labile protecting groups, such as Fmoc. The general methodologies are known to those skilled in the art and are generally described in the reference in Example 67.

EXAMPLE 71
Alternate Solid Phase Library Synthesis

The library of 512 metallopeptides described in Example 67 can also be synthesized on pins as described by M. Gysin (*Proc Natl Acad Sci USA* 81:3998, 1984). Both Fmoc (Example 67) and Boc (Example 70) strategies are employed for this purpose. The metallopeptides made in this manner on these pins are assayed directly in multititer plate assay system as described by M. Gysin.

EXAMPLE 72
Alternative Solid Phase Library Synthesis

The library of 512 metallopeptides described in Example 67 can also be synthesized on various other resins, such as Tentagel resin, Merrifield resin, PAM resin, Wang resin, Polyamide resin, Oxime resin, and other resins known in the art. These resins have been described in references given in Example 67. Other descriptions of resins are included in Fields GB et al: Principles and practice of solid-phase peptide synthesis, in *Synthetic Peptides, A User Guide,* cited above, at pp. 77–183. Various linkers described in Examples 68 and 69 may also be employed with these resins.

EXAMPLE 73
Synthesis of Soluble Peptide Library

A library of 512 metallopeptides on solid phase as described in Examples 67, 70 and 72 may also be obtained as a soluble library. For this purpose, the mixture of 512 peptides made on solid phase as described is cleaved from the resin using appropriate cleaving reagents. Depending on the nature of the resin and cleaving agent employed in the synthesis (see Fields GB et al, supra), the resulting peptides are obtained as either free acids, amides, hydrazides, or esters. The resulting peptide mixture is then reacted with oxotrichlorobis-(triphenyl phosphine)rhenium[V] in the presence of sodium acetate in methanol to complex rheniumoxo ions to the peptides. This method yields quantitative conversion of the peptides to metallopeptide complexes.

EXAMPLE 74
Peptide Libraries Using Other Metal Ions

A library of 512 peptides synthesized according to Examples 67 and 70 (solid-phase library) or Example 73 (soluble library) is treated with Zn, Co, Mn, Fe or Cu ions (as chloride or other suitable salts of these metal ions) to yield the library of corresponding metal ion complexed peptides. Essentially, a variety of metal ions can be used to construct different metallopeptide libraries. In the case of soluble libraries, the complexation can be verified by analytical techniques such as high performance liquid chromatography, and spectroscopic methods such as mass spectrometry, infrared spectroscopy, ultraviolet spectroscopy, and preferably by circular dichroism. In the case of resin bound metallopeptide libraries, the most appropriate analytical approach is matrix-assisted laser desorption/ionization (MALDI) techniques (Siuzadak G et al: *Bioorg Med Chem Lett* 6:979, 1996; Brown B B et al: *Molecular Diversity* 1:4–12, 1995).

All of the foregoing are merely illustrative, and other equivalent embodiments are possible and contemplated.

Although this invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

What is claimed is:

1. A pharmaceutical composition comprising a cyclic peptide with a metal ion-binding backbone comprising at least two contiguous amino acid residues, wherein said amino acid residues forming the metal ion-binding backbone have a single sulfur atom and a plurality of nitrogen atoms available for complexing with a metal ion; and a metal ion complexed to the single sulfur atom and one or more of the nitrogen atoms forming a part of the metal ion-binding backbone.

2. The composition of claim 1, wherein the cyclic peptide further comprises at least two amino acid residues forming a biological-function domain.

3. The composition of claim 2, wherein the biological-function domain is substantially more potent upon the metal ion-binding backbone being complexed with the metal ion.

4. The composition of claim 1, wherein the metal ion is an ionic form of the element selected from the group consisting of iron, cobalt, nickel, cooper, zinc, manganese, arsenic, selenium, technetium, ruthenium, palladium, silver, cadmium, indium, antimony, rhenium, osmium, iridium, platinum, gold, mercury, thallium, lead, bismuth, polonium or astatine.

5. The composition of claim 1, wherein the metal ion is radioactive or paramagnetic.

6. The composition of claim 2, wherein the biological-function domain comprises a ligand forming a member of a ligand and receptor pair.

7. The composition of claim 1, wherein all of the valences of the metal ion are satisfied upon complexation of the metal ion.

8. A manufactured cyclic peptide and pharmaceutically acceptable salts thereof comprising a metal ion-binding backbone including two or more contiguous amino acids available for complexing with a metal ion, and a biological-function domain, which biological-function domain is conformationally constrained upon complexing the metal ion-binding backbone with a metal ion.

9. A manufactured cyclic peptide and pharmaceutically acceptable salts thereof with a conformationally constrained secondary structure upon complexing with a metal ion, the conformationally constrained secondary structure comprising a member of a ligand and receptor pair, said peptide being of the general formula:

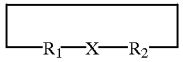

wherein X is a complexing backbone for complexing a metal ion comprising a plurality of contiguous amino acids;

wherein a single sulfur atom and a plurality of nitrogen atoms are available for complexing with a metal ion so that substantially all of the valences of the metal ion are satisfied upon complexation of the metal ion with X;

wherein X has, upon complexing with the metal ion, a specific regional secondary structure forming at least a part of the global secondary structure;

wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained secondary structure;

wherein $R_1$ and $R_2$ are covalently linked together; and wherein the conformationally constrained secondary structure comprising at least a part of X, $R_1$ or $R_2$ comprises a ligand capable of forming a member of a ligand and receptor pair.

10. The peptide of claim 9 wherein if less than all of the valences of the metal ion are otherwise satisfied upon complexation of the metal ion with the amino acids comprising X, then X also comprises a derivatized amino acid or spacer sequence, which derivatized amino acid or spacer sequence comprises at least one nitrogen, sulfur or oxygen atom available for complexing with the available valences of the metal ion, so that all of said valences of the metal ion are satisfied upon complexation of the metal ion with X.

11. The cyclic peptide of claim 9 wherein $R_1$ and $R_2$ are covalently linked together through an amide, disulfide, thioether, thioester, urethane, or ester linkages.

12. The cyclic peptide of claim 10 wherein the covalent linkage between $R_1$ and $R_2$ is a linkage through the end groups of $R_1$ and $R_2$, linkage through side chain functionalities of any amino acid within $R_1$ and $R_2$, linkage through the end group of $R_1$ and a side chain functionality of any amino acid in $R_2$, or linkage through the end group of $R_2$ and a side chain functionality of any amino acid in $R_1$.

13. The cyclic peptide of claim 9 which is a cyclic peptide of the formula:

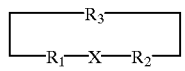

wherein $R_3$ comprises from 1 to about 20 amino acids.

14. The cyclic peptide of claim 13 wherein $R_3$ forms a part of the conformationally constrained secondary structure.

15. A cyclic peptide, and pharmaceutically acceptable salts thereof, with a metal ion-binding backbone for isosteric replacement of a disulfide, thioether, lactam, or a lactone bridge, said cyclic peptide being of the general formula:

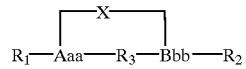

wherein X is a complexing backbone for complexing metal ion comprising a plurality of amino acids, so that substantially all of said valences of the metal ion are satisfied upon complexation of the metal ion with X, wherein $R_1$ and $R_2$ each comprise from 0 to about 20 amino acids, wherein $R_3$ comprises from 1 to about 20 amino acids, wherein Aaa and Bbb each comprise an amino acid connected to X through a disulfide, amide, thioether, thioester, urethane or ester bond.

16. The cyclic peptide of claim 15 wherein X is an amino acid sequence of the formula:

Ccc-Ddd-Eee or Eee-Ddd-Ccc, wherein each of Ccc and Ddd is an amino acid or dipeptide with uncharged side chains, and wherein Eee is a L- or D-isomer of Cys, HomoCys, Pen, or His.

* * * * *